United States Patent
Pickford et al.

(10) Patent No.: US 7,115,573 B2
(45) Date of Patent: Oct. 3, 2006

(54) PRODRUG COMPOUNDS WITH AN ISOLEUCINE

(75) Inventors: Lesley B. Pickford, Menlo Park, CA (US); Sanjeev Gangwar, Alameda, CA (US); Thomas J. Lobl, Valencia, CA (US); Matthew H. Nieder, Seattle, WA (US); Geoffrey T. Yarranton, Burlingame, CA (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 10/311,411

(22) PCT Filed: Jun. 11, 2001

(86) PCT No.: PCT/US01/18857

§ 371 (c)(1),
(2), (4) Date: Dec. 13, 2002

(87) PCT Pub. No.: WO01/95943

PCT Pub. Date: Dec. 20, 2001

(65) Prior Publication Data

US 2004/0039160 A1  Feb. 26, 2004

Related U.S. Application Data

(60) Provisional application No. 60/211,686, filed on Jun. 14, 2000.

(51) Int. Cl.
*A61K 38/06* (2006.01)
*A61K 38/07* (2006.01)
*C07K 5/083* (2006.01)
*C07K 5/10* (2006.01)

(52) U.S. Cl. .......................... 514/17; 514/18; 530/330; 530/331; 530/345

(58) Field of Classification Search ................ 530/329, 530/330, 331, 345; 514/17, 18
See application file for complete search history.

(56) References Cited

U.S. PATENT DOCUMENTS

| | | | |
|---|---|---|---|
| 4,277,466 A | 7/1981 | Trouet et al. | 514/34 |
| 4,296,105 A | 10/1981 | Baurain et al. | 514/34 |
| 4,376,765 A | 3/1983 | Trouet et al. | 514/18 |
| 4,388,305 A | 6/1983 | Trouet et al. | 514/19 |
| 4,639,456 A | 1/1987 | Trouet et al. | 514/283 |
| 4,671,958 A | 6/1987 | Rodwell et al. | 514/2 |
| 4,703,107 A | 10/1987 | Monsigny et al. | 530/330 |
| 4,719,312 A | 1/1988 | Firestone | 564/510 |
| 4,870,162 A | 9/1989 | Trouet et al. | 530/363 |
| 5,024,835 A | 6/1991 | Rao et al. | 530/324 |

(Continued)

FOREIGN PATENT DOCUMENTS

BE    869485 A    12/1978

(Continued)

OTHER PUBLICATIONS

Knight et al. Thimet oligopeptidase specificity . . . Biochemical Journal. 1995, vol. 308, pp. 145-150.*

(Continued)

*Primary Examiner*—Jeffrey Edwin Russel
(74) *Attorney, Agent, or Firm*—Lahive & Cockfield, LLP; Jane R. Remillard, Esq.; Cynthia M. Soroos, Esq.

(57) ABSTRACT

The compounds of the invention are modified forms of therapeutic agents. A typical prodrug compound of the invention comprises a therapeutic agent, an oligopeptide having an isoleucine residue, a stabilizing group and, optionally, a linker group. The prodrug is cleavable by an enzyme associated with the target cell. Methods of making and using the compounds are also disclosed.

41 Claims, 20 Drawing Sheets

U.S. PATENT DOCUMENTS

| | | | |
|---|---|---|---|
| 5,220,001 A | 6/1993 | Ok et al. | 536/6.4 |
| 5,393,784 A * | 2/1995 | Richardson | 514/561 |
| 5,599,686 A | 2/1997 | DeFeo-Jones et al. | 435/23 |
| 5,618,790 A | 4/1997 | Kennedy et al. | 514/12 |
| 5,916,921 A * | 6/1999 | Nishihira et al. | 514/561 |
| 5,962,216 A | 10/1999 | Trouet et al. | 435/4 |
| 6,143,864 A | 11/2000 | DeFeo-Jones et al. | 530/322 |
| 6,342,480 B1 | 1/2002 | Trouet et al. | 514/18 |
| 6,649,587 B1 * | 11/2003 | Frydman et al. | 514/2 |
| 6,844,318 B1 * | 1/2005 | Copeland et al. | 514/8 |
| 2002/0142955 A1 * | 10/2002 | Dubois et al. | 514/12 |
| 2003/0224971 A1 * | 12/2003 | Kumar et al. | 514/2 |

FOREIGN PATENT DOCUMENTS

| | | |
|---|---|---|
| BE | 882541 | 7/1980 |
| EP | 0 041 935 A1 | 12/1981 |
| EP | 0 044 090 A2 | 1/1982 |
| EP | 0 126 685 A1 | 11/1984 |
| EP | 0 208 615 B1 | 1/1987 |
| WO | WO 81/01145 A1 | 4/1981 |
| WO | WO 93/02703 A1 | 2/1993 |
| WO | WO 96/00503 A1 | 1/1996 |
| WO | WO 96/05863 A1 * | 2/1996 |
| WO | WO 96/33198 A1 | 10/1996 |
| WO | WO 00/33888 A * | 6/2000 |
| WO | WO 00/69472 A2 | 11/2000 |
| WO | WO 01/28593 A2 | 4/2001 |
| WO | WO 01/30804 A2 | 5/2001 |

OTHER PUBLICATIONS

Nichifor et al. Polymeric prodrugs of 5-fluorouracil. Journal of Controlled Release. 1997, vol. 48, pp. 165-178.*

Arribas et al. A Comparative Study of the Chymotrypsin-like Activity . . . The Journal Of Biological Chemistry. Oct. 5, 1993, vol. 268, No. 28, pp. 21165-21171.*

M. Dayhoff, Atlas of Protein Sequence and Structure, vol. 5. National Biomedical Research Foundation, p. 96 (1972).*

Kaneda et al. Antimetastatic effect of synthetic Glu-Ile-Leu-Asp-Val peptide derivatives containing D-amino acids. Anti-Cancer Drugs. 1997, vol. 8, pp. 702-707.*

Baurain R, Masquelier M, Deprez-De Campeneere D, Trouet A. Amino acid and dipeptide derivatives of daunorubicin. 2. Cellular pharmacology and antitumor activity on L1210 leukemic cells in vitro and in vivo. J Med Chem. Nov. 1980;23(11):1171-4.

Bricout, H., et al., "Synthetic and Kinetic Aspects of Nickel-Catalysed Amination of Allylic Alcohol Derivatives", Tetrahedron, 1998, 54:1078-1084.

Casimir, J.R., et al., "First Application of the Dakin-west Reaction to Fmoc Chemistry: Synthesis of the ketomethylene tripeptide Fmoc-N$^a$-ASP(tBu)-(R,S)Tyr(tBu)ψ(CO-CH$_2$)Gly-OH", 1995, Tetrahedron Letters, 1995, 36(27):4797-4800.

Chaires JB, Dattagupta N, Crothers DM. Self-association of daunomycin. Biochemistry. Aug. 17, 1982;21(17):3927-32.

Chakravarty PK, Carl PL, Weber MJ, Katzenellenbogen JA. Plasmin-activated prodrugs for cancer chemotherapy. 1. Synthesis and biological activity of peptidylacivicin and peptidylphenylenediamine mustard. J Med Chem. May 1983;26(5):633-8.

Eisenbrand, G., et al., "An Approach Towards More Selective Anticancer Agents", Synthesis, 1996, pp. 1246-1258.

Genêt, J.P., et al., "A General and Simple Removal of the Allyloxycarbonyl Protecting Group by Palladium-Catalyzed Reactions Using Nitrogen and Sulfur Nucleophiles", Synlett, Sep. 1993, No. 9:680-682.

Genêt, J.P., et al., "Practical Palladium-Meditated Deprotective Method of Allyloxycarbonyl in Aqueous Media", Tetrahedron, 1994, 50(2):497-503.

Hayakawa, E., et al., "Viscosity Study on the Self-Association of Doxorubicin in Aqueous Solution", Chem. Pharm. Bull., 1991, 39:1282-6.

Matzanke BF, Bill E, Butzlaff C, Trautwein AX, Winkler H, Hermes C, Nolting HF, Barbieri R, Russo U. Evidence for polynuclear aggregates of ferric daunomycin. A Mossbauer, EPR, X-ray absorption spectroscopy and magnetic susceptibility study. Eur J Biochem. Jul. 15, 1992;207(2):747-55.

Seitz, D.E., et al., "Synthesis and Chemical Properties of a Series of Doxonrubicin Enaminomalonyl-β-alanine Derivatives", Tetrahedron Letters, 1995, 36(9):1413-1416.

Schmittberger et al., "Synthesis of the Palmitoylated and Prenylated C-terminal Lipopeptides of the Human R-and N-Ras Proteins" Biororg. Med. Chem., 1998, 7:749-762.

Balajthy Z, et al. Synthesis and functional evaluation of a peptide derivative of 1-beta-D-arabinofuranosylcytosine. J Med Chem. Sep. 4, 1992;35(18):3344-9.

Baurain, et al. Antitumor Activity of Daunorubicin linked to proteins: Lysosomal hydrolysis and antitumor activity of conjugates prepared with peptidic spacer arms. Current Chemotherapy and Immunotherapy, Proceeding of the 12$^{th}$ International Congress of Chemotherapy. 1982. pp. 1430-1432.

Baurain, et al. Targeting of Daunorubicin by Covalent & Reversible Linkage to carrier Proteins. Lysosomal Hydrolysis and Antitumoral Activity of Conjugates Prepared with Peptidic Spacer Arms. Drugs Exp. Clin. Res. 1983 9:303-311.

Carl PL, et al. Protease-activated "prodrugs" for cancer chemotherapy. Proc Natl Acad Sci U S A. Apr. 1980;77(4):2224-8.

Chakravarty PK, et al. Plasmin-activated prodrugs for cancer chemotherapy. 2. Synthesis and biological activity of peptidyl derivatives of doxorubicin. J Med Chem. May 1983;26(5):638-44.

DeFeo-Jones D, et al. A peptide-doxorubicin 'prodrug' activated by prostate-specific antigen selectively kills prostate tumor cells positive for prostate-specific antigen in vivo. Nat Med. Nov. 2000;6(11):1248-52.

De Marre, et al. Evaluation of the hydrolytic and enzymatic stability of macromolecular Mitimycin C derivatives. Journal of Controlled Release. 1994 31:89-97.

Denny WA. Prodrug strategies in cancer therapy. Eur J Med Chem. Jul.-Aug. 2001;36(7-8):577-95.

Harnois-Pontoni M, et al. Hydrosoluble fluorogenic substrates for plasmin. Anal Biochem. Mar. 2, 1991;193(2):248-55.

Israel M, et al. Adriamycin analogues. Preparation and biological evaluation of some N-(trifluoroacetyl)-14-O-[(N-acetylamino)acyl]adriamycin derivatives. J Med Chem. Jul. 1986;29(7):1273-6.

Kandukuri, S.P., et al. Vinblastin-23-oyl amino acid derivatives: chemistry, physicochemical data, toxicity, and antitumor activities against P388 and L1210 leukemias. J Med Chem. Aug. 1985;28(8):1079-88.

Kennett CN, et al. Comparative histochemical, biochemical and immunocytochemical studies of cathepsin B in human gingiva. J Periodontal Res. May 1994;29(3):203-13.

Masquelier M, et al. Amino acid and dipeptide derivatives of daunorubicin. 1. Synthesis, physicochemical properties, and lysosomal digestion. J Med Chem. Nov. 1980;23(11):1166-70.

Masquelier, et al. Antitumor Activity of Daunorubicin Linked to Proteins: Biological and Antitumor Properties of Peptidic Derivatives of Daunorubicin Used as Intermediates. Current Chemotherapy and Immunotherapy, Proceedings of the 12$^{th}$ International Congress of Chemotherapy. 1982, pp. 1428-1430.

Mayer R, et al. Peptide derivatives specific for a Plasmodium falciparum proteinase inhibit the human erythrocyte invasion by merozoites. J Med Chem. Oct. 1991;34(10):3029-35.

Moss, Judi. Peptide Prodrugs Designed to Limit Metabolism. Washington DC. Am. Chem. Soc., 1995. Chapters 18, pp. 423-445.

Nestor, John J. Improved Duration of Action of Peptide Drugs. Washington DC. Am. Chem. Soc., 1995. p. 449-471.

Pan C, et al. CD10 is a key enzyme involved in the activation of tumor-activated peptide prodrug CPI-0004Na and novel analogues: implications for the design of novel peptide prodrugs for the therapy of CD10+ tumors. Cancer Res. Sep. 1, 2003;63(17):5526-31.

Pozsgay M, et al. A method for designing peptide substrates for proteases. Tripeptidyl-p-nitroanilide substrates for subtilisin Carlsberg. Eur J Biochem. Mar. 15, 1979;95(1):115-9.

Trail PA, et al. Cure of xenografted human carcinomas by BR96-doxorubicin immunoconjugates. Science. Jul. 9, 1993;261(5118):212-5.

Trouet A, et al. A covalent linkage between daunorubicin and proteins that is stable in serum and reversible by lysosomal hydrolases, as required for a lysosomotropic drug-carrier conjugate: in vitro and in vivo studies. Proc Natl Acad Sci U S A. Jan. 1982;79(2):626-9.

Whalley ET. Receptors mediating the increase in vascular permeability to kinins: comparative studies in rat, guinea-pig and rabbit. Naunyn Schmiedebergs Arch Pharmacol. Jul. 1987;336(1):99-104.

\* cited by examiner

| Symbol | Name | Structure |
|---|---|---|
| Aib | Aminoisobutyric Acid | $H_2N$—C($CH_3$)($CH_3$)—COOH |
| Amb | 4-(Aminomethyl)benzoic Acid | $H_2N$—$CH_2$—C$_6$H$_4$—COOH |
| APP | 3-Amino-3-phenylpropionic Acid | Ph—CH($NH_2$)—$CH_2$—COOH |
| Dg | Diglycolic Acid | HOOC—$CH_2$—O—$CH_2$—COOH |
| Gl | Glutaric Acid | HOOC—$CH_2$—$CH_2$—$CH_2$—COOH |

FIG. 1A

| Symbol | Name | Structure |
|---|---|---|
| Mal | Maleic Acid | 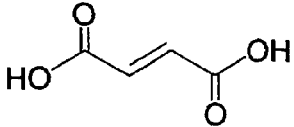 |
| NAA | 3-Amino-4,4-diphenylbutyric Acid | 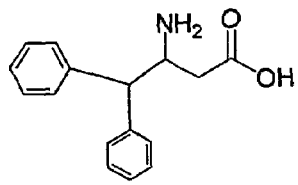 |
| Nal | 2-Naphthylalanine | 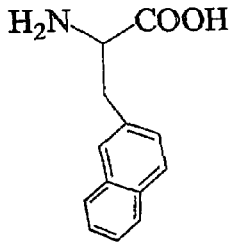 |
| Naph | 1,8-Naphthalene dicarboxylic Acid | 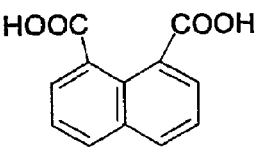 |
| PEG | Polyethylene Glycol$_{5000}$ Hemisuccinyl Ester | 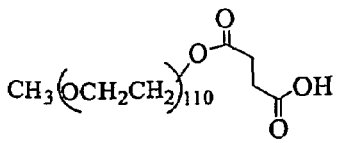 |
FIG. 1B

| Symbol | Name | Structure |
|---|---|---|
| Pyg | Pyroglutamic Acid | 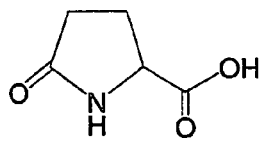 |
| Pyr | 3-Pyridylalanine | 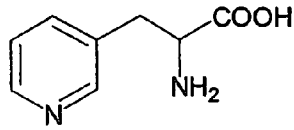 |
| Suc | Succinic Acid | 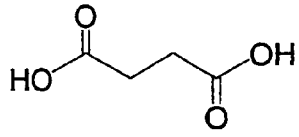 |
| Thi | 2-Thienylalanine | 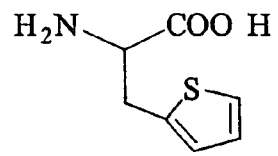 |
| Thz | 3-Thioproline or Thiazolidine-4-carboxylic Acid | 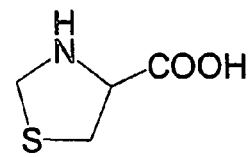 |
FIG. 1C

| Symbol | Name | Structure |
|---|---|---|
| Tic | Tetrahydroisoquinoline-3-carboxylic Acid | 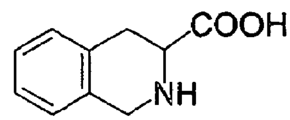 |

| No: | (AA₄) | (AA₃) | (AA₂) | (AA₁) | SEQ ID NO: |
|---|---|---|---|---|---|
| 1 | βAla | Ile | Ala | Phe | SEQ ID NO: 1 |
| 2 | βAla | Ile | Ala | Ile | SEQ ID NO: 2 |
| 3 | Tic | Ile | Ala | Leu | SEQ ID NO: 3 |
| 4 | Thi | Ile | Ala | Leu | SEQ ID NO: 4 |
| 5 | Nal | Ile | Ala | Leu | SEQ ID NO: 5 |
| 6 | Amb | Ile | Ala | Leu | SEQ ID NO: 6 |
| 7 | Aib | Ile | Ala | Leu | SEQ ID NO: 7 |
| 8 | βAla | Ile | Ala | Leu | SEQ ID NO: 8 |
| 9 | Thi | Ile | Aib | Leu | SEQ ID NO: 9 |
| 10 | Nal | Ile | Aib | Leu | SEQ ID NO: 10 |
| 11 | βAla | Ile | Aib | Leu | SEQ ID NO: 11 |
| 12 | Amb | Ile | Aib | Leu | SEQ ID NO: 12 |
| 13 | Aib | Ile | Aib | Leu | SEQ ID NO: 13 |
| 14 | βAla | Ile | Gly | Phe | SEQ ID NO: 14 |
| 15 | βAla | Ile | Gly | Ile | SEQ ID NO: 15 |
| 16 | Tic | Ile | Gly | Leu | SEQ ID NO: 16 |
| 17 | Thi | Ile | Gly | Leu | SEQ ID NO: 17 |
| 18 | Nal | Ile | Gly | Leu | SEQ ID NO: 18 |
| 19 | βAla | Ile | Gly | Leu | SEQ ID NO: 19 |
| 20 | Amb | Ile | Gly | Leu | SEQ ID NO: 20 |
| 21 | Aib | Ile | Gly | Leu | SEQ ID NO: 21 |
| 22 | βAla | Ile | Thr | Ile | SEQ ID NO: 22 |
| 23 | βAla | Ile | Tyr | Ile | SEQ ID NO: 23 |
| 24 | βAla | Ile | Ala | Gly | SEQ ID NO: 24 |
| 25 | Ø | Ile | Ala | Leu | SEQ ID NO: 25 |
| 26 | Ø | Ile | N(Me)Ala | Leu | SEQ ID NO: 26 |
| 27 | Ø | Ile | Ala | Phe | SEQ ID NO: 27 |
| 28 | Ø | Ile | Ala | Ile | SEQ ID NO: 28 |
| 29 | Ø | Ile | Aib | Leu | SEQ ID NO: 29 |
| 30 | Ø | Ile | Gly | Phe | SEQ ID NO: 30 |
| 31 | Ø | Ile | Gly | Ile | SEQ ID NO: 31 |
| 32 | Ø | Ile | Gly | Leu | SEQ ID NO: 32 |
| 33 | Ø | Ile | Thr | Ile | SEQ ID NO: 33 |
| 34 | Ø | Ile | Ala | Gly | SEQ ID NO: 34 |
| 35 | βAla | Ile | Tyr | Leu | SEQ ID NO: 35 |
| 36 | βAla | Ile | Tyr | Gly | SEQ ID NO: 36 |

Ø = not present

FIG. 10

PRODRUG COMPOUNDS WITH AN ISOLEUCINE

CROSS REFERENCE TO RELATED APPLICATION

This application claims the benefit under 35 U.S.C. 119(e) of U.S. Ser. No. 60/211,686, filed Jun. 14, 2000.

INTRODUCTION

1. Technical Field

The present invention is directed to new compounds useful as prodrugs. Such prodrugs may be used for treating disease, especially tumors, in patients.

2. Background

Many therapeutic agents, such as anthracyclines and vinca alkaloids, are especially effective for the treatment of cancers. However, these molecules are often characterized in vivo by an acute toxicity, especially a bone marrow and mucosal toxicity, as well as a chronic cardiac toxicity in the case of the anthracyclines and chronic neurological toxicity in the case of the vinca alkaloids. Similarly, methotrexate may be used for the treatment of inflammatory reactions, such as rheumatic diseases, but its high toxicity limits its applications. Development of more specific and safer anti-tumor agents is desirable for greater effectiveness against tumor cells and a decrease in the number and severity of the side effects of these products (toxicity, destruction of non-tumor cells, etc.). Development of more specific anti-inflammatory agents is also desirable.

In order to minimize toxicity problems, therapeutic agents are advantageously presented to patients in the form of prodrugs. Prodrugs are molecules capable of being converted to drugs (active therapeutic compounds) in vivo by certain chemical or enzymatic modifications of their structure. For purposes of reducing toxicity, this conversion should be confined to the site of action or target tissue rather than the circulatory system or non-target tissue. Prodrugs are often characterized by a low stability in blood and serum, however. This is due to the presence of enzymes in blood and serum that degrade, and consequently may activate, the prodrugs before the prodrugs can reach the desired sites within the patient's body.

A desirable class of prodrugs that overcomes such problems have been disclosed in Patent Cooperation Treaty International Publication No. WO 96/05863 and in U.S. Pat. No. 5,962,216, both incorporated herein by reference. Further useful prodrug compounds and methods of making such prodrugs are desirable, however, as are methods of making the prodrugs.

Prodrugs that display a high specificity of action, a reduced toxicity, and an improved stability in blood especially relative to prodrugs of similar structure that have existed in the public domain are particularly desirable.

SUMMARY OF THE INVENTION

The compound of the invention is a prodrug form of a therapeutic agent, in which the therapeutic agent is linked directly or indirectly to an oligopeptide, which in turn, is linked to a stabilizing group. The oligopeptide has an isoleucine residue in the third amino acid position counted from the C-terminus (per the typical orientation of the prodrug). The prodrugs of the invention display a high specificity of action, a reduced toxicity, an improved stability in the serum and blood, and do not move into target cells, or do so only minimally, until activated by a target cell associated enzyme.

The present invention also relates to the pharmaceutical composition comprising the compound according to the invention and optionally a pharmaceutically acceptable carrier, adjuvant, vehicle or the like. Articles of manufacture, such as kits for diagnosis or assay are also described.

Further, methods of designing prodrugs and of decreasing toxicity an improving safety index by modifying a therapeutic agent to create a prodrug are disclosed. Such modification provides an improved therapeutic index as compared to the free therapeutic agent.

The present invention further includes methods of treating a medical condition by administering the prodrug of the invention.

Several processes for making the prodrugs are included, as well.

BRIEF DESCRIPTION OF THE DRAWINGS

FIGS. 1A–1D are a table of abbreviations, names, and structures.

FIG. 10 is a table of oligopeptides useful in the prodrug of the invention.

DETAILED DESCRIPTION

Figure 1D:
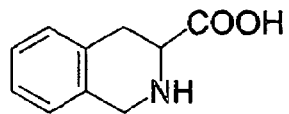

Abbreviations
ACN=Acetonitrile
Aib=Aminoisobutyric acid
All=Allyl
Aloc=Allyloxycarbonyl
Amb=4-(Aminomethyl)benzoic acid
APP=3-Amino-3-phenylpropionic acid
DCC=N,N'-Dicyclohexylcarbodiimide
Boc=t-butyloxycarbonyl
Cap=amino caproic acid
DBN=1,5 Diazabicyclo [4.3.0] non-5-ene
DBO=1,4 Diazabicyclo [2.2.2] octane
DBU=1,8-Diazabicyclo [5.4.0] undec-7-ene
DCM=Dichloromethane
DIC=N,N'-Diisopropylcarbodiimide
DIEA=Diisopropylethylamine
Dg=Diglycolic Acid
DMF=Dimethylformamide
Dnr=Daunorubicin
Dox=Doxorubicin
Et$_2$O=diethyl ether
Fmoc=9-Fluorenylmethyloxycarbonyl
Gl=Glutaric Acid
HATU=O-(7-Azabenzotriazol-1-yl)-1,1,3,3-tetramethyluronium-hexafluorophosphate
HBTU=2-(1H-Benzotriazole-1-yl)1,1,3,3-tetramethyluronium-hexafluorophosphate
HEPES—Hydroxethylpiperidine
HOBt=N-Hydroxybenzotriazole
HPLC=High pressure liquid chromatography
MeOH=Methanol
MeOSuc=Methyl hemisuccinyl/Methyl hemisuccinate
MTD=Maximum tolerated dose
NAA=3-Amino-4,4-diphenylbutyric Acid
Nal=2-Naphthylalanine
Naph=1,8-Naphthalene dicarboxylic acid
Nle=Norleucine
NMP=N-methylpyrrolidine
Nva=Norvaline
PAM resin=4-hydroxymethylphenylacetamidomethyl
Pyg=Pyroglutamic acid
Pyr=3-Pyridylalanine
RT, rt=Room temperature
Suc=Succinic Acid/Succinyl
TCE=trichloroethyl
TFA=Trifluoroacetic acid
THF=Tetrahydrofuran
Thi=2-Thienylalanine
Thz=Thiazolidine-4-carboxylic acid
Tic=Tetrahydroisoquinoline-3-carboxylic acid
TOP=Thimet oligopeptidase The invention includes compounds that may be described as prodrug forms of therapeutic agents. The therapeutic agent is linked directly or indirectly to an oligopeptide, which in turn, is linked to a stabilizing group. A linker group between the therapeutic agent and the oligopeptide may optionally be present. The oligopeptide is three or four amino acids in length and is characterized, in the typical orientation of the prodrug, by having an isoleucine residue in the third amino acid from its C-terminus.

Prodrug

The prodrug of the invention is a modified form of a therapeutic agent and comprises several portions, including:
(1) a therapeutic agent,
(2) an oligopeptide, and
(3) a stabilizing group, and
(4) optionally, a linker group.

Each of the portions of the prodrug are discussed in greater detail below. The typical orientation of these portions of the prodrug is as follows:

(stabilizing group)-(oligopeptide)-(optional linker group)-(therapeutic agent).

The stabilizing group is directly linked to the oligopeptide at a first attachment site of the oligopeptide. The oligopeptide is directly or indirectly linked to the therapeutic agent at a second attachment site of the oligopeptide. If the oligopeptide and the therapeutic agent are indirectly linked, then a linker group is present.

Direct linkage of two portions of the prodrug means a covalent bond exists between the two portions. The stabilizing group and the oligopeptide are therefore directly linked via a covalent chemical bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Thus, typically, the oligopeptide is covalently bound to the linker group which, in turn, is covalently bound to the therapeutic agent.

The prodrug of the invention is typically cleavable within its oligopeptide portion. In order for the prodrug to be effective, the prodrug typically undergoes in vivo modification producing a portion of the prodrug that is able to enter the target cell. A first cleavage within the oligopeptide portion of the prodrug may leave an active portion of the prodrug, i.e., a portion of the prodrug that is competent for transport into the target cell, as one of the cleavage products. Alternatively, further cleavage by one or more peptidases may be required to result in a transport-competent portion of the prodrug. The active or transport-competent portion of the prodrug has at least the therapeutic agent and is that part of the prodrug that can enter the target cell to exert a therapeutic effect directly or upon further conversion within the target cell.

Thus, the compound has an active portion, and the active portion is more capable of entering the target cell after cleavage by an enzyme associated with a target cell than prior to such cleavage. The structures of the stabilizing group and oligopeptide are selected to limit clearance and metabolism of the prodrug by enzymes, which may be present in blood or non-target tissues and are further selected to limit transport of the prodrug into cells. The stabilizing group blocks cleavage of the prodrug by exopeptidase in vivo and, additionally, may act in providing preferable charge or other physical characteristics of the prodrug. The amino acid sequence of the oligopeptide is selected for resistance to cleavage by trouase, a class of enzymes associated with target cells and described in greater detail below. Both tetrapeptides and tripeptides may be used in the invention. In a preferred embodiment of the invention, the isoleucine-containing peptide is a tripeptide. Generally speaking, tripeptides are poorly cleaved in the systemic circulation and in normal tissues and therefore may have a higher therapeutic index as compared with a tetrapeptide of overlapping sequence.

It is desirable to make a therapeutic agent, especially an antitumor and/or anti-inflammatory therapeutic agent, inactive by modification of the therapeutic agent to a prodrug form. According to the invention, the target cells are usually tumor cells or cells, such as macrophages, neutrophils, and monocytes, participating in inflammatory reactions, especially those associated with rheumatic diseases. Modification of the therapeutic agent to a prodrug form also reduces some of the side effects of the therapeutic agents.

Figure 2:
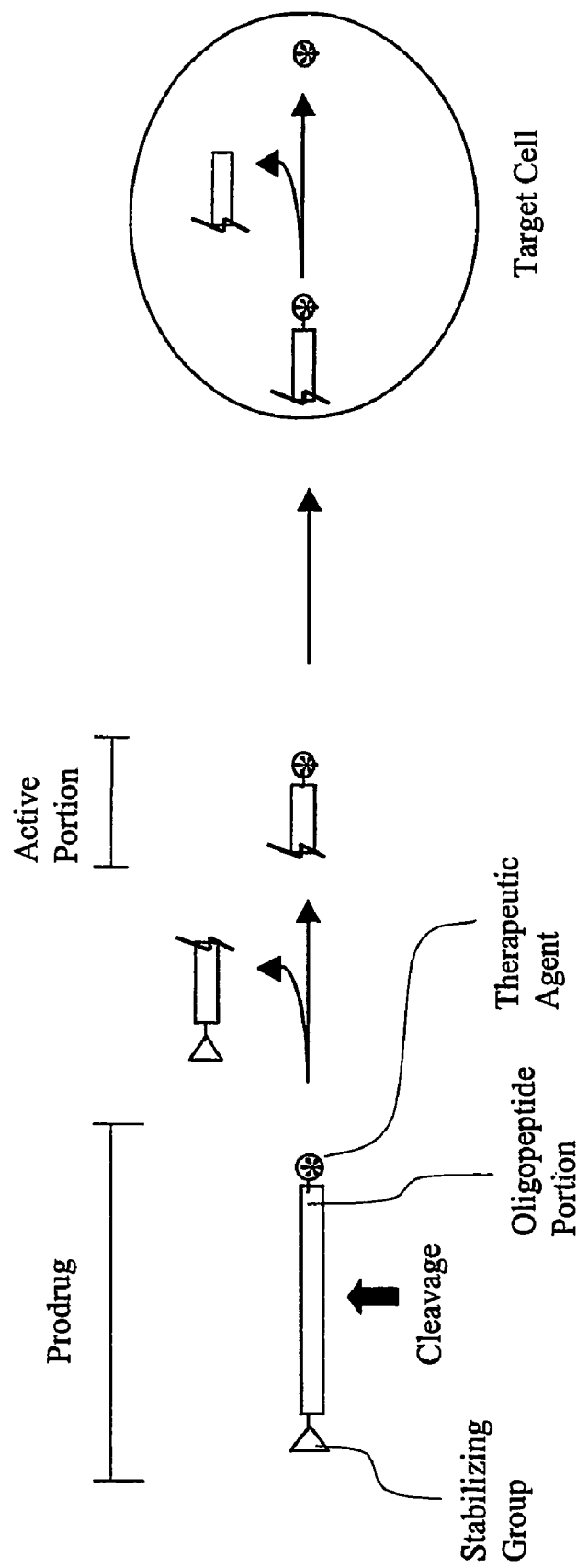
FIG. 2 is an exemplary scheme of cleavage of a prodrug of the invention in the extracellular vicinity of the target cell and within the target cell.

The prodrug is administered to the patient, carried through the blood stream in a stable form, and when in the vicinity of a target cell, is recognized and modified by a target cell associated enzyme. Since the enzyme activity is only minimally present within the extracellular vicinity of normal cells, the prodrug is not activated and its transport-competent portion (including the therapeutic agent) gains entry into the normal cells only minimally at best. In the vicinity of tumor or other target cells, however, the increased presence of the relevant enzyme in the local environment causes cleavage of the prodrug. After modification from the prodrug form and entry into the target cell, the therapeutic agent (optionally attached to one or more amino acids and possibly also a linker group) acts to kill or block proliferation of the target cell. The example shown in FIG. 2 depicts a typical prodrug being cleaved extracellularly and gaining entry into the target cell. Once within the target cell, it may be further modified to provide therapeutic effect. While a portion of the prodrug may occasionally gain access to and possibly harm normal cells, the transport-competent portion of the prodrug is freed primarily in the vicinity of target cells. Thus, toxicity to normal cells is minimized.

This process is particularly useful for, and is designed for, target cell destruction when the target tissue releases an enzyme that is not released by normal tissue or cells. Here "normal cells" means non-target cells that would be encountered by the prodrug upon administration of the prodrug in the manner appropriate for its intended use.

In an alternative embodiment, the orientation of the prodrug may be reversed so that a stabilizing group is attached to the oligopeptide at the C-terminus and the therapeutic agent is directly or indirectly linked to the N-terminus of the oligopeptide. Thus, in an alternative embodiment, the first attachment site of the oligopeptide may be the C-terminus of the oligopeptide and the second attachment site by the oligopeptide may be the N-terminus of the oligopeptide. The linker group may optimally be present between the therapeutic agent and the oligopeptide. The alternative embodiment of the prodrug of the invention functions in the same manner as does the primary embodiment.

It was expected that oligopeptide sequences having isoleucine in the $AA^3$ position (per the numbering scheme described below) would not make good candidates for prodrugs due to the preferential cleavage by trouase of oligopeptides having a non-isoleucine residue in the $AA^3$ position. However, when isoleucine-containing prodrug compounds, as described herein, were tested in vivo, the surprising discovery was that such compounds did indeed serve as useful prodrugs.

Compounds of the invention are good prodrugs because they show high stability, i.e., a low level of release of the active therapeutic agent, in the systemic circulation and in normal tissues. Peptides of the invention are not activated in the blood or normal tissues to any great extent, yet are activated at tumor sites.

Consequently, they have an improved therapeutic index, improved toxicological profile and favorable pharmacokinetics.

Without limitation to a particular theory, it is believed that such isoleucine-containing prodrugs are activated in the vicinity of the target cells by an enzyme other than a trouase-type enzyme. Thus, creation of such isoleucine-containing prodrugs represents an alternative method of prodrug design to that presented in PCT/US99/30393.

As described herein, a compound of the invention comprises:
 (1) a therapeutic agent capable of entering a target cell,
 (2) an oligopeptide of the formula $(AA)_n$-$AA^3$-$AA^2$-$AA^1$, wherein:
  each AA independently represents an amino acid,
  n is 0 or 1, and when n is 1, then $(AA)_n$ is $AA_4$ which represents any amino acid,
  $AA^3$ represents isoleucine,
  $AA^2$ represents any amino acid, and
  $AA^1$ represents any amino acid,
 (3) a stabilizing group, and
 (4) optionally, a linker group not cleavable by a trouase, such as TOP (described in greater detail below)
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the compound by enzymes present in whole blood, and wherein the compound is cleavable by an enzyme associated with the target cell, the enzyme associated with the target cell being other than TOP. The compound preferably includes an oligopeptide that is resistant to cleavage by a trouase, particularly TOP i.e., resistant to cleavage under physiological conditions. The optionally present linker group that is not cleavable by a trouase is not cleavable under physiological conditions.

For purposes of this discussion, a compound is resistant to cleavage by a given enzyme if the rate of cleavage by a purified preparation of the given enzyme is no more than 15%, preferably no more than 5%, and ideally no more than 1% of the rate of cleavage of Suc-βAla-Leu-Ala-Leu (SEQ ID NO:41) conjugated via the carboxyl terminus to the same therapeutic agent as the compound of interest. The rates should be compared under the same assay conditions.

A compound is cleavable by a given enzyme if greater than 10% per hour, preferably greater than 50% per hour, is cleaved by a mixture of the compound and the enzyme under experimental conditions which model physiological conditions, particularly those outside of the target cell. The concentration of the given enzyme in the experiment is representative of the concentration of the given enzyme in the extracellular milieu of the target tissue.

Target Cell Associated Enzymes

The prodrugs of the invention are designed to take advantage of preferential activation, through interaction with an enzyme associated with the target cell, at or near the site targeted within the body of the patient. Although not believed to be responsible for cleavage of the compounds of the invention, one such type of enzyme, or class of enzymes, associated with likely target cells is trouase, described in greater detail in PCT/US99/30393. Trouase is believed to be a class of enzymes, of which Thimet oligopeptidase ("TOP") is one member. Trouases are highly discriminating in their selectivity and cleavage. Trouase is an endopeptidase that shows a remarkable degree of discrimination between leucine and isoleucine at the carboxyl side of the oligopeptide cleavage site. A defining characteristic is that under appropriate assay conditions, trouase readily cleaves succinyl-βAla-Leu-Ala-Leu-Daunorubicin (SEQ ID NO:42) while it is at least twenty-fold less active with succinyl-βAla-Ile-Ala-Leu-Daunorubicin (SEQ ID NO:43).

Although knowledge of the sequences cleaved by trouase may be utilized for designing therapeutically useful prodrugs, the previously less-favored isoleucine-containing peptide sequences represent an unexpectedly useful alternative for designing prodrugs. The presence of isoleucine at the P1 cleavage site of trouase (which would be equivalent to the $AA^3$ position in the typical oligopeptides described herein) has been shown to prevent or greatly minimize cleavage of the peptide by trouase. Such inhibition was shown both in vitro using partially purified trouase and purified TOP and in vivo in metabolic studies with normal mice.

The enzyme involved in the activation of the prodrugs of the invention is believed to be associated with target cells, but is found in the circulation only at very low levels. Most likely it is generated either by the target cells themselves or by normal cells that are associated with the target cells, such as stromal cells, neutrophils, or macrophages, or B cells. So, for example, the target cell associated enzyme may be associated with or bound on (at least the active site) the outer cell surface, secreted, released, or present in some other manner in the extracellular vicinity of the target cell. In many cases, the prodrug of the invention includes a therapeutic agent for the treatment of cancer and the target cell is a tumor cell. Thus, the enzyme may be secreted extracellularly by the tumor cell or it may be present extracellularly because there is a fair amount of cell lysis associated with tumors generally.

Despite lack of cleavage by trouase and especially the TOP enzyme, in vivo studies have shown that compounds with isoleucine in what would be the trouase P1 cleavage position are effective in reducing the tumor growth rate and extending survival of nude mice implanted with human tumor xenografts. This finding indicates that one or more enzymes are present in tumor-bearing animals which can cleave isoleucine-containing prodrug compounds to initiate a process eventually leading to release of the active portion of the therapeutic agent, usually a cytotoxic agent, within the tumor or other target cells. The enzyme or enzymes that cleave isoleucine-containing peptides may be even more tumor-specific than TOP, which is present in a wide variety of normal cells and cell types as well as human cancer cells. Thus, designing of prodrugs having an isoleucine at an important position within the oligopeptide portion of the prodrug may be preferable to previously disclosed compounds that are cleavable by trouase and/or TOP.

Stabilizing Group

An important portion of the prodrug is the stabilizing group, which serves to protect the prodrug compound from cleavage in circulating blood when it is administered to the patient and allows the prodrug to reach the vicinity of the target cell relatively intact. The stabilizing group typically protects the prodrug from cleavage by proteinases and peptidases present in blood, blood serum, and normal tissue. Particularly, since the stabilizing group caps the N-terminus of the oligopeptide, and is therefore sometimes referred to as an N-cap or N-block, it serves to ward against peptidases to which the prodrug may otherwise be susceptible.

Ideally, the stabilizing group is useful in the prodrug of the invention if it serves to protect the prodrug from degradation, i.e., cleavage, when tested by storage of the prodrug compound in human blood at 37° C. for 2 hours and results in less than 20%, preferably less than 2%, cleavage of the prodrug by the enzymes present in the human blood under the given assay conditions. Thus, a fully formed conjugate may be tested to see if it is stable in whole blood.

More particularly, a stabilizing group that hinders cleavage of the oligopeptide by enzymes present in whole blood is advantageously chosen from the following:

(1) other than an amino acid, or (2) an amino acid that is either (i) a non-genetically-encoded amino acid or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with succinic acid and adipic acid being most preferred. Other examples of useful N-caps in the prodrug compound of the invention include diglycolic acid, fumaric acid, naphthalene dicarboxylic acid, pyroglutamic acid, acetic acid, 1- or 2-, naphthylcarboxylic acid, 1,8-naphthyl dicarboxylic acid, aconitic acid, carboxycinnamic acid, triazole dicarboxylic acid, gluconic acid, 4-carboxyphenyl boronic acid, a $(PEG)_n$-analog such as polyethylene glycolic acid, butane disulfonic acid, maleic acid, nipecotic acid, and isonipecotic acid.

Further, a non-genetically encoded amino acid such as one of the following may also be used as the stabilizing group: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

Additionally, in some experiments intravascular administration of an aggregating positively charged prodrug in mice resulted in acute toxicity. However, no such toxicity was observed when the charge on this prodrug was reversed by derivitization with a negatively charged stabilizing group.

Many cytotoxic compounds inherently have low solubility. Positively charged anthracyclines for example may form aggregates at high concentration and these aggregates may induce intravenous coagulation when the aggregates are administered intravenously. Since many oligopeptides have exposed, positively-charged amino termini at physiological pH, these aggregates may form a poly positively charged surface in vivo and induce a coagulation cascade within a few minutes of administration. This has the potential for rendering any positively charged prodrugs that form aggregates unsuitable for therapeutic use.

As described in greater detail in PCT/US99/30393, one way of addressing such a potentially dangerous obstacle is to utilize the stabilizing group on the peptide chain N-terminus of a negatively charged or a neutral functionality. For example, the use of succinyl as a stabilizing group on the prodrug alleviates the prodrug's acute toxicity. It is believed that the stabilizing group reduces interaction between the compound and endothelial cells that line blood vessels. This solves an important problem in the use of peptide prodrugs as practical therapies for intravenous use in humans.

Oligopeptide

Oligopeptides are generally defined as polypeptides of short length, typically twenty amino acids or fewer. An oligopeptide useful in the prodrug of the invention is three or four amino acids in length. However, oligopeptides of greater length are also possible.

Numbering Scheme

According to the invention, the oligopeptide portion of the prodrug has a formula $(AA)_n$-$AA^3$-$AA^2$-$AA^1$, wherein:
each AA independently represents an amino acid,
n is 0 or 1, and when n is 1, then $(AA)_n$ is $AA^4$ which represents any amino acid,
$AA^3$ represents isoleucine,
$AA^2$ represents any amino acid, and
$AA^1$ represents any amino acid.

The oligopeptide is written in the conventional manner with the carboxyl terminus at the right and the amino terminus at the left. It is believed that the enzyme associated with the target cell cleaves the linkage between $AA^1$ and $AA^2$ of the oligopeptide. Unless otherwise indicated, all amino acids are in the L configuration. Although any amino acids may be present in the oligopeptide portion of the prodrug, with the exception of the amino acid at $AA^3$, which is always isoleucine, certain amino acids are preferred.

In the $AA^4$ position of the oligopeptide portion, a non-genetically encoded amino acid, for example, one of the following amino acids, is most preferably present: β-Alanine, Thiazolidine-4-carboxylic acid, 2-Thienylalanine, 2-Naphthylalanine, Alanine, D-Alanine, D-Leucine, D-Methionine, D-Phenylalanine, 3-Amino-3-phenylpropionic acid, 3-amino-4,4-diphenylbutyric acid, or Proline. Also possible are Aminoisobutyric acid, 4-Aminomethylbenzoic acid, or Tetrahydroisoquinoline-3-carboxylic acid in the $AA^4$ position.

$AA^3$ of the oligopeptide portion of the prodrug of the invention is isoleucine.

Most preferably, in the $AA^2$ position of the oligopeptide portion of the prodrug is one of the following amino acids: Alanine, Leucine, Glycine, Serine, Tyrosine, 3-Pyridylalanine, 2-Thienylalanine, or N-Methyl-alanine. The amino acid in the $AA^2$ position may also be selected from Aminoisobutyric Acid, Threonine, or Phenylalanine.

The amino acid present in the $AA^1$ position is most preferably selected from one of the following: Leucine, Phenylalanine, Isoleucine, Alanine, Glycine, Tyrosine, 2-Naphthylalanine, Serine, or Proline. Also preferred in the $AA^1$ position is β-Alanine.

Oligopeptides useful in the prodrug of the invention include those shown in FIG. 10, particularly βAla-Ile-Ala-Phe (SEQ ID NO: 1); βAla-Ile-Ala-Ile (SEQ ID NO: 2); Tic-Ile-Ala-Leu (SEQ ID NO: 3); Thi-Ile-Ala-Leu (SEQ ID NO: 4); Nal-Ile-Ala-Leu (SEQ ID NO: 5); Amb-Ile-Ala-Leu (SEQ ID NO: 6); Aib-Ile-Ala-Leu (SEQ ID NO: 7); βAla-Ile-Ala-Leu (SEQ ID NO: 8); Thi-Ile-Aib-Leu (SEQ ID NO: 9); Nal-Ile-Aib-Leu (SEQ ID NO: 10); βAla-Ile-Aib-Leu (SEQ ID NO: 11); Amb-Ile-Aib-Leu (SEQ ID NO: 12); Aib-Ile-Aib-Leu (SEQ ID NO: 13); βAla-Ile-Gly-Phe (SEQ ID NO: 14); βAla-Ile-Gly-Ile (SEQ ID NO: 15); Tic-Ile-Gly-Leu (SEQ ID NO: 16); Thi-Ile-Gly-Leu (SEQ ID NO: 17); Nal-Ile-Gly-Leu (SEQ ID NO: 18); βAla-Ile-Gly-Leu (SEQ ID NO: 19); Amb-Ile-Gly-Leu (SEQ ID NO: 20); Aib-Ile-Gly-Leu (SEQ ID NO: 21); βAla-Ile-Thr-Ile (SEQ ID NO: 22); βAla-Ile-Tyr-Ile (SEQ ID NO: 23), and βAla-Ile-Ala-Gly (SEQ ID NO: 24). Preferred tripeptide sequences for the invention include Ile-Ala-Leu (SEQ ID NO: 25); Ile-N(Me)Ala-Leu (SEQ ID NO: 26); Ile-Ala-Phe (SEQ ID NO: 27); Ile-Ala-Ile (SEQ ID NO: 28); Ile-Aib-Leu (SEQ ID NO: 29); Ile-Gly-Phe (SEQ ID NO: 30); Ile-Gly-Ile (SEQ ID NO: 31); Ile-Gly-Leu (SEQ ID NO: 32); Ile-Thr-Ile (SEQ ID NO: 33); and Ile-Ala-Gly (SEQ ID NO: 34); βAla-Ile-Tyr-Leu (SEQ ID NO: 35); and βAla-Ile-Tyr-Gly (SEQ ID NO: 36).

Therapeutic Agents

Therapeutic agents that are particularly advantageous to modify to a prodrug form are those with a narrow therapeutic window. A drug or therapeutic agent with a narrow therapeutic window is one in which the dose at which toxicity is evident, by general medical standards, is very close to the dose at which efficacy is evident.

The therapeutic agent conjugated to the stabilizing group and oligopeptide and, optionally, the linker group to form the prodrug of the invention may be useful for treatment of cancer, inflammatory disease, or some other medical condition. Preferably, the therapeutic agent is selected from the following classes of compounds: Alkylating Agents, Antiproliferative agents, Tubulin Binding agents, Vinca Alkaloids, Enediynes, Podophyllotoxins or Podophyllotoxin derivatives, the Pteridine family of drugs, Taxanes, Anthracyclines, Dolastatins, Topoisomerase inhibitors, Platinum-coordination-complex chemotherapeutic agents, Maytansinoids.

Particularly, the therapeutic agent is advantageously selected from the following compounds, or a derivative or analog thereof: Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin $A_4$ Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine Arabinoside, Colchicine, Cisplatin, Carboplatin, Mitomycin C, Bleomycin, Melphalan, chloroquine, cyclosporin A, and Maytansine. By derivative is intended a compound that results from reacting the named compound with another chemical moiety, and includes a pharmaceutically acceptable salt, acid, base or ester of the named compound. By analog is intended a compound having similar structural and functional properties, such as biological activities, to the named compound.

Linker Groups

A linker group between the oligopeptide and the therapeutic agent may be advantageous for reasons such as the following:

1. As a spacer for steric considerations in order to facilitate enzymatic release of the $AA^1$ amino acid or other enzymatic activation steps.

2. To provide an appropriate attachment chemistry between the therapeutic agent and the oligopeptide.
3. To improve the synthetic process of making the prodrug conjugate (e.g., by pre-derivitizing the therapeutic agent or oligopeptide with the linker group before conjugation to enhance yield or specificity.)
4. To improve physical properties of the prodrug.
5. To provide an additional mechanism for intracellular release of the drug.

Linker structures are dictated by the required functionality. Examples of potential linker chemistries are hydrazide, ester, ether, and sulfhydryl. Amino caproic acid is an example of a bifunctional linker group. When amino caproic acid is used as part of the linker group, it is not counted as an amino acid in the numbering scheme of the oligopeptide.

The optionally present linker group is not cleavable by TOP, i.e. it is not cleavable by TOP under physiological conditions.

Prodrug Design

A method of designing a prodrug is another aspect of the invention and entails initially identifying an oligopeptide as described above. Then the oligopeptide is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by TOP. Test compounds resistant to cleavage by TOP are selected. The resulting conjugate may also be tested for stability in whole blood. Test compounds stable in whole blood are selected.

The first attachment site is usually the N-terminus of the oligopeptide but may be the C-terminus of the oligopeptide or another part of the oligopeptide. The second attachment site is usually the C-terminus of the oligopeptide, but may be the N-terminus of the oligopeptide or another part of the oligopeptide. A prodrug designed by such a method is also part of the invention.

Further, the invention includes a method for decreasing toxicity of a therapeutic agent that is intended for administration to a patient. Specifically, a modified, prodrug form of the therapeutic agent is formed by directly or indirectly linking the therapeutic agent to an oligopeptide resistant to cleavage by a trouase, or more specifically, resistant to cleavage by TOP. The oligopeptide is also linked to a stabilizing group. The prodrug thus formed provides for decreased toxicity of the therapeutic agent when administered to the patient. The modification of the therapeutic agent in this manner also allows for administration of an increased dosage of the therapeutic agent to the patient relative to the dosage of the therapeutic agent in unconjugated form.

Pharmaceutical Compositions

The invention also includes a pharmaceutical composition comprising a compound, particularly a prodrug compound, according to the invention and, optionally, a pharmaceutically acceptable carrier, adjuvant, vehicle, or the like.

The invention also relates to the use of the pharmaceutical composition for the preparation of a medicinal product intended for the treatment of a medical condition.

The pharmaceutical composition may, for example, be administered to the patient parenterally, especially intravenously, intramuscularly, or intraperitoneally. Pharmaceutical compositions of the invention for parenteral administration comprise sterile, aqueous or nonaqueous solutions, suspensions, or emulsions. As a pharmaceutically acceptable solvent or vehicle, propylene glycol, polyethylene glycol, injectable organic esters, for example ethyl oleate, or cyclodextrins may be employed. Isotonic saline may be part of the pharmaceutical composition. Isotonic saline may be part of the pharmaceutical composition. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions that may be dissolved at the time of use in sterile water or any other sterile injectable medium.

The pharmaceutical composition may also comprise adjuvants which are well known in the art (e.g., vitamin C, malic acid, antioxidant agents, etc.) and capable of being used in combination with the compound of the invention in order to improve and prolong the treatment of the medical condition for which they are administered.

Doses for administration to a patient of the compounds according to the invention are generally at least the usual doses of the therapeutic agents known in the field, described in Bruce A. Chabner and Jerry M. Collins, *Cancer Chemotherapy*, Lippincott Ed., ISBN 0-397-50900-6 (1990) or they may be adjusted, within the judgment of the treating physician, to accommodate the superior effectiveness of the prodrug formulations or the particular circumstances of the patient being treated. Hence, the doses administered vary in accordance with the therapeutic agent used for the preparation of the compound according to the invention.

Treatment with Prodrug Compound

A method for the therapeutic treatment of a medical condition that involves administering, preferably parenterally and more preferably intravenously, to the patient a therapeutically effective dose of the pharmaceutical composition is also within the scope of the invention. Thus, a method for treating a patient includes administering to the patient a therapeutically effective amount of a compound comprising:

(1) a therapeutic agent capable of entering a target cell,
(2) an oligopeptide of the formula $(AA)_n$-$AA^3$-$AA^2$-$AA^1$, wherein:
  each AA independently represents an amino acid,
  n is 0 or 1, and when n is 1, then $(AA)_n$ is $AA^4$ which represents any amino acid,
  $AA^3$ represents isoleucine,
  $AA^2$ represents any amino acid, and
  $AA^1$ represents any amino acid,
(3) a stabilizing group, and
(4) optionally, a linker group not cleavable by a trouase,
  wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
  wherein the stabilizing group hinders cleavage of the compound by enzymes present in whole blood, and
  wherein the compound is cleavable by an enzyme associated with the target cell, the enzyme being other than a trouase.

The prodrug compound is useful for the treatment of many medical conditions including cancer, neoplastic diseases, tumors, inflammatory diseases, and infectious diseases. Examples of preferred diseases are breast cancer, colorectal cancer, liver cancer, lung cancer, prostate cancer, ovarian cancer, brain cancer, and pancreatic cancer. Formulated in pharmaceutically acceptable vehicles (such as isotonic saline), the prodrug compound can be administered to animals or humans in intravenous doses ranging from 0.05 mg/kg/dose/day to 300 mg/kg/dose/day. It can also be administered via intravenous drip or other slow infusion method.

Human patients are the usual recipients of the prodrug of the invention, although veterinary usage is also contemplated.

Diagnosis or Assay

An article of manufacture, such as a kit, for diagnosis or assay is also within the scope of the invention. Such an article of manufacture would preferably utilize a compound as described above, except that a marker, such as coumarin is conjugated to the oligopeptide and stabilizing group instead of a therapeutic agent. A marker intends any moiety that can be conjugated to the oligopeptide and is readily detectable by any method known in the art. At least one reagent useful in the detection of the marker is typically included as part of the kit. Thus, the article of manufacture would include the following:

(1) a compound comprising:
  (a) a marker,
  (b) an oligopeptide of the formula $(AA)_n$-$AA^3$-$AA^2$-$AA^1$, wherein:
    each AA independently represents an amino acid,
    n is 0 or 1, and when n is 1, then $(AA)_n$ is $AA^4$ which represents any amino acid,
    $AA^3$ represents isoleucine,
    $AA^2$ represents any amino acid, and
    $AA^1$ represents any amino acid,
  (c) a stabilizing group, and
  (d) optionally, a linker group not cleavable by TOP,
    wherein the oligopeptide is directly linked to the stabilizing group at a first attachment site of the oligopeptide and the oligopeptide is directly linked to the marker or indirectly linked through the linker group to the marker at a second attachment site of the oligopeptide,
    wherein the stabilizing group hinders cleavage of the compound by enzymes present in whole blood, and
    wherein the compound is cleavable by an enzyme associated with the target cell, the enzyme associated with the target cell being other than TOP, and
(2) optionally at least one reagent useful in the detection of said marker.

The compound is preferably resistant to cleavage by a trouase, especially TOP. The article of manufacture may be used, for example, with patient samples to diagnose tumors or to identify patients susceptible to treatment by prodrug therapy.

Process Chemistry General Procedures

Oligopeptide: General Method for the Synthesis of Peptides

The peptide, or oligopeptide, sequences in the prodrug conjugates of this invention may be synthesized by the solid phase peptide synthesis (using either Boc or Fmoc chemistry) methods or by solution phase synthesis. The general Boc and Fmoc methods are widely used and are described in the following references: Merrifield, *J. A. Chem. Soc.*, 88:2149 (1963); Bodanszky and Bodanszky, *The Practice of Peptide Synthesis*, Springer-Verlag, Berlin, 7–161 (1994); Stewart, *Solid Phase Peptide Synthesis*, Pierce Chemical Rockford, (1984).

General Fmoc Solid Phase Method

Figure 3:
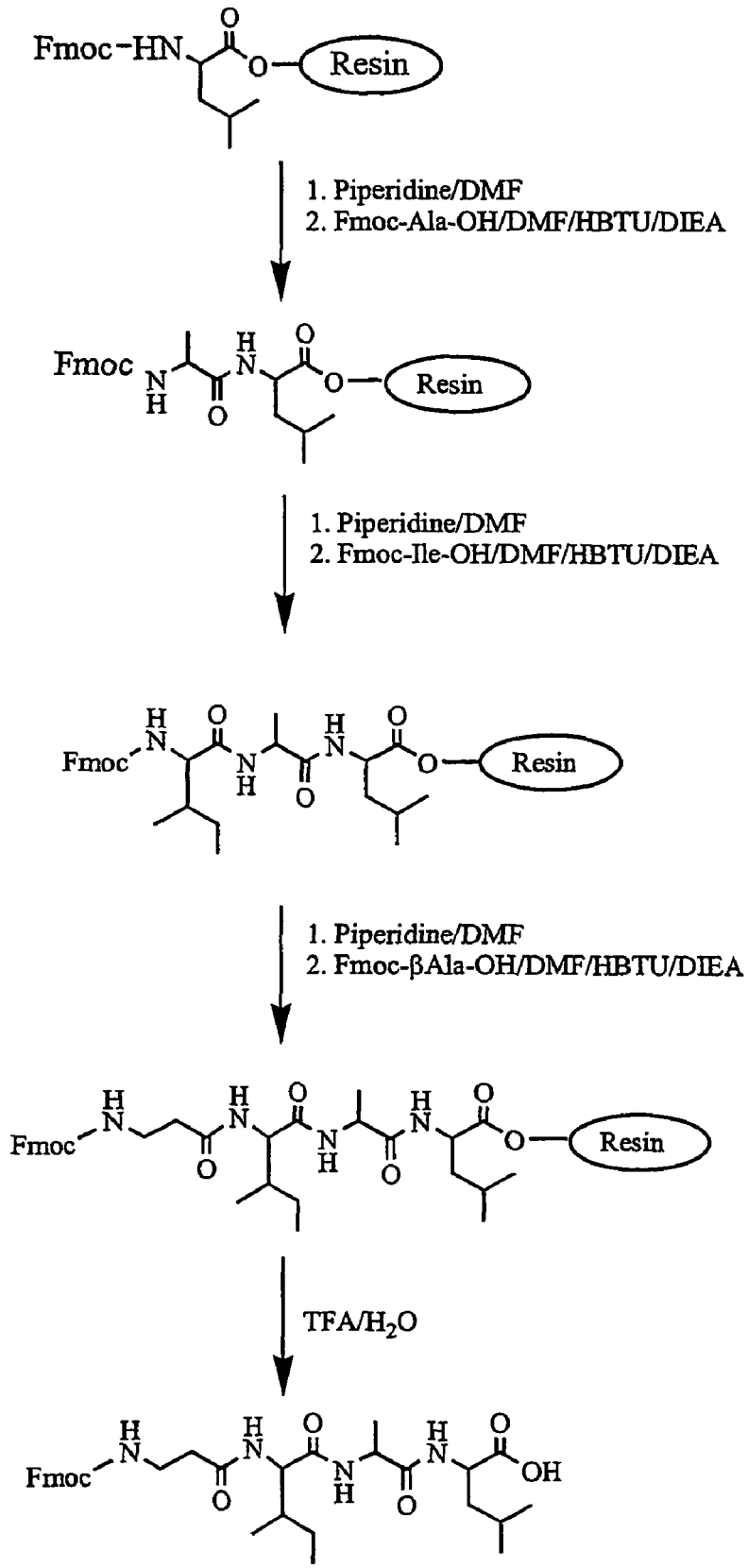
FIG. 3 illustrates a synthesis of Fmoc-βAla-Ile-Ala-Leu (SEQ ID NO:37), a typical intermediate of the invention.

Using the preferred solid phase synthesis method, either automated or manual, a peptide of desired length and sequence is synthesized through the stepwise addition of amino acids to a growing chain which is linked to a solid resin. Examples of useful Fmoc compatible resins include, but are not limited to, Wang resin, HMPA-PEGA resin, Rink acid resin, or a hydroxyethyl-photolinker resin. The C-terminus of the peptide chain is covalently linked to a polymeric resin and protected α-amino acids were added in a stepwise manner with a coupling reagent. A preferred α-amino protecting group is the Fmoc group, which is stable to coupling conditions and can readily be removed under mild alkaline conditions. The reaction solvents are preferably but not limited to DMF, NMP, DCM, MeOH, and EtOH. Examples of coupling agents are: DCC, DIC, HATU, and HBTU. Cleavage of the N-terminal protecting group is accomplished in 10–100% piperidine in DMF at 0–40° C., with ambient temperature being preferred. At the end of synthesis the final Fmoc protecting group is removed using the above N-terminal cleavage procedure. The remaining peptide on resin is cleaved from the resin along with any acid sensitive side chain protecting groups by treating the resin under acidic conditions. For example, an acidic cleavage condition is a mixture of trifluoroacetic acid (TFA) in dichloromethane. If the hydroxyethyl-photolinker resin is used, the appropriate wavelength for inducing cleavage is λ365 nm ultraviolet light. A diagrammatic representation of this process is given in FIG. 3.

General N-Cap Method via Solid Phase Synthesis

The preparation of N-terminus derivatized peptides is conveniently accomplished on solid phase. When the peptide synthesis is complete, the terminal Fmoc is removed while the peptide is still on the solid support. The N-cap of choice is coupled next using standard peptide coupling conditions onto the N-terminus of the peptide. On completion of the N-cap coupling the peptide is cleaved from the resin using the procedure described above if the Fmoc synthesis procedure is used.

General Boc Solid Phase Method

For the solid phase method using Boc chemistry, either the Merrifield resin or PAM resin is useful. The amino acids are coupled to the growing chain on solid phase by successive additions of coupling agent activated Boc-protected amino acids. Examples of coupling agents are: DCC, DIC, HATU, and HBTU. The reaction solvents may be DMF, DCM, MeOH, or NMP. Cleavage of the Boc protecting group is accomplished in 10–100% TFA in DCM at 0–40° C., with ambient temperature being preferred. On completion of the peptide chain assembly the N-terminus protecting group (usually Boc) is removed as described above. The peptide is removed from the resin using liquid HF or trifluoromethane sulfonic acid in dichloromethane.

General Procedure for the Preparation of Fmoc Oligopeptide by Solution Phase Synthesis Alternatively, the prodrug peptide intermediate may be made via a solution phase synthesis, utilizing either Boc or Fmoc chemistry. In the diagrammatic presentation of the methods (FIG. 4), the C-terminal Leu tetrapeptide is generally used as an example, but it will be understood that similar reactions may be performed with other C-terminal tetrapeptides, as well. The peptide can be built up by the stepwise assembly in analogy to the solid phase method (in the N-terminal direction or in the C-terminal direction) or through the coupling of two suitably protected dipeptides or a tripeptide with a single amino acid.

Figure 4:
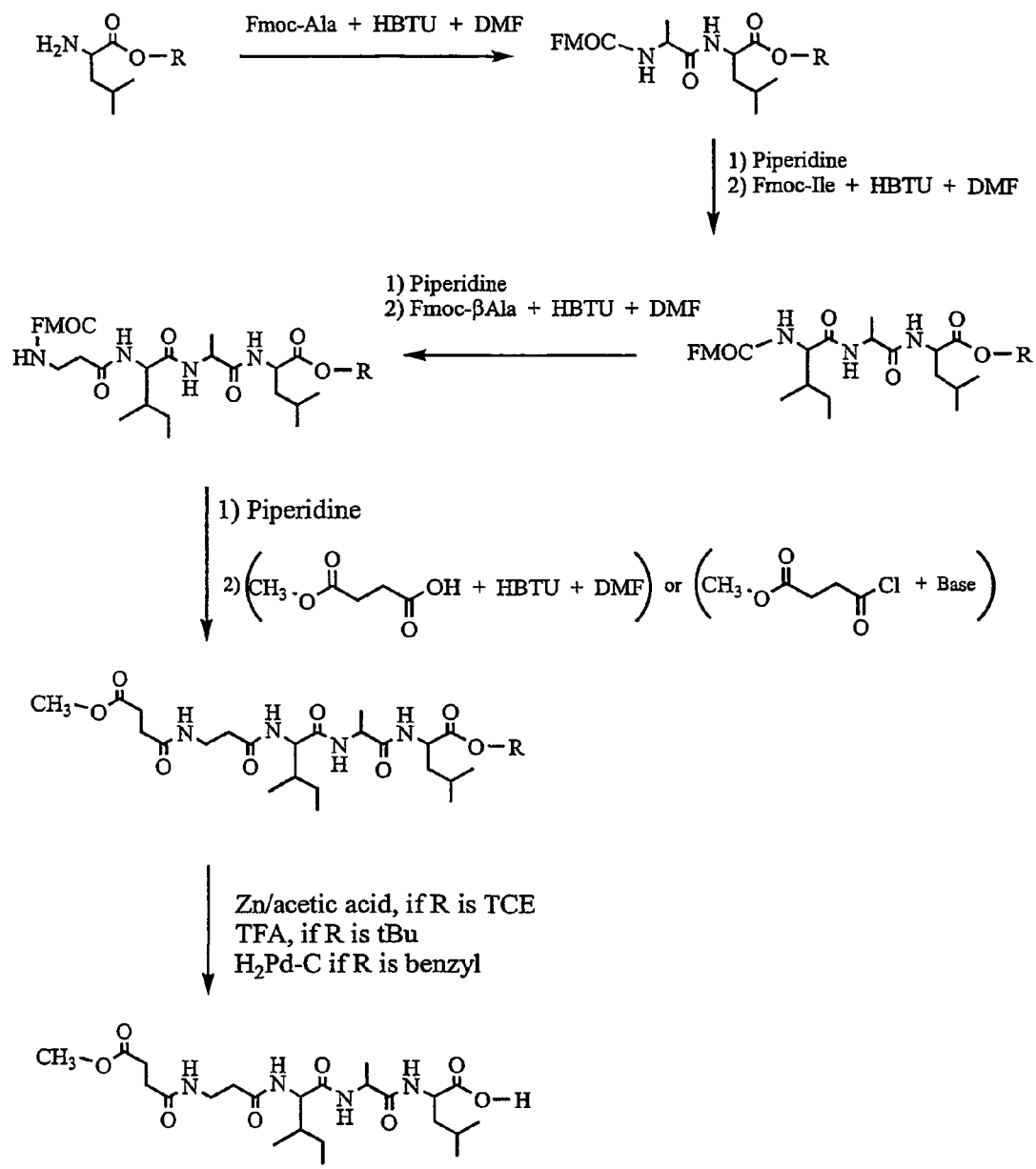
FIG. 4 illustrates an "Fmoc-route" synthesis of Methyl-succinyl-βAla-Ile-Ala-Leu (SEQ ID NO:38), a typical intermediate of FIG. 5 illustrates an "Fmoc route" synthesis of a salt form of Suc-βAla-Ile-Ala-Leu-Dox (SEQ ID NO:39), a typical compound of the invention.

One method of solution phase synthesis is a stepwise building up of the prodrug peptide intermediate using Fmoc chemistry, shown in FIG. 4. The C-terminus must be protected to reduce the formation of side products. The C-terminal R group in FIG. 4 is Me, tBu, benzyl or TCE. (Note that when the N-cap is methyl succinyl, the C-terminus R group cannot be Methyl.) Although DMF is given as the solvent, other solvents such as DMSO, CH$_3$CN, or NMP (or mixtures thereof) may be substituted therefor. Pyridine, Et$_3$N or other bases may be substituted for piperidine in deprotecting the growing peptide chain protected amino terminus. Similarly, although HBTU is given in the diagram above as the activating agent, other activating agents such as DCC, DIC, DCC+HOBt, OSu, activated esters, azide, or triphenyl phosphoryl azide may be used. Additionally, the protected peptide acid chloride or acid bromide may be used to couple directly to the amino acid or peptide fragment. On completion of the oligopeptide assembly, the N-terminus is deprotected and the C-terminus protected peptide is ready to accept the desired N-cap.

General Procedure for the Preparation of N-capped Oligopeptide via Solution Phase Synthesis When constructing the N-capped oligopeptide by solution phase synthesis, the N-cap needs to be synthesized by a slightly modified procedure (FIG. 4). First the C-terminus of the Fmoc oligopeptide needs to be protected with an acid labile or hydrogenation sensitive protecting group compatible with the selective deprotection of the C-terminus over the N-cap. Then the Fmoc protecting group needs to be removed from the oligopeptide to reveal the N-terminus. With the N-terminus deprotected and the C-terminus protected, the oligopeptide is reacted with the activated hemiester of the desired N-cap. The N-cap can be activated using methods for activating amino acids such as DCC or HATU in base and an appropriate solvent. Alternatively, where the methyl-hemisuccinate is used, the coupling may also be done via methyl hemisuccinyl chloride (or other acid halide) (FIG. 4) using an inert solvent in the presence of an organic or inorganic base, such as DIEA, triethylamine or Cs$_2$CO$_3$. One example of such a synthesis includes reacting methyl-hemisuccinate and βAla-Ile-Ala-Leu benzyl ester. The coupling method can be any one of the methods generally used in the art (see for example: Bodanszky, M., *The Practice of Peptide Synthesis*, Springer Verlag, 185 (1984); Bodanszky, M., *Principles of Peptide Synthesis*, Springer Verlag, 159 (1984). The benzyl group then can be removed by catalytic hydrogenation providing the desired N-cap methyl-succinyl form of oligopeptide no. 8. Other examples of suitable, selectively removable C-terminal protecting groups can be, but are not limited to, tBu, alkoxymethyl and TCE. Other methods of accomplishing this step are described in the literature.

Any combination of the above method can be considered, such as "fragment condensation" of di-, or tripeptides. The reaction conditions are well known in the art and detailed in the citations given. The advantage of the above described methods is the facile purification of the product produced by solution phase synthesis.

Prodrug Conjugate

General Methods for the Conjugation and Deprotection Steps

Figure 5:
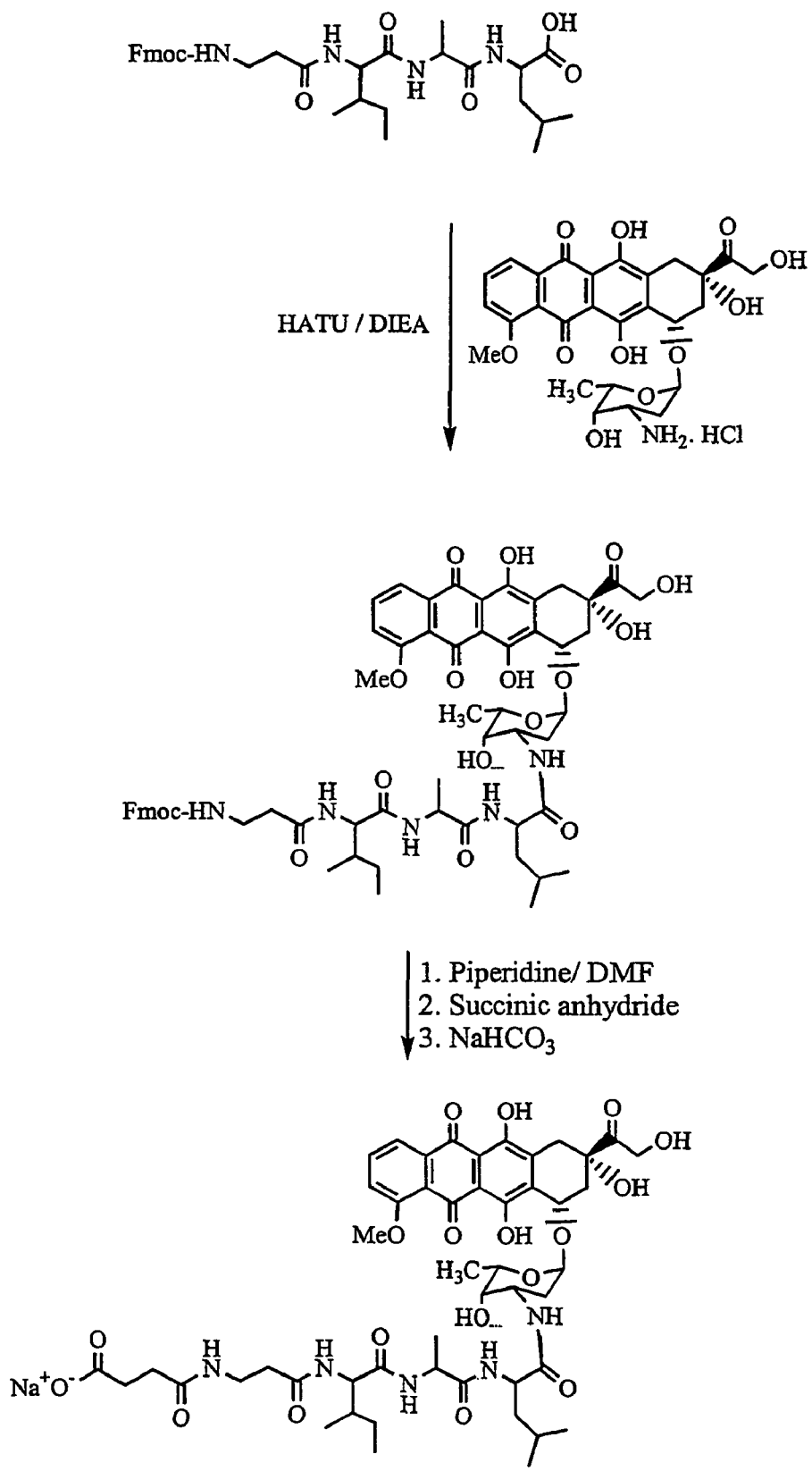

The N-cap form of the oligopeptide-therapeutic agent described in this invention can be synthesized by coupling an Fmoc form (which means Fmoc is attached to the N-terminus of the oligopeptide) of the oligopeptide with daunorubicin, doxorubicin, or any appropriate therapeutic agent using any of the standard activating reagents used in peptide synthesis (FIG. 5). The solvent may be toluene, ethyl acetate, DMF, DMSO, CH$_3$CN, NMP, THF, DCM or any other suitable inert solvent as is known in the art and the reagents are soluble therein. The preferred solvents are DMF and NMP. The appropriate temperature range is −25 to +25° C., with ambient temperature being preferred. The activating agent may be selected from one of the following: PyBOP, HBTU, HATU, EDC, DIC, DCC, DCC+HOBT, OSu activated esters, azide, or triphenylphosphorylazide. HBTU or HATU is the preferred activating agent. Alternatively, the acid chloride or the acid bromide of the protected peptide can also be used for this coupling reaction. 2–4 equivalent, advantageously 2–2.5 equivalent of a base is required for the coupling reaction. The base can be selected from inorganic bases such as CsCO$_3$, Na$_2$CO$_3$, or K$_2$CO$_3$, or organic bases, such as TEA, DIEA, DBU, DBN, DBO, pyridine, substituted pyridines, N-methyl-morpholine etc., preferably TEA, or DIEA. The reaction can be carried out at temperatures between −15° C. and 50° C., advantageously between −10° C. and 10° C. The reaction time is between 5–90 minutes and is advantageously 20–40 minutes. The product is isolated by pouring the reaction mixture into water and filtering the precipitate formed. The crude product can be further purified by recrystallization from DCM, THF, ethyl acetate, or acetonitrile, preferably from dichloromethane or acetonitrile. The isolated Fmoc form of the oligopeptide therapeutic agent conjugate is then deprotected over 2–90 minutes, preferably 3–8 minutes, using a ten- to hundred-fold excess of base at a temperature between −10° C. and 50° C. Ideally, 5–60 equivalents of the base are preferred. Piperidine is the preferred base to deprotect Fmoc groups. The deprotected amino terminus of the oligopeptide-therapeutic agent conjugate is acylated by a diacid anhydride or a hemi protected activated diacid (i.e., a mono ester which is subsequently deprotected) to give the final N-cap form of the oligopeptide-therapeutic agent.

Figure 6:
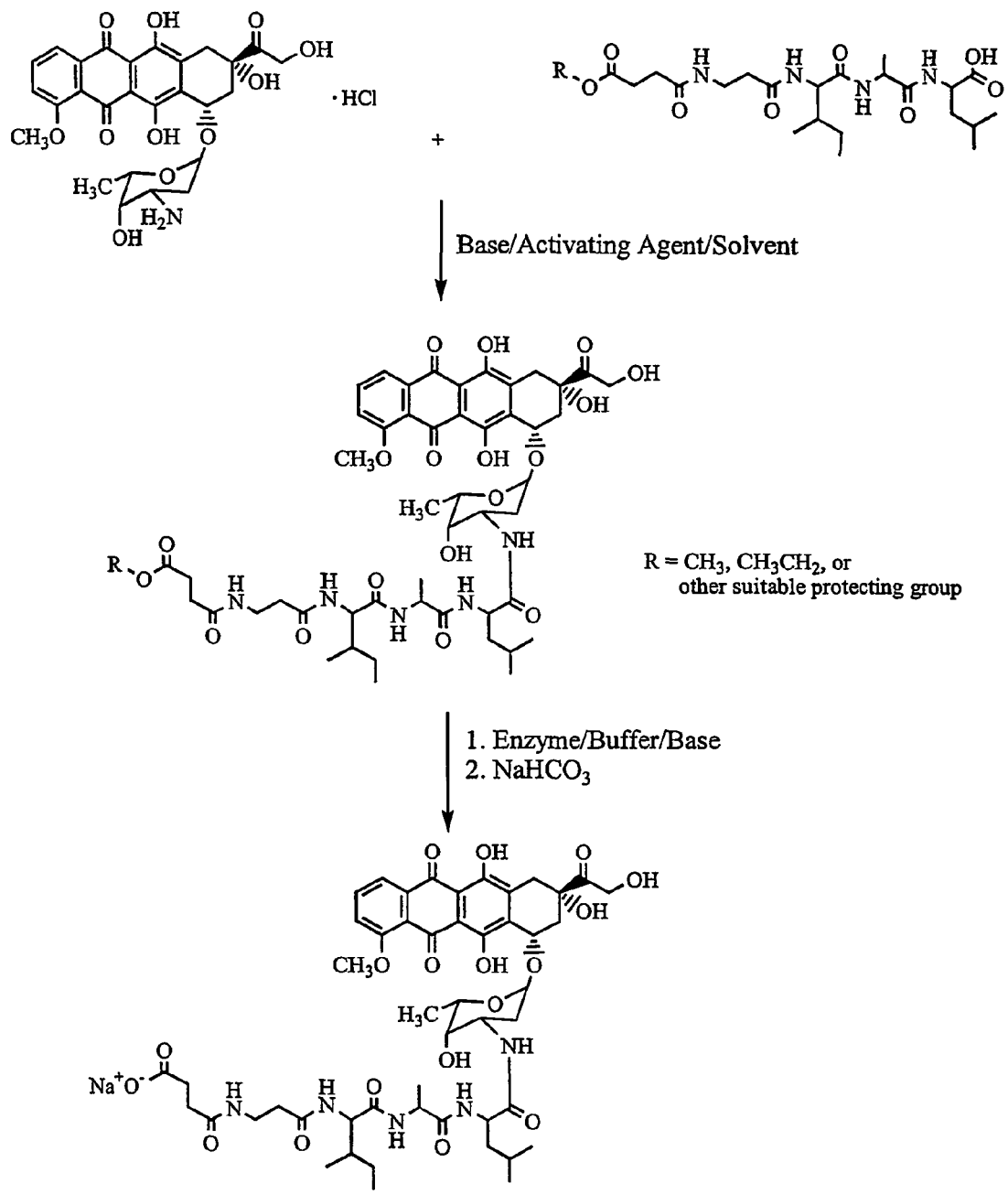
FIG. 6 illustrates an "Ester route" synthesis of a salt form of Suc-βAla-Ile-Ala-Leu-Dox (SEQ ID NO:39), a typical compound of the invention.

Alternatively, the final prodrug can be similarly prepared from the protected N-cap form of the oligopeptide such as a methyl hemiester form of succinyl-N-cap oligopeptide and conjugated to a therapeutic agent. This method is illustrated in FIG. 6.

The protected N-Cap-oligopeptide-therapeutic agent is now deprotected by methods compatible with the stability of the therapeutic agent. For example, anthracyclines may be protected with a methyl group and deprotected with an esterase. For other therapeutic agents, benzyl protecting groups and catalytic hydrogenation may be selected for deprotection.

The salt form of the negatively charged N-cap oligopeptide-therapeutic agent is carried out with a solvent selected from the following group: alcohol (including methanol, ethanol, or isopropanol), water, acetonitrile, tetrahydrofuran, diglyme or other polar solvents. The sodium source is one molar equivalent of NaHCO$_3$, NaOH, Na$_2$CO$_3$, NaOAc, NaOCH$_3$ (in general sodium alkoxide), or NaH. An ion exchange column charged with Na$^+$ (such as strong or weak ion exchangers) is also useful for this last step of making the salt form of the N-cap oligopeptide therapeutic agent when appropriate. Sodium is described as an example only.

Generally, the prodrug may be converted to a pharmaceutically acceptable salt form to improve solubility of the prodrug. The N-cap-oligopeptide therapeutic agent is neutralized with a pharmaceutically acceptable salt, e.g., NaHCO$_3$, Na$_2$CO$_3$, NaOH tris(hydroxymethyl)aminomethane, KHCO$_3$, K$_2$CO$_3$, CaCO$_3$, NH$_4$OH, CH$_3$NH$_2$, (CH$_3$)$_2$NH, (CH$_3$)$_3$N, acetyltriethylammonium. The preferred salt form of prodrug is sodium, and the preferred neutralizing salt is NaHCO$_3$.

It is well documented that anthracycline type molecules, including doxorubicin and daunorubicin form gels in organic solvents in very low concentrations (Matzanke, B. F., et al., *Eur. J. Biochem.*, 207:747–55 (1992); Chaires, J. B., et al., *Biochemistry*, 21:3927–32 (1982); Hayakawa, E., et al., *Chem. Pharm. Bull.*, 39:1282–6 (1991). This may be a considerable obstacle to getting high yields of clean product when making peptide anthracycline conjugates. The gel formation contributes to the formation of undesirable side reactions. One way to minimize this problem is to use very dilute solutions (1–2%) for the coupling reaction, however it is not practical in a process environment (large amounts of waste, complicated isolation). To overcome this problem urea or other chaotropic agents may be used to break up the strong hydrophobic and hydrogen bonding forces forming the gel. Thus if the coupling reaction is carried out in a urea-containing solvent, advantageously a 20% to saturated solution of urea in DMF or NMP, the side reactions can be kept below 2% even if the concentration of reactants exceeds 10%. This makes the conjugation step practical at high concentrations and produces good yields.

General Enzyme Method

Hydrolysis of protected N-cap-oligopeptide therapeutic agents to the full N-cap compound catalyzed by acids or bases leads to complex reaction mixtures due to the lability of many therapeutic agents even under moderately acidic or basic conditions. Enzymes can promote the hydrolysis without destroying the substrate or the product. Enzymes suitable for this reaction can be esterases or lipases and can be in their natural, water soluble forms or immobilized by cross coupling, or attachment to commercially available solid support materials. Of the soluble enzymes evaluated, *Candida Antarctica* "B" lipase (Altus Biologics) is especially useful. An example of an enzyme immobilized by cross coupling is ChiroCLEC-PC™ (Altus Biologics). *Candida Antarctica* "B" lipase (Altus Biologics) can be immobilized by reaction with NHS activated Sepharose™ 4 Fast Flow (American Pharmacia Biotech). The pH of the reaction mixture during the hydrolysis is carefully controlled and maintained by a pH-stat between 5.5 and 7.5, advantageously between 5.7 and 6.5, via controlled addition of NaHCO$_3$ solution. When the reaction is completed the product is isolated by lyophilization of the filtered reaction mixture. The immobilized enzymes remain on the filter cake and can be reused if desired.

General Allyl or Alkyl Ester Method

Figure 8:
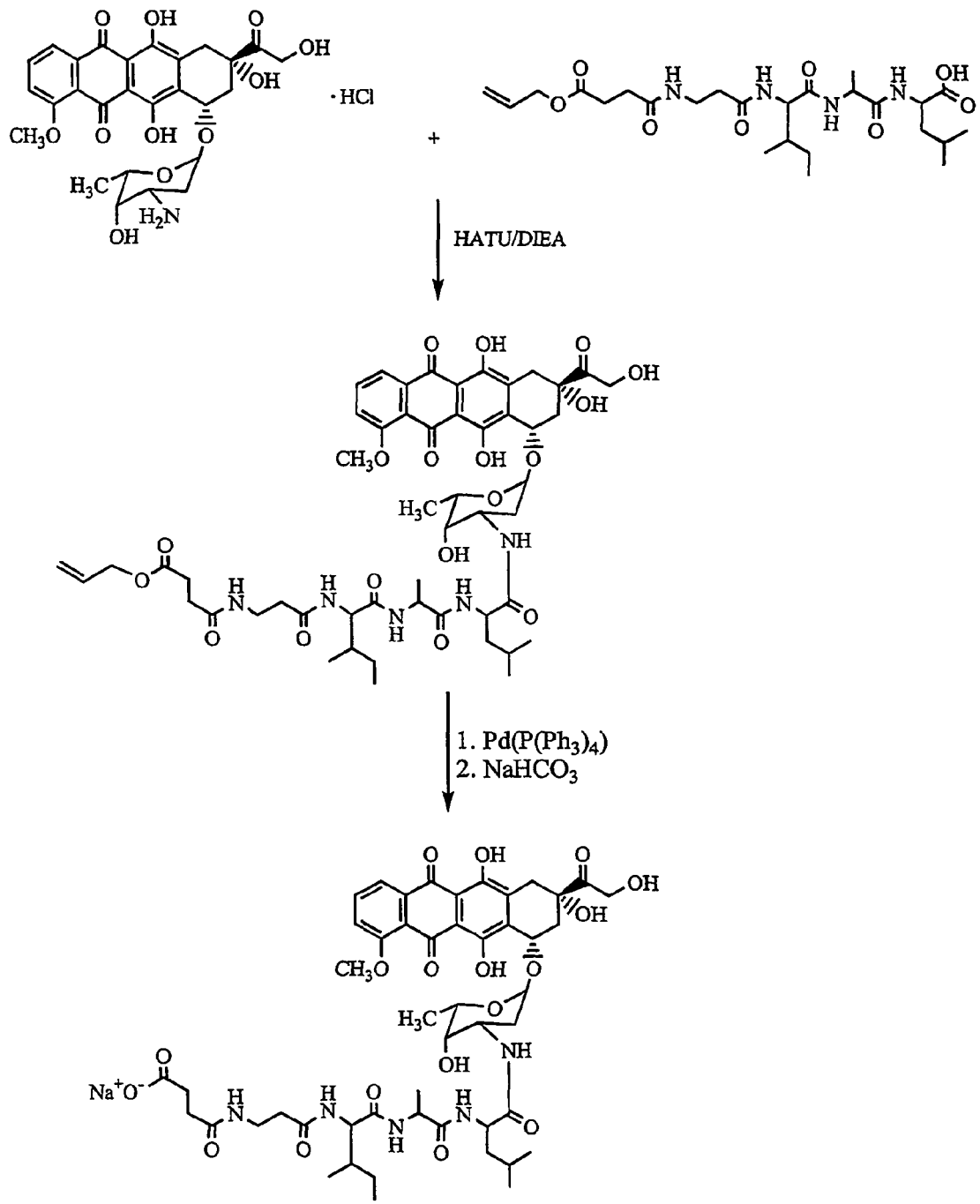
FIG. 8 illustrates an "Allyl ester route" synthesis of a salt form of Suc-βAla-Ile-Ala-Leu-Dox (SEQ ID NO:39), a typical compound of the invention.

The prodrug can also be prepared via coupling an allyl-hemiester or alkyl hemiester form of the N-cap oligopeptide with a therapeutic agent and then liberating the free acid from the conjugate. FIG. 8 illustrates this process with Succinyl-β-Ala-Ile-Ala-Leu (SEQ ID NO:44) and doxorubicin.

The coupling of allyl-succinyl-βAla-Ile-Ala-Leu (SEQ ID NO:45) with doxorubicin can be carried out via any one of the oligopeptide conjugation methods. Allyl-succinyl-βAla-Ile-Ala-Leu-doxorubicin (SEQ ID NO:46) can also be synthesized by reacting allyl hemisuccinate, which was prepared via known methods (Casimir, J. R., et al., *Tet. Lett.* 36/19 3409 (1995)), with βAla-Ile-Ala-Leu-doxorubicin (SEQ ID NO:40) similarly as coupling of the protected tetrapeptide precursors to doxorubicin was described in the previous methods, shown in FIG. 5. Suitable inert solvents are THF, dichloromethane, ethyl acetate, toluene, preferably THF from which the acid form of the product precipitates as the reaction progresses. The isolated acid is converted to its sodium salt as described earlier. Reaction times vary between 10–180 minutes, advantageously 10–60 minutes, at temperatures between 0–60° C., preferably 15–30° C.

Removal of the allyl or alkyl group can be done with Pd(0), or Ni(0), advantageously Pd(0) promoted transfer of the allyl or alkyl group to acceptor molecules, as it is well known in the art and documented in the scientific literature (Genet, J-P, et al., *Tet. Lett.*, 50, 497, 1994; Bricout, H., et al. *Tet. Lett.*, 54:1073 (1998), Genet, J-P. et al. Synlett, 680 (1993); Waldmann, H., et al., *Bioorg. Med. Chem.*, 7:749 (1998); Shaphiro, G., Buechler, D., *Tet. Lett.*, 35:5421 (1994)). The amount of catalyst can be 0.5–25 mol % to the substrate.

General Trityl or Substituted Trityl Method

Figure 7:
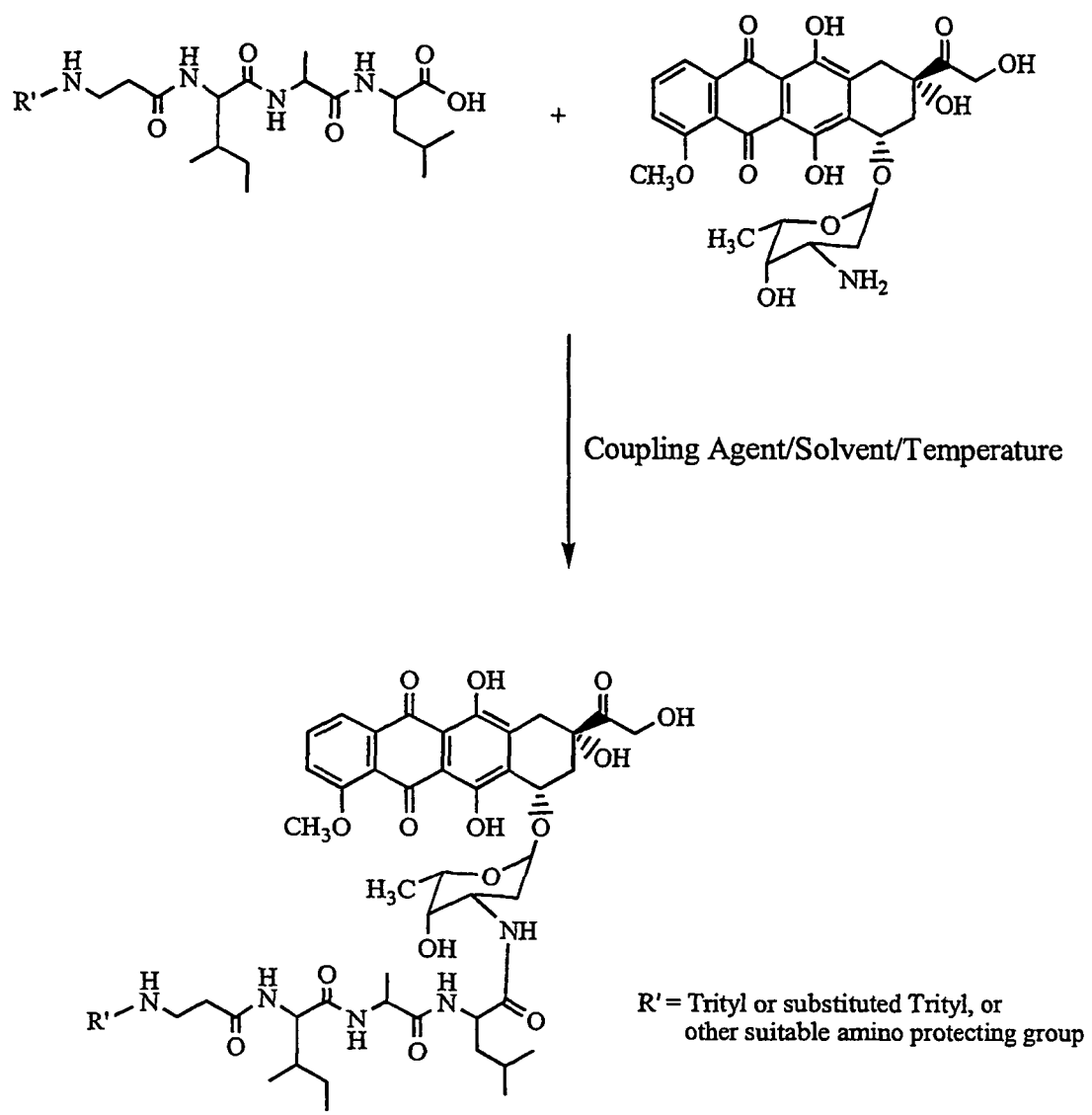
FIG. 7 illustrates a synthesis of an amino-protected βAla-Ile-Ala-Leu-Dox (SEQ ID NO:40), a typical intermediate of the invention.

The prodrug may also be synthesized via the method shown in FIG. 7. This approach utilizes an R'-oligopeptide, where R' is trityl or substituted trityl. The coupling of R'-oligopeptide with a therapeutic agent can be carried out via any one of the methods described earlier for conjugation of a protected oligopeptide with a therapeutic agent at 30–120 minutes at 0–20° C.

Removal of trityl or substituted trityl group can be achieved under acidic conditions to give the positively charged prodrug. This positively charged prodrug is N-capped as illustrated in FIG. 4 and described earlier. The trityl deprotection can be accomplished with acetic acid, formic acid and dilute hydrochloric acid.

The prodrug can be converted into (succinyl or glutaryl)-oligopeptide-therapeutic agent by reacting with succinic anhydride or glutaric anhydride, then further converted into any pharmaceutically acceptable salt. The solvent for the coupling step may be DMF, DMSO, CH$_3$CN, NMP, or any other suitable solvent is known in the art.

General Inverse Direction Solid Phase Conjugation Method

The prodrug compound of the present invention can be synthesized by using solid phase chemistry via "step wise" inverse (from the N-terminal to the C-terminal) direction methods.

Figure 9:
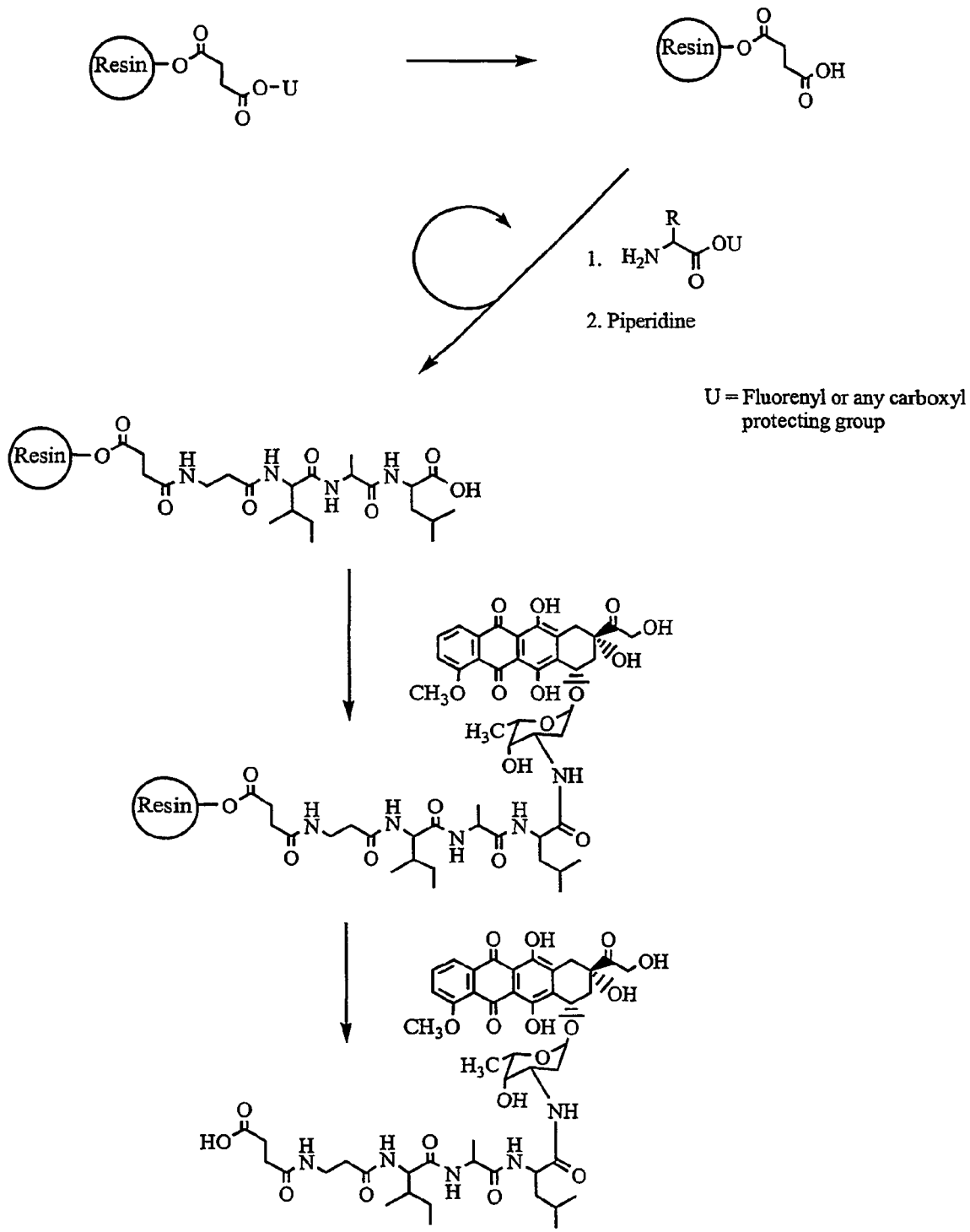
FIG. 9 illustrates a "Resin route" synthesis of Suc-βAla-Ile-Ala-Leu-Dox (SEQ ID NO:39), a typical compound of the invention.

One way is to use resins to immobilize a succinyl hemiester, for example succinyl-mono-benzyl ester or -allyl ester. Examples of resins could be selected are "Wang Resins" (Wang, S. S., *J. Am. Chem. Soc.*, 95:1328 (1973); Zhang, C., Mjaili, A. M. M., *Tet. Lett.*, 37:5457(1996)), "Rink Resins" (Rink, H., *Tet. Lett.*, 28:3787 (1987)), "Trityl-, or substituted-trityl Resins" (Chen, C., et al., *J. Am. Chem. Soc.*, 116:2661 (1994); Bartos, K. et al., *Peptides. Proc. 22$^{nd}$ European Peptide Symposium* (1992); Schneider, C. H.; Eberle, A. N. (Eds.), *ESCOM, Leiden*, pp. 281 (1993). The immobilized ester is then deprotected and reacted with, for example, a similarly C-terminal protected β-alanine. These steps are then repeated with isoleucine, alanine, and finally leucine esters, followed by the coupling of doxorubicin to the immobilized succinyl-tetrapeptide. The molecule is then liberated from the resin by using mildly acidic conditions to form a free prodrug, such as Suc-βAla-Ile-Ala-Leu-Dox (SEQ ID NO:39). This methodology is represented on the scheme of FIG. 9. Another version of phase synthesis utilizes immobilized succinyl oligopeptide ester. This is then C-terminally deprotected, followed by the coupling step to doxorubicin or other therapeutic agent and finally liberated from the resin as represented on the scheme of FIG. 9. The acid form of the prodrug molecules may then be converted finally into its sodium salt as described above.

Removal of Free Therapeutic Agent

Figure 17:
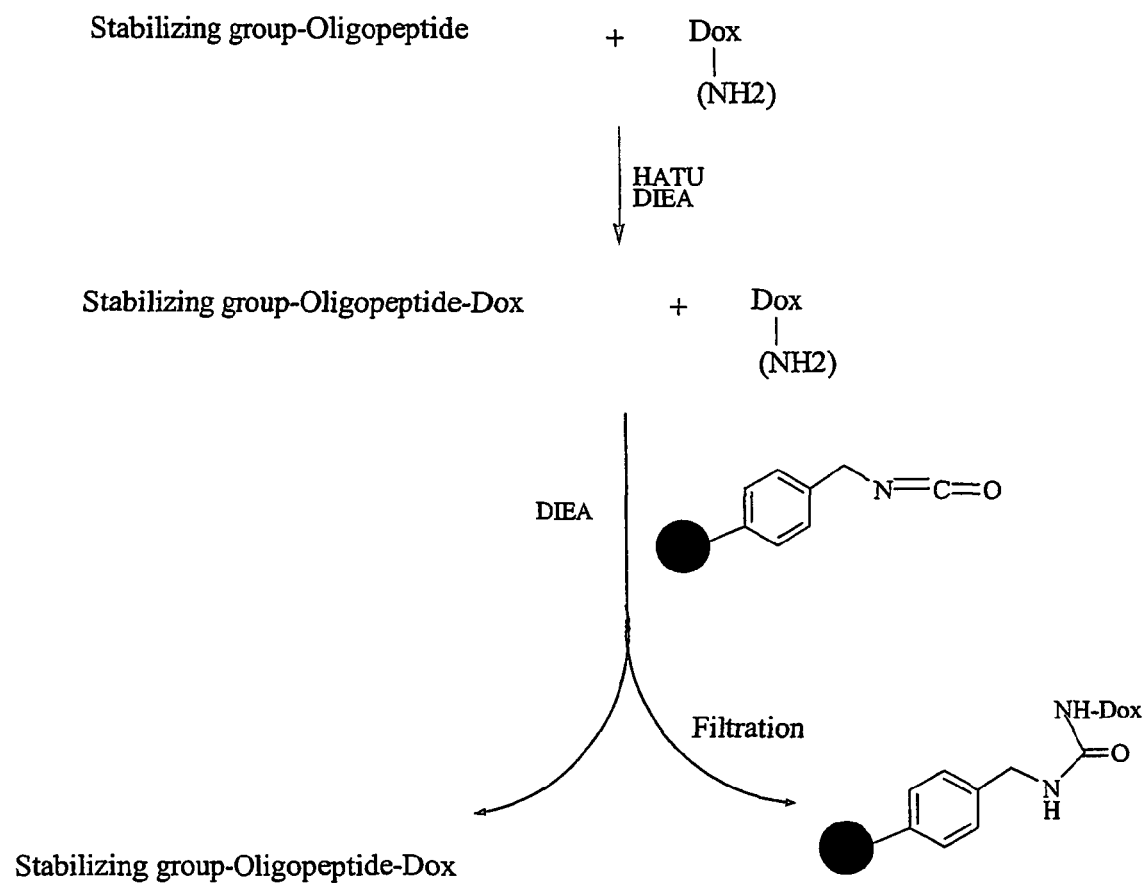
FIG. 17 illustrates the removal of free therapeutic agent through the use of scavenging resin or beads.

Unconjugated therapeutic agent may be present late in the process of making the prodrug. For example, during the coupling step of (stabilizing group)-(oligopeptide) conjugate with doxorubicin as the therapeutic agent, it was found, in some instances, that the reaction did not proceed completely. There was about 2–4% of residual doxorubicin remaining in the coupled product. Initial attempts to remove doxorubicin completely from the product by acidic washes did not result in complete removal. The complete removal of the free therapeutic agent was effected by the process outlined in Example 21 and FIG. 17 that utilizes scavenging resin or beads.

The crude product, which contains the intermediate and residual doxorubicin, were dissolved in DMF and polystyrene methylisocyanate or polystyrene sulfonyl chloride resin or beads were added. The reaction was stirred for 60 minutes. The free amino group of doxorubicin reacts with the isocyanate or sulfonyl chloride group on the beads to form a urea or sulfonamide derivative. The solid beads with doxorubicin attached to them were then separated from the desired product by filtration. The desired product remains in the DMF solution. This approach seems to be a very mild and effective method for removing residual therapeutic agent from the product.

General Large Scale Compound Synthesis

The prodrug compound can be synthesized using a simple and efficient three-step process of the invention: (1) coupling an alkyl or allyl ester protected stabilizing group-oligopeptide and a therapeutic agent in the presence of an activating agent to make an alkyl or allyl ester protected stabilizing group-oligopeptide-therapeutic agent conjugate, (2) removing uncoupled therapeutic agent that remains after the coupling step, and (3) deprotecting the alkyl or allyl ester protected stabilizing group-oligopeptide-therapeutic agent conjugate to make the stabilizing group-oligopeptide-therapeutic agent prodrug compound.

The first step involves the coupling of an alkyl-ester protected oligopeptide fragment to a therapeutic agent. A preferred embodiment of the first step involves the coupling of an alkyl or allyl ester protected stabilizing group oligopeptide, such as MeOSuc-βAla-Ile-Ala-Leu-OH (SEQ ID NO:47), with a therapeutic agent, such as doxorubicin, using an activating agent, such as HATU, to give alkyl or allyl ester protected stabilizing group oligopeptide therapeutic agent conjugate, e.g., MeOSuc-βAla-Ile-Ala-Leu-Dox (SEQ ID NO:48). The focus of this step is on the purity and the yield of the methyl ester, since it was found that the hydrolysis step did not have an impact on purity. Preferably the molar ratio of the alkyl or allyl ester protected stabilizing group oligopeptide to the therapeutic agent will be between 2:1 and 1:1. More preferably the molar ratio is between 1.75:1 and 1.5:1. Most preferably the molar ratio is 1.66:1.

The coupling of the alkyl or allyl ester protected stabilizing group oligopeptide and a therapeutic agent is preferably performed by: (a) combining the alkyl or allyl ester protected stabilizing group oligopeptide and the therapeutic agent in DMF, (b) adding DIEA, (c) reacting the alkyl or allyl ester protected stabilizing group oligopeptide and the therapeutic agent in the presence of the activating agent to form the conjugate, and (d) precipitating the conjugate by adding a brine solution to form a precipitate. Preferably the molar ratio of the DIEA and the alkyl or allyl ester protected stabilizing group-oligopeptide is between 3:1 and 1.5:1. More preferably the molar ratio is 2.5:1 and 2:1. Most preferably the molar ratio is 2.18:1. The reacting step is preferably performed at 0° C., for 30 minutes. Preferably the molar ratio of the activating agent and the alkyl or allyl ester protected stabilizing group-oligopeptide is between 1.5:1 and 1:1. More preferably, the molar ratio is 1.1:1. The brine solution is preferably between 20% (w/v) and 40% (w/v) of NaCl in water. More preferably the brine solution is preferably between 25% (w/v) and 35% (w/v) of NaCl in water. Most preferably the brine solution is 30% (w/v) of NaCl in water. The conjugate is preferably precipitated in a brine solution, wherein the pH is between 5.0 and 7.0, inclusive. Most preferably, the conjugate is precipitated at a pH between 5.8 and 6.0.

Since many therapeutic agents are toxic substances, it is preferable to eliminate any free therapeutic agent from the coupled product. The removing step is preferably performed by: (a) dissolving the conjugate in DMF, (b) dissolving a scavenger resin in anhydrous DMF, (c) adding the alkyl or allyl ester protected stabilizing group oligopeptide therapeutic agent conjugate formed in the coupling step to the scavenger resin to form a conjugate-resin mixture, (d) maintaining the mixture at between 0° C. and 30° C. for 2 to 24 hours wherein the uncoupled therapeutic agent reacts with the resin, (e) removing the resin from the mixture, and (f) precipitating the remainder by adding a brine solution to form a precipitate of the alkyl or allyl ester protected stabilizing group oligopeptide therapeutic agent conjugate. Preferably the scavenger resin is polystyrene-isocyanate (PS-isocyanate), PS-methylisocyanate, PS-thioisocyanate, PS-methylthioisocyanate, PS-sulfonyl chloride, PS-methylsulfonyl chloride or PS-benzaldehyde. Most preferably, the scavenger resin is PS-isocyanate. The removing step is preferably performed to remove free therapeutic agent, which is an anthracycline.

The third step is deprotecting the alkyl or allyl ester protected stabilizing group-oligopeptide-therapeutic agent conjugate, preferably via hydrolysis by an enzyme, more preferably via hydrolysis by an esterase, which directly gives the prodrug compound in good yield with a final purity of at least 90%. For example, the third step may be the hydrolysis of the methyl ester group in MeOSuc-βAla-Ile-Ala-Leu-Dox (SEQ ID NO:48) by an enzyme, such as CLEC CAB (crosslinked *Candida Antartica* B Lipase), which directly gives the sodium salt of Suc-βAla-Ile-Ala-Leu-Dox (SEQ ID NO:39) in quantitative yields with high purity.

The enzyme is preferably either crosslinked or immobilized on a solid support. The esterase may be pig liver esterase, *Candida Antartica* B Lipase, *Candida Rugosa* lipase, *Pseudomonas Cepacia* lipase, pig liver esterase immobilized on sepharose, *Candida antartica* B lipase immobilized on sepharose, CLEC-PC™ (*Pseudomonas Cepacia* lipase ), CLEC-CAB (*Candida Antartica* B lipase), or CLEC-CR (*Candida Rugosa* lipase). Deprotecting via hydrolysis by an enzyme is preferably performed by: (a) washing the enzyme to remove free enzyme, (b) adding the washed enzyme to the alkyl or allyl ester protected stabilizing group-oligopeptide-therapeutic agent conjugate, (c) reacting the enzyme with the conjugate at between 15° C. and 40° C., inclusive, at a pH between 5.0 and 8.0, inclusive, for at least 18 hours, to create the stabilizing group-oligopeptide-therapeutic agent prodrug compound, and (d) separating the enzyme from the prodrug compound. Most preferably additional washed crosslinked or immobilized enzyme is added after the step of reacting the enzyme with the conjugate, prior to separating the enzyme from the prodrug compound.

Thus, the invention includes a method of making a compound comprising:
(1) selecting an Fmoc-protected oligopeptide of the formula Fmoc-(AA)$_n$-AA$^3$-AA$^2$-AA$^1$, wherein:
   each AA independently represents an amino acid,
   n is 0 or 1, and when n is 1, then (AA)$_n$ is AA$^4$ which represents any amino acid,
   AA$^3$ represents isoleucine,
   AA$^2$ represents any amino acid, and
   AA$^1$ represents any amino acid,
(2) coupling the Fmoc-protected oligopeptide to a therapeutic agent by activating the Fmoc-protected oligopeptide with an activating agent in the presence of the therapeutic agent to form an Fmoc-protected oligopeptide-therapeutic agent conjugate,
(3) deprotecting the Fmoc-protected oligopeptide-therapeutic agent conjugate by contacting it with a base to form an oligopeptide-therapeutic agent conjugate, and
(4) coupling the oligopeptide-therapeutic agent conjugate to a stabilizing group to form the compound.

Alternatively, a method of making a compound comprises the following steps:
(1) selecting an oligopeptide having a formula (AA)$_n$-AA$^3$-AA$^2$-AA$^1$, wherein:
   each AA independently represents an amino acid,
   n is 0 or 1, and when n is 1, then (AA)$_n$ is AA$^4$ which represents any amino acid,
   AA$^3$ represents isoleucine,
   AA$^2$ represents any amino acid, and
   AA$^1$ represents any amino acid,
(2) coupling the oligopeptide to an alkyl ester-protected stabilizing group to form an alkyl ester-protected stabilizing group-oligopeptide conjugate,
(3) coupling the alkyl ester-protected-stabilizing group-oligopeptide conjugate to a therapeutic agent by activating the alkyl ester-protected stabilizing group-oligopeptide conjugate with an activating agent in the presence of a therapeutic agent to form an alkyl ester-protected stabilizing group-oligopeptide-therapeutic agent conjugate, and
(4) deprotecting the alkyl ester-protected stabilizing group-oligopeptide therapeutic agent conjugate to form the compound.

A compound of the invention may also be made via the following steps:
(1) selecting an oligopeptide of the formula (AA)$_n$-AA$^3$-AA$^2$-AA$^1$, wherein:
   each AA independently represents an amino acid,
   n is 0 or 1, and when n is 1, then (AA)$_n$ is AA$^4$ which represents any amino acid,
   AA$^3$ represents isoleucine,
   AA$^2$ represents any amino acid, and
   AA$^1$ represents any amino acid,
(2) coupling the oligopeptide to an allyl ester-protected stabilizing group to form an allyl ester-protected stabilizing group-oligopeptide conjugate,
(3) coupling the allyl ester-protected-stabilizing group-oligopeptide conjugate to a therapeutic agent by activating the allyl ester-protected stabilizing group-oligopeptide conjugate with an activating agent in the presence of a therapeutic agent to form an allyl ester-protected stabilizing group-oligopeptide-therapeutic agent conjugate, and
(4) deprotecting the allyl ester-protected stabilizing group-oligopeptide therapeutic agent conjugate to form the compound.

Yet another method for making a compound of the invention comprises the following steps:
(1) selecting a trityl-protected oligopeptide of the formula trityl-(AA)$_n$-AA$^3$-AA$^2$-AA$^1$, wherein:
   each AA independently represents an amino acid,
   n is 0 or 1, and when n is 1, then (AA)$_n$ is AA$_4$ which represents any amino acid,
   AA$^3$ represents isoleucine,
   AA$^2$ represents any amino acid, and
   AA$^1$ represents any amino acid,
(2) coupling the trityl-protected oligopeptide to a therapeutic agent by activating the trityl-protected oligopeptide with an activating agent in the presence of a therapeutic agent, thereby making a trityl-protected oligopeptide-therapeutic agent conjugate,
(3) deprotecting the trityl-protected oligopeptide-therapeutic agent conjugate under acidic conditions to form an oligopeptide-therapeutic agent conjugate, and
(4) coupling the oligopeptide-therapeutic agent conjugate with an stabilizing group to form the compound.

Another possible step in connection with any of these methods is removing uncoupled therapeutic agent by use of scavenging resin or beads. Further, the compound may be neutralized with a pharmaceutically acceptable salt if desired.

Specific Compounds

Compounds of the invention include the prodrugs specifically listed in Table 1 (under Example 1).

EXAMPLES

Example 1

Screening of Potential Prodrugs

A good candidate for a prodrug with improved therapeutic index is activated by cancer cells but relatively stable in whole human blood. Three different preparations of carcinoma cell trouase were used to screen various test compounds. These three preparations were as follows:
(a) MCF 7/6 (breast carcinoma) cell homogenate
(b) MCF 7/6 (breast carcinoma) conditioned media, and
(c) HeLa (cervical carcinoma) cell extract anion exchange fraction pool.

a. Preparation of MCF 7/6 Cell Homogenate

MCF 7/6 cells were grown to confluence in a serum free medium containing DMEM:F12 (1:1), 50 mg/L bovine serum albumin, ITS-X (10 mg/L insulin, 5.5 mg/L transferrin, 6.7 µg/L Na selenite, 2 mg/L ethanolamine), and Lipid Concentrate (Gibco #21900–030)100 mL of cells were harvested by centrifugation at 4° C. 10,000×g, for 20 min and decanting the supernatant. The pellet was resuspended in 2 mL phosphate buffered saline (Gibco) and centrifuged at 18,000×g for 10 min. After decanting the supernatant, the cells (approximately 300 µL wet) were homogenized by grinding in 1.7 mL 10 mM pH 7.2 HEPES buffer (sodium salt). The homogenate was centrifuged at 18,000×g at 4° C. for 5 min and the supernatant was aliquoted and stored at ≦−20° C. for subsequent use in the compound screen.

b. Preparation of MCF 7/6 Conditioned Media

MCF 7/6 cells were grown to confluence in DMEM/F12 (1:1) medium containing 10% fetal bovine serum, 0.05% (w/v) L-glutamine, 250 IU/mL penicillin, and 100 µg/mL streptomycin. Cells were then washed twice with phosphate buffered saline and incubated 24 hr at 5% CO$_2$, 37° C., in DMEM/F12 (1:1), 0.02% BSA, ITS-X (10 mg/L insulin, 5.5 mg/L transferrin, 6.7 µg/L Na selenite, 2 mg/L ethanolamine). The conditioned media was then decanted and, using a stirred cell apparatus with a YM10 (10,000 MW cutoff) ultrafiltration membrane(Millipore), exchanged once with 10 mM HEPES buffer, pH 7.2 and concentrated twenty-fold. This solution was stored in aliquots at −20° C. for use in the compound screen.

c. Preparation of HeLa Cell Anion Exchange Fraction Pool

Thirty billion commercially produced HeLa Cells (human cervical carcinoma, *Computer Cell Culture Center*, Seneffe, Belgium) were homogenized with a sonicator and with a Dounce homogenizer in 108 mL of aqueous lysis solution. The lysis solution contained 0.02% w/v Triton X-100, 0.04% w/v sodium azide, and a cocktail of protease inhibitors (2 tablets/50 mL Complete™, EDTA-free tablets, Roche Molecular Biochemicals). The cell homogenate was centrifuged 30 minutes at 4° C. at 5000×g and the pellet was homogenized in a second 108 mL of lysis solution using a Dounce homogenizer and centrifuged as before. The supernatants were combined and centrifuged for 90 min at 145,000×g at 4° C.

A portion of the ultracentrifugation supernatant was diluted 2-fold with a 20 mM triethanolamine-HCl pH 7.2 buffer containing 0.01% (w/v) Triton X-100 and 0.02% (w/v) sodium azide (equilibration buffer). Thirty mL of the resulting solution, corresponding to approximately 180 mg of protein, was loaded at 4° C. on a 2.6×9.4 cm Source™15Q (Amersham Pharmacia Biotech) low pressure anion exchange chromatography column (1 ml/minute). The column was then washed with 250 ml of the equilibration buffer at a flow rate of 1 mL/minute. Proteins were eluted in a NaCl linear concentration gradient (0–0.5 M in the equilibration buffer, total volume of the gradient was 1000 ml) at a flow rate of 3 ml/minute. Two-minute fractions were collected and used for enzyme activity determination using βAla-Leu-Ala-Leu-Dox (SEQ ID NO:79) as the substrate. Its transformation into Ala-Leu-Dox was quantified by reverse phase high performance liquid chromatography utilizing fluorescence detection of the anthracycline moiety. The fractions containing the highest activity levels were pooled (fractions #43–46; ~0.13 M NaCl), supplemented with protease inhibitors (Complete™, EDTA-free tablets, *Roche Molecular Biochemicals*), and stored as aliquots at −80° C.

d. Cleavage Assay

Test compounds were incubated for 2 hr at 37° C. at a concentration of 12.5 µg/mL with each of the three different preparations of carcinoma cell enzyme. Following incubation, three volumes of acetonitrile were added to stop the reaction and remove protein from the mixture. The sample was centrifuged at 18,000 g for 5 minutes and 100 µL of supernatant was mixed with 300 µL of water prior to analysis by HPLC. For HPLC analysis, 50 µL of sample was injected on a 4.6×50 mm 2 µ TSK Super-ODS chromatography column at 40° C. and eluted with a 3 minute linear gradient from 26% to 68% acetonitrile in aqueous 20 mM ammonium formate pH 4.5 buffer at 2 mL/min. Detection was by fluorescence using an excitation wavelength of 235 nm and an emission wavelength of 560 nm.

Test compounds that were not cleaved (less than or equal to 5% of control) by the enzyme preparations under the given conditions are shown in Table 1 below. With few exceptions, results for carcinoma cell enzyme cleavage were identical for a partially purified fraction from HeLa cells, MFC 7/6 cell homogenate, and MCF 7/6 conditioned media.

TABLE 1

| No: | Stabilizing Group | $(AA_4)$ | $(AA_3)$ | $(AA_2)$ | $(AA_1)$ | Therapeutic Compound |
|---|---|---|---|---|---|---|
| 1 | Suc | βAla | Ile | Ala | Phe | Dnr (SEQ ID NO:49) |
| 2 | Suc | βAla | Ile | Ala | Ile | Dnr (SEQ ID NO:50) |
| 3 | Suc | Tic | Ile | Ala | Leu | Dnr (SEQ ID NO:51) |
| 4 | Suc | Thi | Ile | Ala | Leu | Dnr (SEQ ID NO:52) |
| 5 | Suc | Nal | Ile | Ala | Leu | Dnr (SEQ ID NO:53) |
| 6 | Suc | βAla | Ile | Ala | Leu | Dnr (SEQ ID NO:43) |
| 7 | Suc | Amb | Ile | Ala | Leu | Dnr (SEQ ID NO:54) |
| 8 | Suc | Aib | Ile | Ala | Leu | Dnr (SEQ ID NO:55) |
| 9 | Suc | βAla | Ile | Ala | Leu | Dox (SEQ ID NO:39) |
| 10 | Suc | Thi | Ile | Aib | Leu | Dnr (SEQ ID NO:56) |
| 11 | Suc | Nal | Ile | Aib | Leu | Dnr (SEQ ID NO:57) |
| 12 | Suc | βAla | Ile | Aib | Leu | Dnr (SEQ ID NO:58) |
| 13 | Suc | Amb | Ile | Aib | Leu | Dox (SEQ ID NO:59) |
| 14 | Suc | Aib | Ile | Aib | Leu | Dnr (SEQ ID NO:60) |
| 15 | Suc | βAla | Ile | Gly | Phe | Dnr (SEQ ID NO:61) |
| 16 | Suc | βAla | Ile | Gly | Ile | Dnr (SEQ ID NO:62) |
| 17 | Suc | Tic | Ile | Gly | Leu | Dnr (SEQ ID NO:63) |
| 18 | Suc | Thi | Ile | Gly | Leu | Dnr (SEQ ID NO:64) |
| 19 | Suc | Nal | Ile | Gly | Leu | Dnr (SEQ ID NO:65) |
| 20 | Suc | βAla | Ile | Gly | Leu | Dnr (SEQ ID NO:66) |
| 21 | Suc | Amb | Ile | Gly | Leu | Dnr (SEQ ID NO:67) |
| 22 | Suc | Aib | Ile | Gly | Leu | Dnr (SEQ ID NO:68) |
| 23 | Suc | βAla | Ile | Thr | Ile | Dnr (SEQ ID NO:69) |
| 24 | Suc | βAla | Ile | Tyr | Ile | Dnr (SEQ ID NO:70) |
| 25 | Suc | βAla | Ile | Tyr | Leu | Dnr (SEQ ID NO:71) |
| 26 | Suc | βAla | Ile | Tyr | Gly | Dox (SEQ ID NO:72) |
| 27 | Suc | βAla | Ile | Ala | Gly | Dox (SEQ ID NO:73) |
| 28 | Suc | Ø | Ile | Ala | Leu | Dox |
| 29 | Suc | Ø | Ile | N(Me)Ala | Leu | Dox |
| 30 | Suc | Ø | Ile | Ala | Gly | Dox |

Ø = not present

Example 2

Tumor-Activated Prodrug Activity on LNCaP, HT-29 and PC-3 Cells

Adherent cells, LNCaP (prostate carcinoma), HT-29 (colon carcinoma) and PC-3 (prostate carcinoma), were cultured in DMEM media containing 10% heat inactivated fetal calf serum (FCS). On the day of the study the cells were detached from the plate with a trypsin solution. The collected cells were washed and resuspended at a concentration of $0.25 \times 10^6$ cells/ml in DMEM containing 10% FCS. 100 µl of cell suspension were added to 96 well plates and the plates were incubated for 3 hours to allow the cells to adhere. Following this incubation, serial dilutions (3-fold increments) of doxorubicin or test compounds were made and 100 µl of compounds were added per well. The plates were then incubated for 24 hours, pulsed with 10 µl of a 100 µCi/ml $^3$H-thymidine and incubated for an additional 24 hours (total incubation time 48 hours). The plates were harvested using a 96 well Harvester (Packard Instruments) and counted on a Packard Top Count Counter. Four parameter logistic curves were fitted to the $^3$H-thymidine incorporation as a function of drug molarity using Prism software to determine $IC_{50}$ values.

| Compound | IC50 (µM) | | |
|---|---|---|---|
| | LNCaP | HT29 | PC-3 |
| DOX | 0.016 | 0.052 | 0.075 |
| Suc-Ile-Ala-Leu-Dox | 1.1 | 47 | 88 |
| Suc-Ile-NMeAla-Leu-Dox | 0.51 | 36 | 66 |
| Suc-Ile-Pro-Leu-Dox | 2.0 | 44 | 106 |
| Suc-βAla-Ile-Ala-Leu-Dox (SEQ ID NO:39) | 0.19 | 38 | 57 |

Prostate carcinoma cells, LNCaP and PC-3 cells or colon carcinoma cells HT-29, were incubated with increasing concentration of the indicated compounds for 48 hours and cellular proliferation was measured using the $^3$H-thymidine assay. The $IC_{50}$ of the positive control, doxorubicin, was 0.02–0.08 µM in the cell lines used. The data shows that multiple cells lines such as PC-3 and HT29 do not cleave the above-indicated prodrugs. In contrast, an enzyme present in or on LNCaP cells cleaves several of the Ile containing analogs. The most potent analog is exemplified with Suc-βAla-Ile-Ala-Leu-Dox (SEQ ID NO:39) that has an $IC_{50}$ of 0.19 µM on LNCaP cells.

Example 3

Suc-Ile-Ala-Leu-Dox is Well-Tolerated in Healthy Mice

Suc-Ile-Ala-Leu-Dox, an exemplary tripeptide prodrug of the invention, is well tolerated in mice. In our initial single dose Maximum Tolerated Dose (MTD) study, groups of five normal mice were administered intravenous bolus doses of Suc-Ile-Ala-Leu-Dox. The mice were observed daily for 28 days and body weights measured twice weekly. Dose levels tested were 0, 23, 47, 70, 93 and 117 mg/kg, equivalent to 0, 14, 28, 42, 56, and 70 mg of doxorubicin/kg respectively. There was no acute toxicity, and the only signs of toxicity observed was a decrease in group mean body weight for the highest dose group, which was lower than the vehicle control group throughout the study. However, there were no mortalities, and no animals exhibited morbidity. The 28-day single-dose Maximum Tolerated Dose (MTD) of Suc-Ile-Ala-Leu-Dox was not attained in this experiment, and is therefore greater than the highest dose tested, 117 mg/kg. This MTD (equivalent to 66 mg of doxorubicin/kg) is at least 16-fold higher than that of doxorubicin alone, which results in mortality following doses greater than 4 mg/kg. Post-analysis of compounds showed that they contained about 75% active compound due to water content and impurity. So the doses mentioned in the above paragraph overestimated amount of compound administered. The single does MTD (equivalent to 70 mg of doxorubicin/kg) is at least 3.3-fold higher than that of doxorubicin alone, which results in mortality following doses greater than 16 mg/kg.

The above-described experiment was re-performed (Example 8A) and the following result was obtained: the single dose MTD of Suc-Ile-Ala-Leu-Dox was determined to be 94 mg/kg (56 mg/kg doxorubicin equivalent), which is at least 3.5-fold higher than that of doxorubicin alone (16 mg/kg).

Example 4

Suc-βAla-Ile-Ala-Leu-Dox (SEQ ID NO:39) is Well Tolerated in Healthy Mice

Suc-βAla-Ile-Ala-Leu-Dox (SEQ ID NO:39), an exemplary tetrapeptide prodrug of the invention, is well tolerated in mice. In an initial single dose Maximum Tolerated Dose (MTD) study, groups of five normal mice were administered intravenous bolus doses of Suc-βAla-Ile-Ala-Leu-Dox (SEQ ID NO:39). The mice were observed daily for 28 days and body weights measured twice weekly. Dose levels tested were 0, 25, 50, 75, 100 and 125 mg/kg, equivalent to 0, 14, 28, 42, 56, and 70 mg of doxorubicin /kg respectively. No acute toxicity was observed following administration. Toxicity, including paralysis and significant body weight loss (>20% of their initial weight), was observed in the two highest dose groups. On Day 14, four animals in the 125 mg/kg dose group were euthanized due to treatment-related toxicity. On Day 21, two animals in the next highest dose group, i.e., 100 mg/kg were similarly euthanized. There was no morbidity observed in the next dose-group (75 mg/kg) and the group-mean-body-weight increased during the study.

Based on survival at Day 28, the single-dose MTD value for Suc-βAla-Ile-Ala-Leu-Dox (SEQ ID NO:39) was estimated to be 75 mg/kg (equivalent to a dose of 40 mg doxorubicin/kg). Thus, the MTD was approximately 10-fold higher than the MTD of doxorubicin alone, estimated to be 4 mg/kg based on the standard safe efficacious dose (4–8 mg/kg). The above-described experiment was re-performed (Example 9).

Post-analysis of compounds showed that they contained about 75% active compound due to water content and impurity. So the doses mentioned in the above paragraph overestimated amount of compound administered. Thus, the single dose MTD of Suc-βAla-Ile-Ala-Leu-Dox (SEQ ID NO:39) was approximately 3.7-fold higher than that of doxorubicin alone (16 mg/kg). The more relevant comparison is the repeat-dose (RD) MTD, as a single dose is not efficacious. The RD-MTD of Suc-βAla-Ile-Ala-Leu-Dox (SEQ ID NO:39) was approximately 53 mg/kg, Q7Dx5 (30 mg/kg doxorubicin equivalent, based on efficacy study in Example 8, which was at least 6.5-fold higher than the RD-MTD of doxorubicin (standard safe RD efficacious dose 4 mg/kg).

Example 5

Metabolism of Suc-Ile-Ala-Leu-Dox

The metabolism and clearance of Suc-Ile-Ala-Leu-Dox was studied in normal mice. The mice were administered Suc-Ile-Ala-Leu-Dox at a single intravenous bolus dose of 117 mg/kg. Plasma samples were obtained at 1 and 4 hours.

Plasma samples of 100 μl were transferred to Eppendorf tubes (1.5 mL) and an internal standard of daunorubicin (20 μL at 0.5 mg/ml) was added together with acetonitrile (400 μl). The tubes were capped and briefly vortexed followed by centrifugation at 14,000 rpm. 420 μl from each tube was removed and dried in vacuo. Each sample was reconstituted in 65 μl ammonium formate containing acetonitrile (20%) prior to analysis by reverse phase liquid chromatography in combination with tandem mass spectrometry (LC MS/MS).

Urine was collected at 2 and 24 hours post administration from pairs of mice in metabolic cages. Urine samples were diluted with ammonium formate containing acetonitrile (20%) to give a target analyte concentration within the practical range of the LC MS/MS assay. 30 μl of each diluted sample was placed in an Eppendorf tube (1.5 ml) and an internal standard of daunorubicin (20 μL at 0.5 mg/ml) was added together with 50 μl of ammonium formate containing acetonitrile (20%). Each sample was then analyzed by LC MS/MS.

An Agilent HP1100 HPLC with DAD detector and Chemstation software was coupled to a PE Sciex API 365 mass spectrometer with an electrospray ion source. HPLC was performed on a TSK-Gel Super ODS, 2 mm, 4.6×50 mm (TosoHaas) reversed phase column equipped with a HAI-GUARD C18 guard disc (Higgins Analytical) and stainless steel frit (Upchurch Scientific). Chromatography was performed at room temperature. The flow rate was 0.5 ml/min. Injection volume was 50 μl. Gradient elution was performed using a mobile phase of 20 mM ammonium formate with increasing amounts of acetonitrile. The API 365 was operated at 365° C. in a multiple reaction monitoring mode, set to monitor specific analyte parent-daughter ion pairs. Integration of chromatograms was performed by MacQuan software (PE Sciex) and quantitation of each analyte obtained by comparison to previously obtained calibration curves. Daunorubicin was used as an internal standard in all cases.

Figure 11:
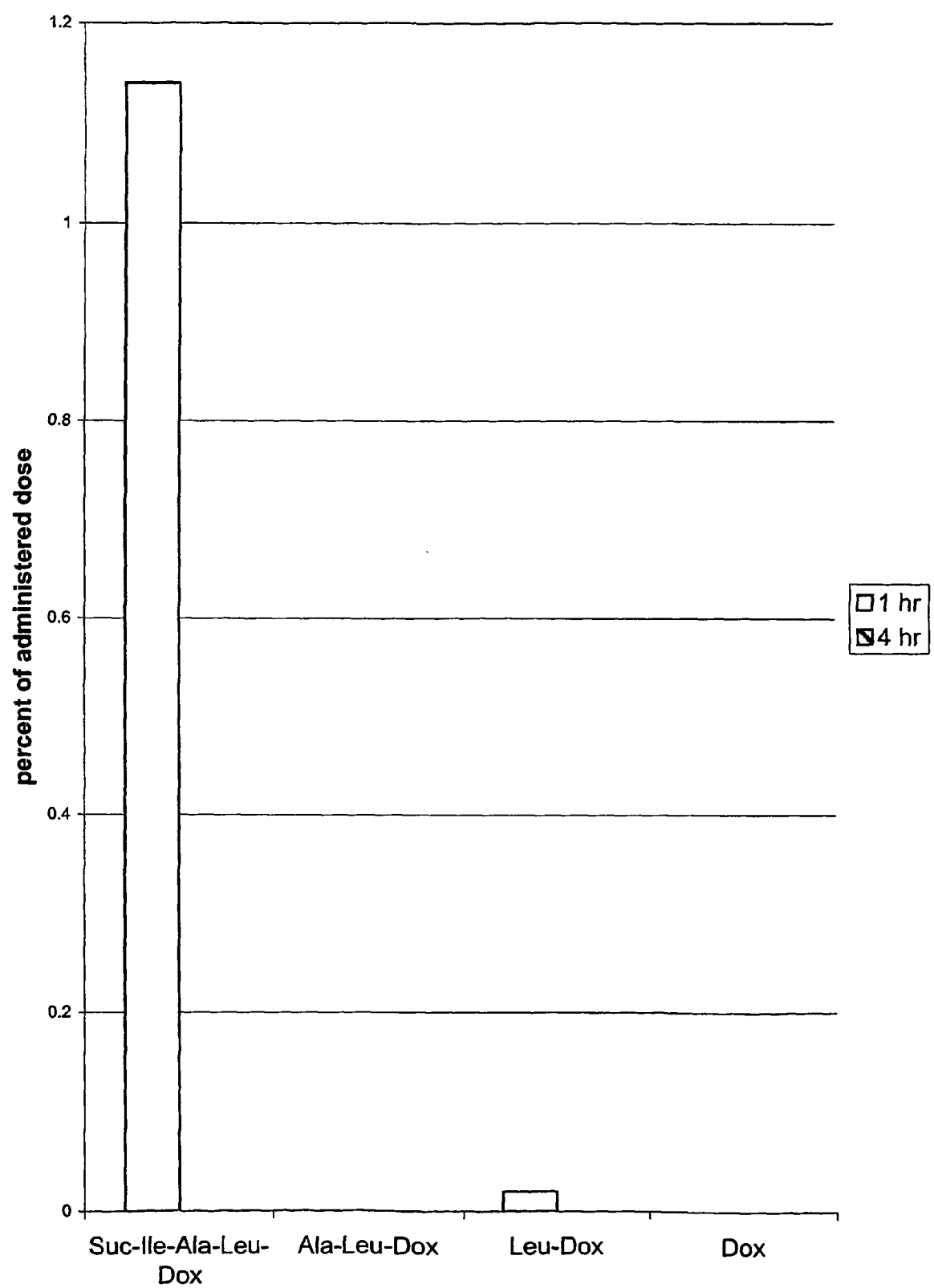
FIG. 11 is a graph of the plasma levels of Suc-Ile-Ala-Leu-Dox and its metabolites at 1 and 4 hours after administration of a single intravenous bolus dose of the prodrug.
Figure 12:
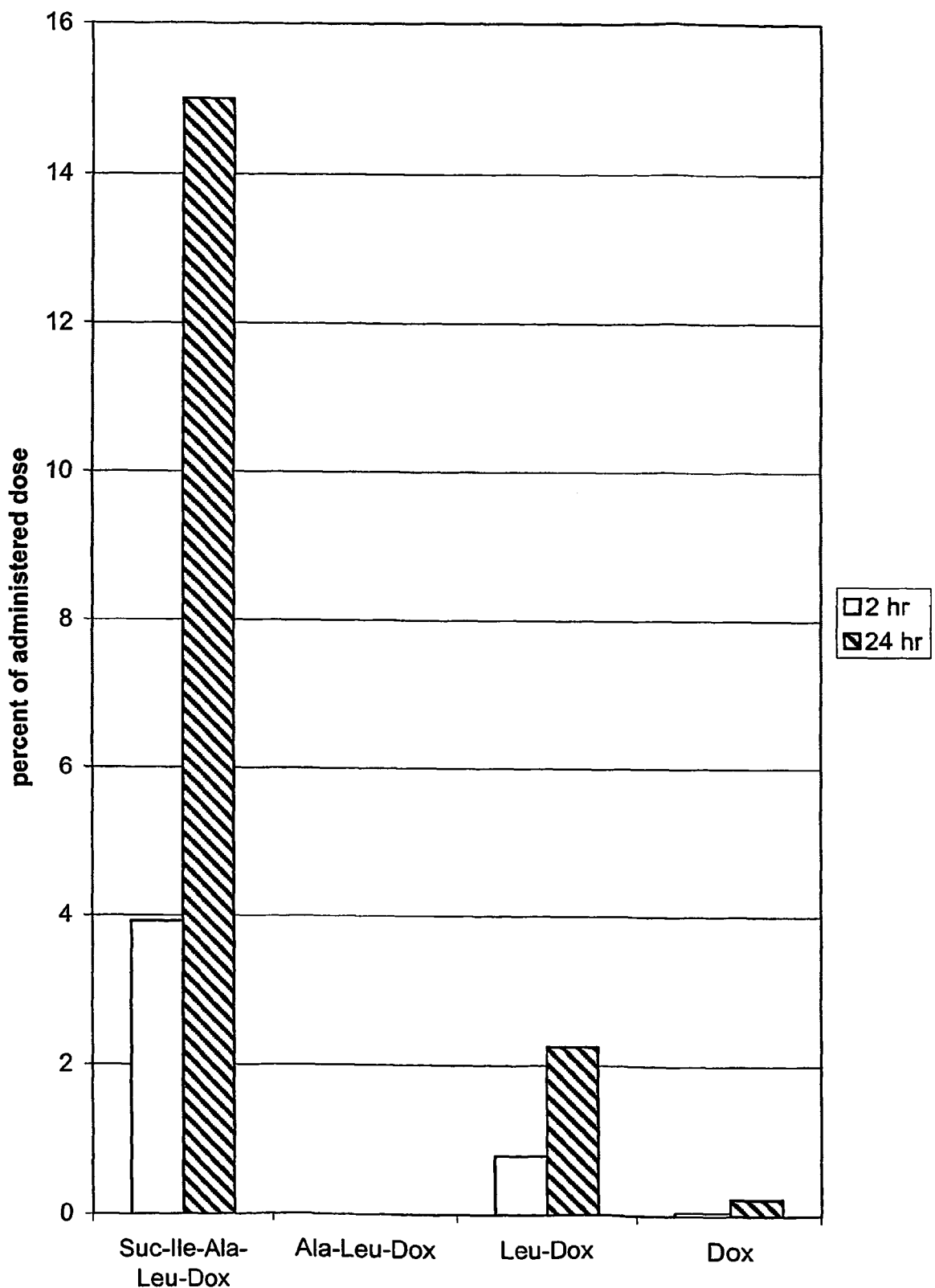
FIG. 12 is a graph of the amount of Suc-Ile-Ala-Leu-Dox and its metabolites present in the urine collected 0–2 and 2–24 hours after the administration of a single intravenous bolus of the prodrug.

As seen in Table 2 and FIG. 11, Suc-Ile-Ala-Leu-Dox was cleared from the circulation very rapidly, with approximately 1.1% of the administered dose detected at 1 hour, while by 4 hours it was virtually undetectable. At 2 and 24 hours the parent compound was detected in urine at 3.9% and 15.0% of the administered dose, showing that the kidney is a major organ of excretion for the prodrug (FIG. 12).

TABLE 2

|  | Plasma | | Urine | |
| --- | --- | --- | --- | --- |
|  | 1 hr | 4 hr | 2 hr | 24 hr |
| Suc-Ile-Ala-Leu-Dox | 1.14 | 0.00 | 3.92 | 15.0 |
| Ala-Leu-Dox | 0.00 | 0.00 | 0.00 | 0.00 |
| Leu-Dox | 0.02 | 0.00 | 1.17 | 2.25 |
| Dox | 000 | 0.00 | 0.06 | 0.36 |

Percent of administered dose - plasma volume estimated at 40% of blood volume, which was calculated at 7% of animal's body weight.

Ala-Leu-Dox was not detected in plasma or urine. The major peptide metabolite was Leu-Dox. Doxorubicin was virtually undetectable in plasma but was found in urine at low levels at 2 and 24 hours. The levels of both parent and metabolites were higher in urine at 24 hours than at 2 hours. This most likely resulted from later urination of the mice, relative to the initial urine collection time (2 hours). The urine values represent an accumulation from 0–2 hours and from 2–24 hours, thus later urination (after 2 hours) would be accumulated in the 2–24 hour sample.

A low level of cleavage and activation of the Suc-Ile-Ala-Leu-Dox prodrug occurred in the blood of normal mice. The minimal toxicity observed with Suc-Ile-Ala-Leu-Dox at the high dose-level tested (Example 2), confirms that there is almost no systemic production of the active metabolite doxorubicin which, when present systemically, is toxic to normal tissues.

Example 6

Metabolism of Suc-βAla-Ile-Ala-Leu-Dox (SEQ ID NO:39)

The metabolism and clearance of Suc-βAla-Ile-Ala-Leu-Dox (SEQ ID NO:39) was studied in normal mice administered a single intravenous bolus dose at 117 mg/kg Suc-βAla-Ile-Ala-Leu-Dox (SEQ ID NO:39). Plasma samples were obtained at 1 and 4 hours from separate mice. Urine was collected at 2 and 24 hours post administration from pairs of mice in metabolic cages. The plasma and urine samples were prepared and analyzed as described in Example 4.

Figure 13:
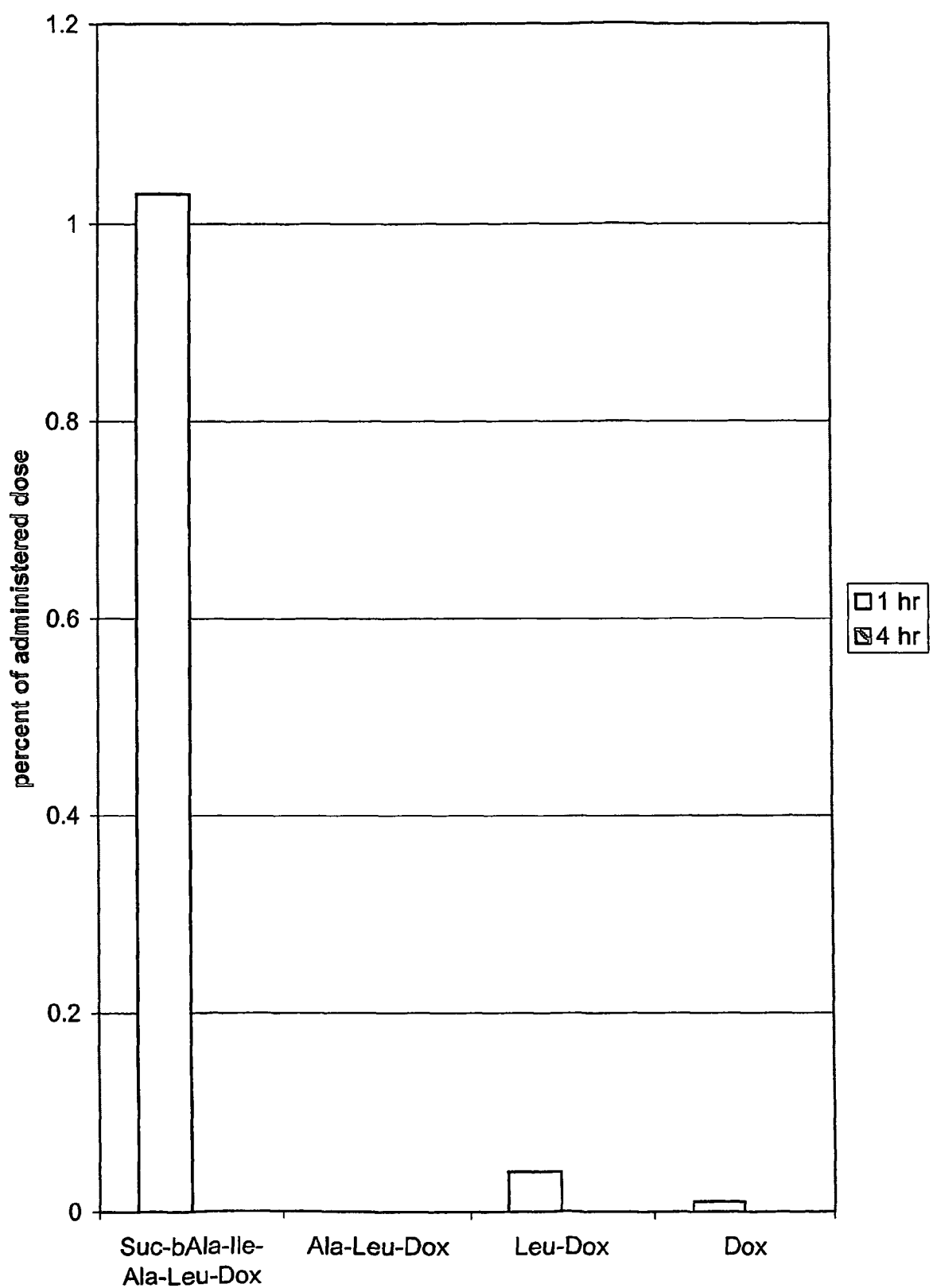
FIG. 13 is a graph of the plasma levels of Suc-βAla-Ile-Ala-Leu-Dox (SEQ ID NO:39) and its metabolites at 1 and 4 hours after administration of a single intravenous bolus dose of the prodrug.
Figure 14:
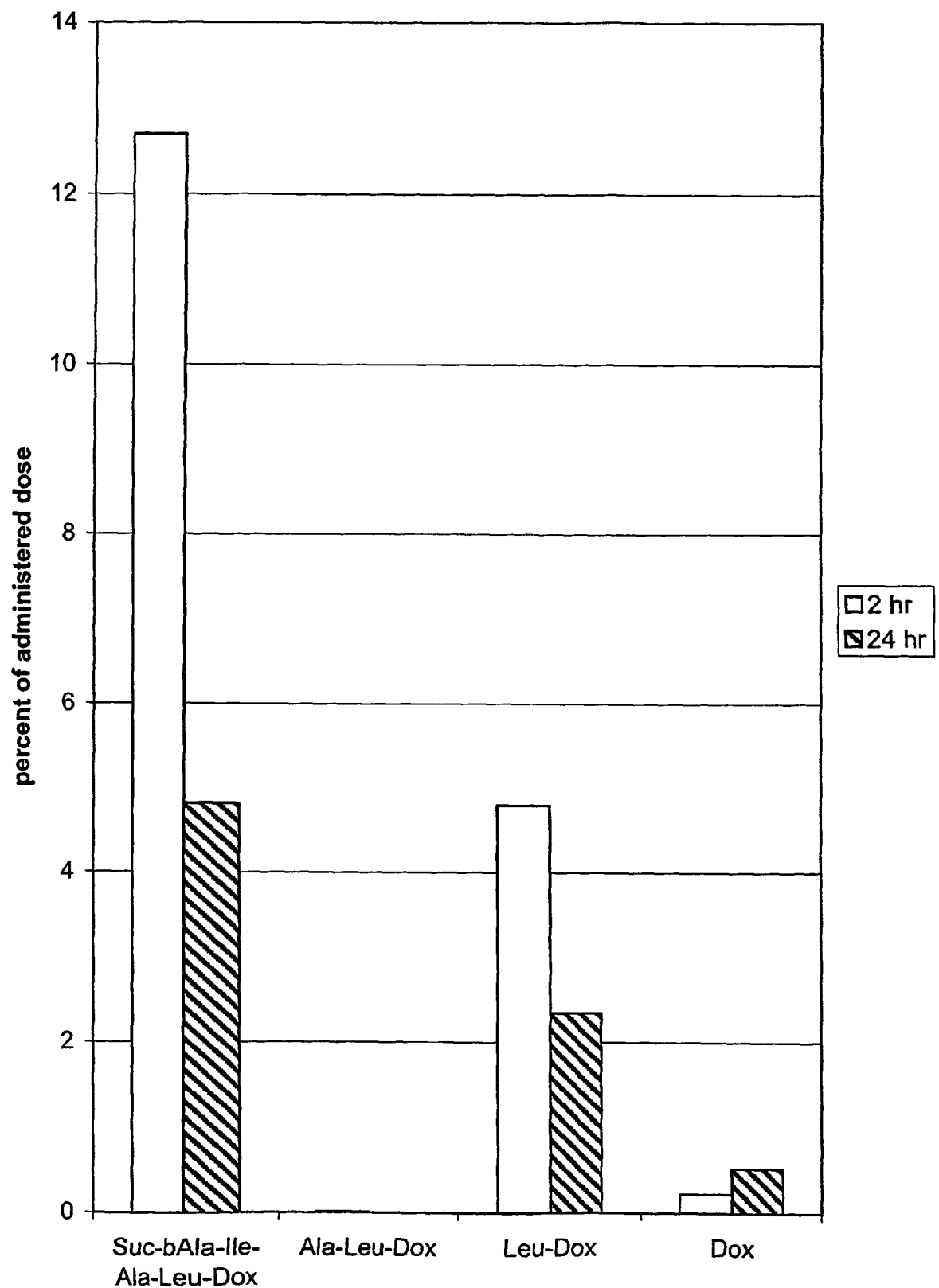
FIG. 14 is a graph of the amount of Suc-βAla-Ile-Ala-Leu-Dox (SEQ ID NO:39) and its metabolites present in the urine collected 0–2 and 2–24 hours after the administration of a single intravenous bolus of the prodrug.

Suc-βAla-Ile-Ala-Leu-Dox (SEQ ID NO:39) was cleared from the circulation very rapidly: approximately 1.0% of the administered dose could be detected in plasma at 1 hour, while it was virtually undetectable at 4 hours (Table 3 and FIG. 13). At 2 and 24 hours the urine contained 12.7% and 4.81 % of the administered dose, indicating that the kidney is a major organ of excretion for the prodrug (FIG. 14).

TABLE 3

|  | Plasma* | | Urine* | |
| --- | --- | --- | --- | --- |
|  | 1 hr | 4 hr | 2 hr | 24 hr |
| Suc-βAla-Ile-Ala-Leu-Dox (SEQ ID NO:39) | 1.03 | 0.00 | 12.7 | 4.81 |
| Ala-Leu-Dox | 0.00 | 0.00 | 0.01 | 0.00 |
| Leu-Dox | 0.04 | 0.00 | 4.69 | 2.29 |
| Dox | 0.01 | 0.00 | 0.21 | 0.51 |

*Percent of administered dose

The metabolite Ala-Leu-Dox was virtually undetectable in plasma, and was found at very low levels in urine at 2. The major peptide metabolite was Leu-Dox, which could be detected at low levels in plasma at 1 hour, as well as in urine at 2 hours and 24 hours. Little free doxorubicin was present in plasma however comparatively high levels were detected in urine, showing that some complete metabolism is occurring.

In these samples, the levels of both the parent and metabolites were higher in urine at 2 hours than at 24 hours. The sum of the amount of Suc-βAla-Ile-Ala-Leu-Dox (SEQ ID NO:39) and metabolites collected at 0–2 hours and 2–24 hours is similar to that of Suc-Ile-Ala-Leu-Dox (see Example 4). Thus, there is no physiologically significant difference between the clearance of Suc-βAla-Ile-Ala-Leu-Dox (SEQ ID NO:39) and Suc-Ile-Ala-Leu-Dox.

Example 7

Comparative Metabolism in Mice

In a second study, three groups of ICR normal female mice were administered a single IV bolus dose with approximately 100 μmol/Kg of Suc-βAla-Ile-Ala-Leu-Dox (SEQ ID NO: 39), Suc-Ile-Ala-Leu-Dox or 10 μ mol/Kg of doxorubicin (Dox). Plasma was obtained from three individual animals in each group at 5 minutes, 1, 2, 4, or 6 hr. Parent, dipeptidyl-doxorubicin (AL-Dox), α-aminoacyl-doxorubicin (L-Dox) and doxorubicin concentrations were analyzed in extracts of the plasma samples using a reverse phase gradient HPLC method with fluorescence detection ($\lambda_{ex}$=480 nm, $\lambda_{em}$=560). Quantities were determined using a linear standard curve fit to measurements of 10 to 2000 ng/mL doxorubicin solutions in mouse plasma.

Concentration time courses indicate that metabolic patterns were similar for both prodrug compounds. In particular, L-Dox was the major metabolite over the first two hr while the dipeptidyl-conjugate AL-Dox was a more minor product that formed at about the same time as L-Dox. Doxorubicin appeared later with the plasma concentration decreasing more slowly over time than the other metabolites as expected from the current and previously measured doxorubicin pharmacokinetic profiles and by the doxorubicin control group. This is not consistent with sequential cleavage profile from TOP/Trouase but is consistent with cleavage by another enzyme of some type of endopeptidase activity at the next amino acid. The activation is followed by sequential exopeptidase cleavage. A two fold decrease in exposure to doxorubicin is also observed with the tripeptide, Suc-Ile-Ala-Leu-Dox, compared to the corresponding tetrapeptide counterpart, Suc-βAla-Ile-Ala-Leu-Dox (SEQ ID NO:39). It should be noted that relative doxorubicin exposure after dosing these compounds is consistent with the relative safety observed in a maximum tolerated dose study in mice. Doxorubicin exposure was at least twice greater when the corresponding compounds having leucine in place of isoleucine was tested in the same experiment. This suggests that the high tolerance for the isoleucine compounds described in other examples can be explained by lower doxorubicin exposure.

TABLE 4

Plasma exposure expressed as $AUC_{0-6\ hr}$ of parent and peptolytic metabolites following 100 μmol/Kg single IV bolus injection of indicated peptidyl-doxorubicin compound or 10 μmol/Kg doxorubicin in normal mice.

| Dosed Compound | Parent μM · hr | AL-Dox (μM · hr) | L-Dox (μM · hr) | Dox (μM · hr) |
|---|---|---|---|---|
| Suc-βAla-Ile-Ala-Leu-Dox (SEQ ID NO:39) | 326 | 0.5 | 8.5 | 1.5 |
| Suc-Ile-Ala-Leu-Dox | 452 | 1.0 | 6.2 | 0.9 |
| Doxorubicin | N/A | N/A | N/A | 3.3 |

Example 8

Suc-βAla-Ile-Ala-Leu-Dox (SEQ ID NO:39) is Well Tolerated in Tumor Bearing Mice

Figure 15:
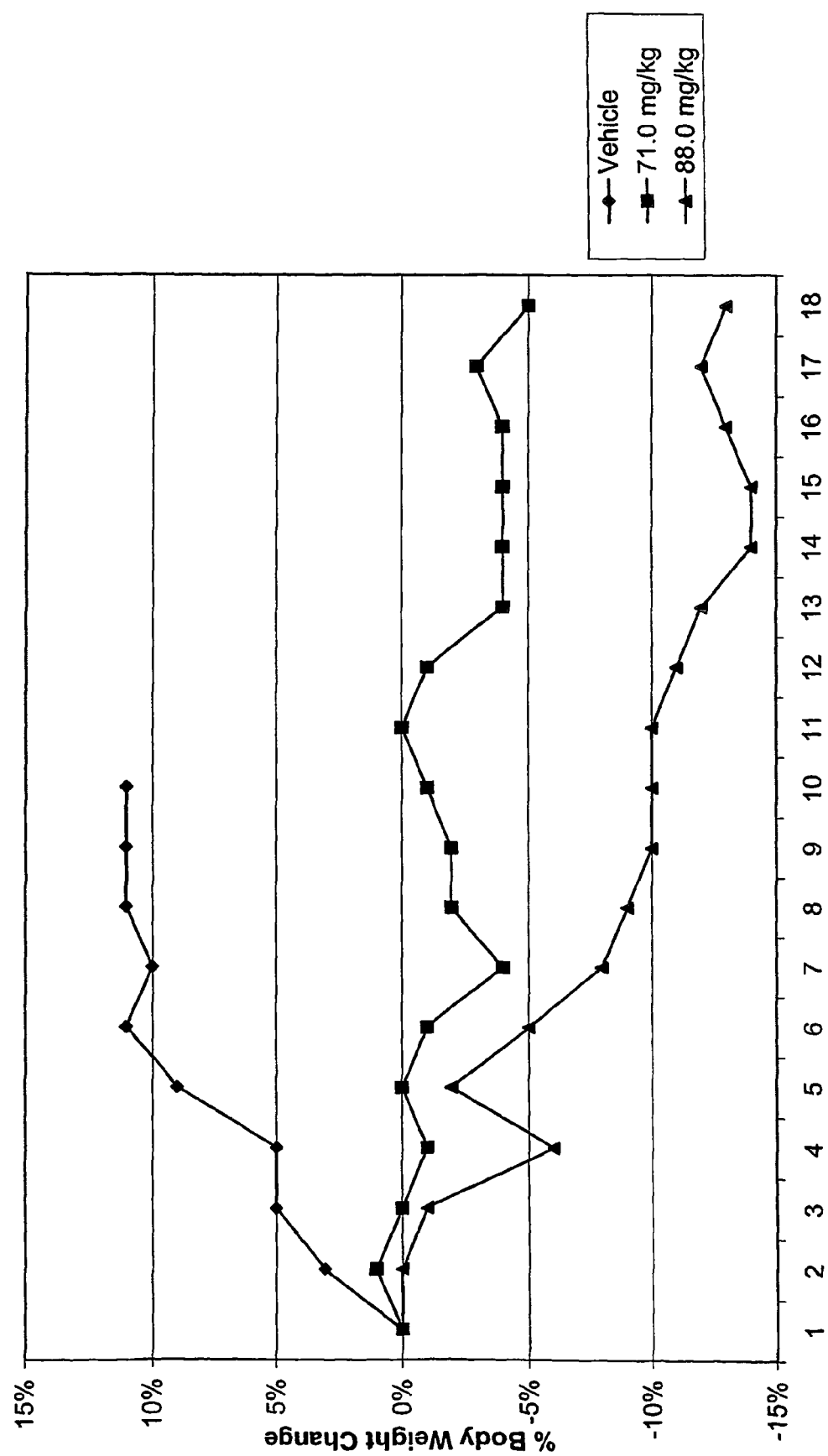
FIG. 15 is a graph of the Percent Body Weight Change of either mice treated with Suc-βAla-Ile-Ala-Leu-Dox (SEQ ID NO:39) or mice receiving the vehicle control.

The prodrug Suc-βAla-Ile-Ala-Leu-Dox (SEQ ID NO:39) therapeutic agent is significantly better tolerated than doxorubicin under repeat-dose conditions. As would be expected, when a dose similar to the single-dose MTD (75 mg/kg) (See Example 4) was administered as a repeat-dose it was less well tolerated. In repeat-dose studies in tumor bearing mice, three groups of ten mice were dosed with 0, 53 or 68 mg/kg Suc-βAla-Ile-Ala-Leu-Dox (SEQ ID NO:39) (equivalent to 0, 30 and 38 mg doxorubicin/kg), for a total five identical doses (Q5DX5) and observed frequently for 60 days. All treated animals lost weight progressively throughout the study, while the vehicle control group gained up to 12% of the mean initial body weight. (FIG. 15). Two treated animals in the high dose group were terminated due to signs of toxicity, with body weight loss of greater that 20% of their initial weight. The signs of toxicity were similar to those observed following a single, high dose (See Example 4) and were consistent with the known toxicity profile of doxorubicin in rodents. Thus cumulative toxicity resulted from repeat-dosing at these relatively high dose-levels. However the maximal overall exposures to doxorubicin of the animals in the two dose groups after 5 doses were 150 and 190 mg/kg, respectively, which is significantly higher (8 to 10 times) than the tolerated repeat dose level of doxorubicin (4 mg/kg, or 20 mg/kg total exposure after 5 doses). The RD-MTD of Suc-βAla-Ile-Ala-Leu-Dox (SEQ ID NO:39) was approximately 150 mg/kg doxorubicin equivalent which was at least 6.5-fold higher than the tolerated repeat dose level of doxorubicin (standard safe RD efficacious dose 4 mg/kg, or 20 mg/kg total exposure after 5 doses).

Example 9

Suc-βAla-Ile-Ala-Leu-Dox (SEQ ID NO:39) is Effective in Tumor Bearing Mice

Figure 16:
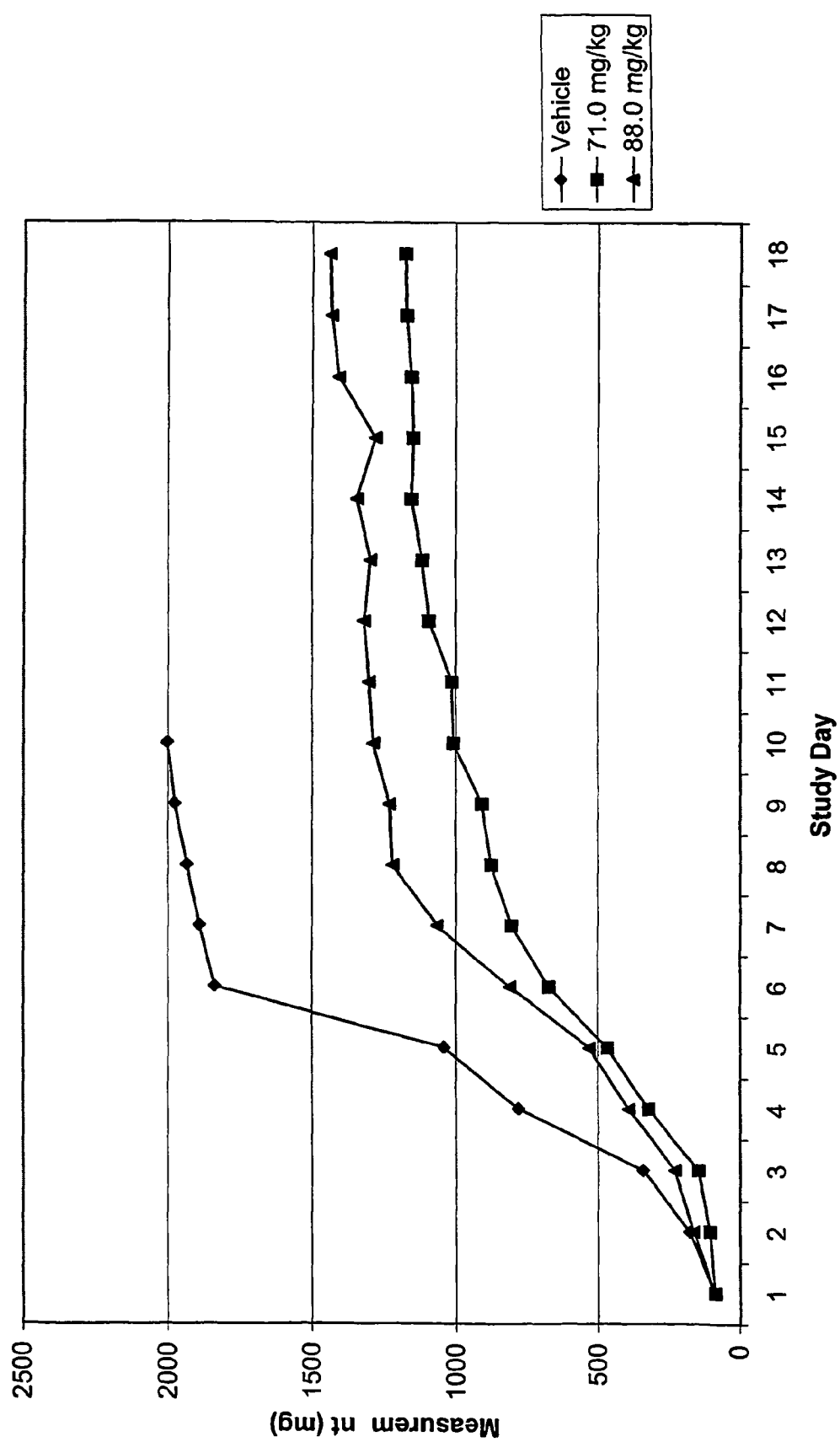
FIG. 16 is a graph of the rate of tumor growth in LS174T xenografted mice either treated with Suc-βAla-Ile-Ala-Leu-Dox (SEQ ID NO:39) or given the vehicle control.

The Suc-βAla-Ile-Ala-Leu-Dox (SEQ ID NO:39) therapeutic agent has proven to be efficacious in extending the survival of mice and inhibiting the growth of human tumors in a mouse xenograft model utilizing the doxorubicin-resistant colorectal carcinoma LS174t. For example, groups often nude mice, subcutaneously implanted with chunks of LS174t which were allowed to grow to approximately 90 mg, were treated intravenously with 0, 53 or 68 mg/kg of Suc-βAla-Ile-Ala-Leu-Dox (SEQ ID NO:39) (equivalent to 0, 30 or 38 mg/kg doxorubicin) at five day intervals for a total of five identical doses (Q5DX5). Tumors and body weights were measured twice weekly for up to 60 days. As seen in FIG. 16, both doses were efficacious in reducing the growth of tumors compared with vehicle control animals. There was a dose-dependent increase in number of mice surviving to the Day 60 end-point of the study. There were 2 and 4 long-term survivors in the low and high dose groups, respectively, compared with 0 in the vehicle control group. The Mean Day of Survival (MDS) in animals whose tumors reached 1.5 g prior to Day 60 was significantly better in the low (29.7 days) and high (23.4 day) dose groups than in the vehicle control group (18.2 days). Thus, Suc-βAla-Ile-Ala-Leu-Dox (SEQ ID NO:39) was efficacious in this aggressive human tumor model, in which doxorubicin alone at its tolerated dose (4 mg/kg), under this dosing regimen, is historically ineffective.

Re-review of the results showed that some of the results were incorrectly reported. There were 4 and 2 long-term survivors to the day 60 end-point in the low and high dose groups, respectively, compared with 0 in the vehicle control group. Suc-βAla-Ile-Ala-Leu-Dox (SEQ ID NO:39) was efficacious in this aggressive human tumor model, in which doxorubicin alone at its tolerated dose (3 mg/kg), under this dosing regimen, is historically ineffective.

Example 10

Suc-Ile-Ala-Leu-Dox is Better Tolerated in vivo Than Doxorubicin

Suc-Ile-Ala-Leu-Dox, an exemplary tripeptide prodrug of the invention, is well tolerated in mice. In a second single dose Maximum Tolerated Dose (SD-MTD) study, groups of five normal ICR mice were administered intravenously bolus doses of Suc-Ile-Ala-Leu-Dox. The mice were observed daily for 49 days and body weights measured twice weekly. Dose levels tested were 0, 94, 117, 140 or 164 mg/kg, equivalent to 0, 56, 70, 84 or 98 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the highest dose groups. Signs of toxicity were partial hind end paralysis at 164 mg/kg by Day 14, weight loss at 140 mg/kg by Day 14 in one animal and at 117 mg/kg by Day 21 also in one animal. Based on survival and lack of signs of toxicity at Day 49, the SD-MTD for Suc-Ile-Ala-Leu-Dox was determined to be 94 mg/kg (equivalent to 56 mg/kg of doxorubicin), which is 3.5-fold higher on a molar basis than the SD-MTD for doxorubicin alone (16 mg/kg). See TABLE 5. This is an approximate SD-MTD determination based on a range of doses at 14 mg/kg doxorubicin equivalents increments over the range tested.

TABLE 5

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-Ile-Ala-Leu-Dox | 94 | 58 | 3.5 |

Example 11

Suc-βAla-Ile-Ala-Leu-Dox (SEQ ID NO:39) is Better Tolerated in vivo Than Doxorubicin Suc-βAla-Ile-Ala-Leu-Dox (SEQ ID NO:39), an exemplary tetrapeptide prodrug of the invention, is well tolerated in mice. In a second single dose Maximum Tolerated Dose (SD-MTD) study, groups of five normal ICR mice were administered intravenous bolus doses of Suc-βAla-Ile-Ala-Leu-Dox. The mice were observed daily for 49 days and body weights measured twice weekly. Dose levels tested were 0, 50, 75 or 100 mg/kg, equivalent to 0, 28, 42 or 56 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the highest dose group. By Day 21, three animals in the 100 mg/kg dose were euthanized due to weight loss or paralysis. There was no morbidity or mortality observed in the 75 mg/kg dose group. Based on survival and lack of signs of toxicity at Day 49, the SD-MTD for Suc-βAla-Ile-Ala-Leu-Dox (SEQ ID NO:39) was determined to be 75 mg/kg (equivalent to 42 mg/kg of doxorubicin), which is 2.6-fold higher on a molar basis than the SD-MTD for doxorubicin alone (16 mg/kg). See TABLE 6. This is an approximate SD-MTD determination based on a range of doses at 14 mg/kg doxorubicin equivalents increments over the range tested.

TABLE 6

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-βAla-Ile-Ala-Leu-Dox (SEQ ID NO:39) | 75 | 42 | 2.6 |

Example 12

Advantages of Prodrugs Over the Unconjugated Therapeutic Agent

The prodrugs of the invention provide treatment advantages over the therapeutic agent in its unconjugated form.

In the single dose Maximum Tolerated Dose (MTD) studies, groups of normal mice were administered intravenous bolus doses of the prodrug. The mice were observed daily for 28 days and body weights measured twice weekly. The MTD was estimated to be equal to the highest dose that produced no death in mice after 28 days. As shown in Table 7, the single-dose MTD of the prodrugs range from 10-fold to at least 16-fold higher than that of doxorubicin alone.

TABLE 7

| Compound | SD MTD* (mg/kg) | Optimal Efficacy Repeat Dose (mg/kg) | Optimal Efficacy Dose Frequency | Major Plasma Metabolite |
|---|---|---|---|---|
| Suc-βAla-Ile-Ala-Leu-Dox (SEQ ID NO:39) | 75 (42) | 68 (38) | Q 5 days × 5 | Leu-Dox |
| Suc-Ile-Ala-Leu-Dox | >117 (70) | n.d. | n.d. | Leu-Dox |
| Suc-βAla-Leu-Ala-Leu-Dox (SEQ ID NO:74) | 75 (42) | 71.2 (40) | Q 1 week × 5 | Ala-Leu-Dox |
| Suc-Leu-Ala-Leu-Dox | >117 (70) | 63 (38) | Q 5 days × 5 | Leu-Dox |
| Doxorubicin | 4 (4) | 4 (4) | Q 1 week × 5 | n.a. | n.d. = not determined; n.a. = not applicable
(values in parentheses are the molar equivalent dose of doxorubicin)

In repeat-dose studies in tumor bearing mice, groups of ten mice were dosed with various amounts of prodrug for a total of five doses at either five day or 1 week intervals. After frequent observation over 60 days, the dose which proved to be within acceptable toxicity limits and produced an extension in survival was identified as the optimal efficacy repeat dose. As seen in Table 7, optimal efficacy repeat dose of the prodrugs are approximately 9-fold higher than that of doxorubicin alone. Thus, the prodrugs permit a much greater amount of therapeutic agent to be delivered to the body as a whole and thus to the vicinity of the target cell.

Post-analysis of compounds showed that they contained about 75% active compound due to water content and impurity. So the doses mentioned in the above paragraph overestimated amount of compound administered. As shown in Table 8 which shows corrected results, the SD-MTD of the isoleucine containing prodrugs range from 1.6-fold to 2.5-fold higher than that of doxorubicin alone. After frequent observation over 60 days, the dose which proved to be within acceptable toxicity limits was identified as the maximum tolerated repeat dose. As seen in Table 8, which shows corrected results RD-MTD of the prodrugs are approximately 6.5-fold higher than that of doxorubicin alone. Repeat dosing of the prodrugs at or lower than their RD-MTD significantly prolong survival of LS174t tumor bearing mice, whereas that of doxorubicin is completely ineffective. Thus, the conclusion remains the same in that the prodrugs permit a much greater amount of therapeutic agent to be delivered to the body as a whole and to the vicinity of the target cell.

TABLE 8

| Compound | SD MTD (mg/kg)* | Repeat Dose MTD (mg/kg)* | Repeat Dose Frequency | Major Plasma Metabolite |
|---|---|---|---|---|
| Suc-βAla-Ile-Ala-Leu-Dox (SEQ ID NO:39) | 75 (42) | 53 (30) | Q 5 D × 5 | Leu-Dox |
| Suc-Ile-Ala-Leu-Dox | 94 (56) | n.d. | n.d. | Leu-Dox |
| Suc-βAla-Leu-Ala-Leu-Dox (SEQ ID NO:74) | 50 (28) | 57 (32) | Q 7 D × 5 | Ala-Leu-Dox |
| Suc-Leu-Ala-Leu-Dox | 59 (35) | 52 (31) | Q 5 D × 5 | Leu-Dox |
| Doxorubicin | 16 (16) | 4 (4) | Q 7 D × 5 | n.a. | n.d. = not determine; n.a. = not applicable
*values in parentheses are the doxorubicin equivalent dose Analytical Methods for the Remaining Examples The peptide sequences, synthesized using either solid or solution phase approaches, were used without further purification if the analytical HPLC (methods A, B & D) showed the crude product to be greater than 80% pure. If not, the material was purified using preparative HPLC Method C.

HPLC Method A

Analytical HPLC analyses were performed on a Waters 2690 using a C-18 column (4 μm, 3.9×150 mm ID, flow rate 1 mL/min) eluting with a gradient of solvent A (0.1% TFA/H$_2$O) and solvent B (0.1% TFA/ACN) and the data was processed at λ254 nm using the Waters Millennium system. Analytical HPLC gradient started with 90% of solvent A and ended with 100% of solvent B over a period of 14 minutes (linear). Purity of the compounds for this method and the following ones was assessed as the relative percentage area under the curve of the peaks.

HPLC Method B

Analytical HPLC analyses were performed on a Waters 2690 using a C-8 column (3.5 μm, 4.6×150 mm ID, flow rate 1 mL/min) eluting with a gradient of solvent A (80% 20 mM ammonium formate and 20% acetonitrile) and solvent B (20% 20 mM ammonium formate and 80% acetonitrile) and the data was processed at λ254 nm using the Waters Millennium system. Analytical HPLC gradient started with 100% of solvent A to 100% of solvent B over a period of 30 minutes (linear).

HPLC Method C

Preparative purification of crude products was achieved using a Waters Delta Prep 4000 system using a C-4 column (15 μm, 40×100 mm ID, flow rate 30 mL/min) eluting with a gradient of solvent A (H$_2$O), and solvent B (MeOH). The preparatory HPLC gradient started with 80% of solvent A and goes to 100 % of solvent B over a period of 70 minutes (linear). UV detection was at λ254 run.

HPLC Method D

Analytical HPLC was accomplished on a Hewlett Packard instrument using a TSK superODS column (TosoHaas); solvent A (TFA 0.1% in water); solvent B (TFA 0.1% in acetonitrile); gradient: 30 to 36% of B in 2 minutes, 36 to 41% of B in 10 minutes, 41 to 90% of B in 3 minutes, 5 minutes at 90% B, detection wavelength λ254 nm.

NMR and MS

Additional structural determinations were done by NMR and MS techniques and the results supported the claimed compounds.

TLC Method

TLC analysis was carried out on silica gel 60F-254 nm-0.25 mm plates (Merck) with DCM/MeOH/H$_2$O/Formic acid 88% 85/15/1/2 for elution.

Ninhydrin Test

A few milligrams of product were introduced in a test tube, and two drops of Solution A (50 mg/mL ninhydrin in ethanol), two drops of Solution B (4 mg/mL phenol in ethanol), then two drops of Solution C (2 mL 0.01M KSCN, aqueous in 100 mL pyridine) were added. The mixture was left in a boiling water bath for five minutes. In the presence of a free amine the solution becomes purple.

Specific Oligopeptide Synthetic Examples

Sources of Commercially Available Reagents

Doxorubicin and Daunorubicin were supplied by Meiji (Japan), Pd(PPh$_3$)$_4$ by Strem chem (Newburyport, Mass.), PEG by Shearwater(Huntsville, Ala.), solvents, HATU by Aldrich (Milwaukee, Wis.); all resins and amino acids were supplied by ABI (Foster City, Calif.), Novabiochem (San Diego, Calif.), Advanced ChemTech (Louisville, Ky.), Peptide International (Louisville, Ky.), or SynPep (Dublin, Calif.).

Example 13

Synthesis of Fmoc-Ile-Ala-Leu-OH

Tripeptide (Fmoc-Ile-Ala-Leu-OH) was synthesized using solid-phase approach with standard Fmoc chemistry. A typical synthesis used Wang's alkoxy resin (0.60 mmol/gm loading). Fmoc-protected amino acids were used for solid-phase peptide synthesis.

For a scale of 1 mM peptide on resin, 3 equivalents of amino acid was preactivated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid using similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc-Ile-Ala-Leu-OH (92% HPLC purity by method A). Crude peptide was characterized by LC/MS and used for the next step without any further purification.

Example 14

Synthesis of Fmoc-β-Ala-Ile-Ala-Leu-OH (SEQ ID NO:37)

Tetrapeptide (Fmoc-β-Ala-Ile-Ala-Leu-OH) (SEQ ID NO:37) was synthesized using solid-phase approach with standard Fmoc chemistry. A typical synthesis used Wang's alkoxy resin (0.60 mmol/gm loading). Fmoc-protected amino acids were used for solid-phase peptide synthesis. For a scale of 1 mM peptide on resin, 3 equivalents of amino acid was preactivated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid using similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc-β-Ala-Ile-Ala-Leu-OH (SEQ ID NO:37) (92% HPLC purity by method A). Crude peptide was characterized by MS and used for the next step without any further purification.

Example 15

Synthesis of Fmoc-Ile-Ala-Leu-Dox

Doxorubicin.HCl (2.34 g, 4.03 mmol) and Fmoc-Ile-Ala-Leu-OH (2.4 g, 4.48 mmol) were dissolved at room temperature in anhydrous DMF (150 mL). To this rapidly stirred solution, DIEA (1.56 mL, 8.96 mmol) was added in one portion and the reaction mixture was stirred for 15 minutes at room temperature. The reaction mixture was cooled to 0° C. using an ice bath and 1.87 g (4.92 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-Ile-Ala-Leu-Dox (89% yield, 94% HPLC purity by method A). This product was characterized by MS and used for the next step without any further purification.

Example 16

Synthesis of Fmoc-β-Ala-Ile-Ala-Leu-Dox (SEQ ID NO:75)

Doxorubicin.HCl (1.43 g, 2.5 mmol) and yield Fmoc-β-Ala-Ile-Ala-Leu-OH (SEQ ID NO:37) (1.6 g, 2.6 mmol) were dissolved at room temperature in anhydrous DMF (150 mL). To this rapidly stirred solution, DIEA (1 mL, 5.7 mmol) was added in one portion and the reaction mixture was stirred for 15 minutes at room temperature. The reaction mixture was cooled to 0° C. using an ice bath and 1.07 g (2.8 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-β-Ala-Ile-Ala-Leu-Dox (SEQ ID NO:75) (88% yield, 92% HPLC purity by method A). This product was characterized by MS and used for the next step without any further purification.

Example 17

Synthesis of Suc-Ile-Ala-Leu-Dox from Fmoc-Ile-Ala-Leu-Dox

To a solution of Fmoc-Ile-Ala-Leu-Dox (4.4 g, 4.13 mmol) in 20 mL of dry DMF, piperidine (20.4 mL, 206 mmol) was added in one portion resulting in a color change from red to purple. The reaction mixture was stirred for 5 minutes at room temperature and then cooled to −20° C. using dry ice/acetone bath. 21.2 g (210 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-Ile-Ala-Leu-Dox (80% yield, 88% HPLC purity by method B). The final product was purified using prep HPLC method C and characterized by LC/MS which gave a molecular weight of 939 (expected molecular weight 940).

Example 18

Synthesis of Suc-β-Ala-Ile-Ala-Leu-Dox (SEQ ID NO:39) from Fmoc-β-Ala-Ile-Ala-Leu-Dox (SEQ ID NO:75)

To a solution of Fmoc-β-Ala-Ile-Ala-Leu-Dox (SEQ ID NO: 75) (4 g, 3.53 mmol) in 40 mL of dry DMF, piperidine (17.4 mL, 176 mmol) was added in one portion resulting in a color change from red to purple. The reaction mixture was stirred for 5 minutes at room temperature and then cooled to −20° C. using dry ice/acetone bath. 18 g (180 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-β-Ala-Ile-Ala-Leu-Dox (SEQ ID NO:39) (78% yield, 86% HPLC purity by method B). The final product was purified using prep HPLC method C and characterized by LC/MS which gave a molecular weight of 1011 (expected molecular weight 1012).

Example 19

Synthesis of Fmoc-β-Ala-Ile-Ala-Leu-OBn (SEQ ID NO:76)

The Fmoc-β-Ala-Ile-Ala-Leu (SEQ ID NO:37), (24.34 g, 0.04 mol) is added into a round bottom flask with DMF (350 mL) and a magnetic stirrer. After the tetrapeptide is dissolved, benzyl bromide (4.76 mL, 0.04 mol), followed by cesium carbonate (13.04 g, 0.04 mol), is added to the solution with stirring. The reaction mixture is stirred at room temperature for 1.5 hrs. Then, the reaction mixture is slowly poured into a flask with 450 mL of iced water. A large amount of white solid precipitates out which is collected by suction filtration. The product is washed with water (2×200 mL) and placed in a vacuum desiccator.

Example 20

Synthesis of β-Ala-Ile-Ala-Leu-Obn (SEQ ID NO:77)

In a round bottom flask (25 mL), Fmoc-β-Ala-Ile-Ala-Leu-Obn (SEQ ID NO:76) (0.7 g, 1.0 mmol) is dissolved in 5 mL of anhydrous DMF. Piperidine (1.2 mL, 12.1 mmol) is added to the solution and the mixture is stirred at room temperature for 25 minutes. The reaction is quenched with water (6 mL) and extracted with ethyl acetate (2×10 mL). The combined organic layer is further washed by water (2×5 mL), brine (5 mL) and dried over sodium sulfate. A white solid (0.8 g) is obtained after removal of solvent.

Example 21

Synthesis of MeOSuc-βAla-Ile-Ala-Leu-OBn (SEQ ID NO:78)

In a round bottom flask (250 mL), methyl hemisuccinate (3.19 g, 24.2 mmol) is dissolved in anhydrous DMF (50 mL). DIEA (4.22 mL, 24.2 mmol) followed by HBTU (9.17 g, 24.2 mmol) are added into the solution. The mixture is stirred at room temperature for 45 minutes. To this mixture is added a solution of βAla-Ile-Ala-Leu-Obn (SEQ ID NO:77) (crude, containing 10.14 g, 21.3 mmol) in anhydrous DMF (150 mL). The mixture is continually stirred at room temperature for 2.5 hrs. Then, the reaction mixture is slowly poured into a flask with 200 mL of iced water while stirring. A large amount of white solid precipitates out which is extracted by ethyl acetate (3×200 mL). The combined organic layer is further washed by water (2×200 mL), brine (200 mL) and dried over sodium sulfate.

Example 22

Synthesis of MeOSuc-βAla-Ile-Ala-Leu (SEQ ID NO:47)

MeOSuc-βAla-Ile-Ala-Leu-OBn (SEQ ID NO: 78) (1.0 g; 1.46 mmol) is added into an Erlenmeyer flask with 100 mL of methanol. 50 mL of methanol is added. The solution is transferred into a hydrogenation reaction vessel. To this vessel, Pd-C (90 mg, 10% wet, 50% water; 0.042 mmol) is added. After hydrogenation for 2 hours at room temperature, the reaction is stopped and the catalyst is filtered.

Example 23

Coupling of MeOSuc-βAla-Ile-Ala-Leu (SEQ ID NO: 47) and Doxorubicin Using the "Urea Method"

Under dry nitrogen atmosphere, 26.04 g (52.0 mmol) MeOSuc-βAla-Ile-Ala-Leu (SEQ ID NO:47) and 23.26 g (40.2 mmol) doxorubicin hydrochloride are suspended/dissolved in 800 mL dry, urea-saturated (~30% w/v) DMF and 19.948 mL DIEA. This mixture is cooled to 0–3° C. over ~25 minutes. At this point 21.2 g (56.0 mmol) HATU is added as a solution in ~100 mL urea saturated DMF over 10 minutes (the volume of this solution should be kept minimal). The reaction mixture is stirred for 10 minutes at −2 to 2° C. and poured into 4000 mL ice cold brine, containing 2% v/v acetic acid over approximately five minutes with vigorous stirring. The product is filtered off on a medium porosity fritted glass filter, washed generously with water and dried under reduced pressure.

Example 24

Synthesis of MeOSuc-βAla-Ile-Ala-Leu-Dox (SEQ ID NO: 48) Therapeutic Agent

In a round bottom flask (50 mL), MeOSuc-βAla-Ile-Ala-Leu (SEQ ID NO: 47) (0.25 g, 0.5 mmol) and doxorubicin (0.29 g, 0.5 mmol) are dissolved in anhydrous DMF (20 mL). After the mixture is stirred for 5 minutes, DIEA (0.17 mL, 1.0 mmol) followed by HBTU (0.19 g, 0.5 mmol) is added into the solution. The mixture is stirred at room temperature for 4 hrs. DMF is removed by a rotary evaporator and the residue is taken up in 4.0 mL 1:1 methylenechloride:methanol. To this solution, 40 mL of ether is slowly added while stirring. A precipitate is formed and collected by suction filtration. The solid is washed with ether (2×10 mL) and dried in a vacuum desiccator.

Example 25

Removal of Free Doxorubicin from MeOSuc-β-Ala-Ile-Ala-Leu-Dox (SEQ ID NO:48)

MeOSuc-β-Ala-Ile-Ala-Leu-Dox (SEQ ID NO:48) (200 mg, 0.194 mmol), DIEA (0.068 mL, 0.388 mmol) and anhydrous DMF (10 mL) are placed in a 50 ml flask equipped with a magnetic stir bar. When MeOSuc-β-Ala-Ile-Ala-Leu-Dox (SEQ ID NO:48) had completely dissolved, isocyanate resin (390 mg, 0.582, pre-swollen in 5 mL of dichloromethane for 5 minutes) is added and the resulting solution is stirred for 2 h at room temperature with periodic HPLC monitoring. The reaction mixture is then filtered through a frit to remove the resin when HPLC traces indicate that the Dox is completely removed. The resin is washed with 10 ml DMF and the DMF washes are combined with the filtered reaction mixture. The filtered reaction mixture washes are then concentrated on a rotary evaporator equipped with a high vacuum pump and a 30° C. water bath. The residue is suspended in 5 ml of DMF and the solution is then slowly added into a rapidly stirred anhydrous diethylether solution. The product is then filtered over a frit and washed with diethylether and dried under reduced pressure to give MeOSuc-β-Ala-Ile-Ala-Leu-Dox (SEQ ID NO:48).

Example 26

Hydrolysis of the MeOSuc-βAla-Ile-Ala-Leu-Dox (SEQ ID NO:48) Therapeutic Agent via Use of Cross Linked Enzyme MeOSuc-βAla-Ile-Ala-Leu-Dox (SEQ ID NO:48) therapeutic agent (1.0 g, 0.975 mmol) and 100 mL DMF are placed in a 500 mL flask. The suspension is vigorously agitated with a magnetic stirrer. When the MeOSuc-βAla-Ile-Ala-Leu-Dox (SEQ ID NO: 48) therapeutic agent has completely dissolved, 400 mL deionized water is added and the resulting solution stirred at 35° C. A slurry of 1 g washed CLEC-PC (Altus Biologics) the immobilized enzyme is rinsed in three aliquots of deionized water then resuspended in 10 mL 20% aqueous DMF prior to use. The resulting suspension is stirred at 35° C. with periodic HPLC monitoring. When all of the MeOSuc-βAla-Ile-Ala-Leu-Dox (SEQ ID NO:48) therapeutic agent has been consumed, the reaction mixture is filtered through a 0.45 μM nylon membrane filter to remove the CLEC-PC enzyme. The CLEC-PC cake is washed with 3×10 mL methanol and the methanol washes are combined with the filtered reaction mixture. The filtered reaction mixture plus methanol washes are then concentrated to a red gum on a rotary evaporator equipped with a high vacuum pump and a 30° C. water bath. The red gum is then suspended in 50 mL deionized water at room temperature and rapidly stirred via mechanical stirrer. To this suspension a solution of 77.8 mg sodium bicarbonate (0.926 mmol, 0.95 eq.) in 100 mL deionized water is added over 2 minutes. The suspension is stirred at room temperature 20 minutes. The reaction mixture is filtered through a 0.45 μM nylon membrane filter and lyophilized.

Example 27

Hydrolysis of the MeOSuc-βAla-Ile-Ala-Leu-Dox (SEQ ID NO:48) Therapeutic Agent via Use of Soluble Enzyme 11.0 g (10.72 mmol) MeOSuc-βAla-Ile-Ala-Leu-Dox (SEQ ID NO:48) therapeutic agent is suspended in 800 mL HPLC-grade water and homogenized for 60 minutes with an Ultraturrax T8 homogenizer to yield a finely divided suspension. This suspension is stirred (500 rpm) at 35° C. and adjusted to pH=6.05 with aq. 76 mM NaHCO$_3$. 1.0 g C. Antarctica "B" lipase (Altus Biologics) is then added and the reaction mixture stirred at 35° C. for 48 hours. During the 48 hr reaction time, pH is maintained between 5.3 and 6.2 by periodic addition of 76 mM NaHCO$_3$ and the reaction is periodically monitored by HPLC. After the reaction is nearly complete, the reaction mixture is then adjusted to pH=7 with aq. 76 mM NaHCO$_3$ and filtered through a pad of Celite 521. The clarified reaction mixture is then acidified to ca. pH 3 with 5 mL glacial acetic acid. The precipitate is isolated by Celite 521 filtration, subsequently rinsing the Celite pad with methanol. The methanol solution is filtered through a 10–20 μM fritted glass filter and is dried by rotary evaporation. This product is converted to the sodium salt by dissolution in 70 mL 76 mM NaHCO$_3$ (0.95 eq.) and lyophilized. The product is identical to that of Example 26.

Example 28

Immobilized *Candida Antarctica* "B" Lipase Hydrolysis of MeOSuc-βAla-Ile-Ala-Leu-Dox (SEQ ID NO:48) Therapeutic Agent 30.0 g *Candida Antarctica* "B" lipase (Altus Biologics) is dissolved in 300 mL water and dialyzed against 3×4 1 of 50 mM aq. NaHCO$_3$ (pH=6.4). 360 mL of Pharmacia NHS-Activated Sepharose 4 Fast Flow is placed in a coarse glass fritted funnel and rinsed with 5×450 mL ice-cold 1 mM aq. HCl. The rinsed NHS-Activated Sepharose is then combined with the dialyzed enzyme solution. The resulting suspension is stirred at ambient temperature (ca. 22° C.) for 2.0 hours. The Sepharose/enzyme conjugate is then isolated on a coarse fritted glass filter and then stirred in 1000 mL 100 mM aq. TRIS (pH=7.45) for 15 minutes. This suspension is filtered and incubated with another 1000 mL 100 mM aqueous TRIS buffer (pH=7.45) at 4° C., overnight. In the morning, the immobilized enzyme is filtered off and after washing with water, is placed into a 2000 mL three necked, round bottomed flask. 43 g MeOSuc-βAla-Ile-Ala-Leu-Dox (SEQ ID NO:48) therapeutic agent is added and the solids are suspended in 800 mL deionized water. The flask is fitted with an overhead stirrer, and a pH-stat set to keep the pH of the reaction mixture between 5.9–6.2 by controlling a syringe pump. The syringe pump is charged 0.1 M NaHCO$_3$. Progress of the reaction is followed by HPLC. After the reaction is nearly complete, the immobilized enzyme is filtered off and the liquid phase is lyophilized. The dry solids are then suspended in about 11 mL dry THF and filtered off.

Example 29

Large Scale Synthesis of Methyl Succinyl-N-Cap Form of βAla-Ile-Ala-Leu-Dox (SEQ ID NO:40) Therapeutic Agent 120 mmol Doxorubicin.HCl and 199 mmol MeOSuc-βAla-Ile-Ala-Leu (SEQ ID NO:47) is dissolved in anhydrous DMF (10 L) under nitrogen. 76 mL DIEA (434 mmol) is added to the reaction mixture and the reaction mixture is stirred for 10 minutes at room temperature under nitrogen. The reaction mixture is then cooled to 0° C. over 10 minutes. In a separate flask a solution of 864 g HATU (220 mmol) in DMF (500 mL) is prepared. The HATU solution is added slowly over 20 minutes to the reaction mixture while the reaction mixture is maintained at 0° C. The reaction mixture is stirred at 0° C. for 30 minutes.

A solution of NaCl (7.5 Kg, at least 30% w/v) in water (25 L) is prepared and cooled to 0° C. The reaction mixture is then slowly added to the cooled brine solution with vigorous stirring over 120 minutes. The color of the solution must remain red, a blue solution indicates that the pH needs adjustment immediately to between 5.8–6.0 by adding acetic acid. The temperature is maintained at approximately 5° C. The red precipitate is filtered off on a medium porosity fritted glass filter, washed with water and dried under vacuum pressure over P$_2$O$_5$ to yield MeOSuc-βAla-Ile-Ala-Leu-Dox (SEQ ID NO:48).

Example 30

Treatment of MeOSuc-βAla-Ile-Ala-Leu-Dox (SEQ ID NO:48) With Ps-isocyanate Beads to Remove Traces of Doxorubicin 146.4 g PS-isocyanate beads (240 mmol; supplied by Argonaut Lab, San Carlos, Calif.) are dissolved in 1.5 L of anhydrous DMF and allowed to swell for 5–10 minutes at room temperature. The swelled beads are filtered through a glass-fritted funnel and washed with additional 500 mL of anhydrous DMF. 112 mmol MeOSuc-βAla-Ile-Ala-Leu-Dox (SEQ ID NO:48) is dissolved in 1000 mL of anhydrous DMF and 12 mmol mL DIEA is added followed by the swelled PS-isocyanate beads. The reaction mixture is stirred at room temperature and is monitored using HPLC till the amount of doxorubicin peak is less than 0.1%. Analytical HPLC analyses are performed using Water 2690 Column: Waters Symmetry Shield $C_8$ 3.5 μM 4.6×150 mm (cat #WAT094269), solvent: A-80% aqueous 20 mM ammonium formate (pH=4.5) 20% acetonitrile, solvent: B-20% aqueous 20 mM ammonium formate (pH=4.5) 80% acetonitrile. Column temperature: controlled room temperature, sample Temperature 4° C., Run time: 37.5 minutes, detector: 254 nm, Flow rate: 1.0 mL/min, Injection amount 10 μg (0.5 mg/mL×0.02 mL), Mobile Phase A and B. Gradient: 37.5 minute linear gradient from 100% mobile phase A to 100% mobile phase B with a 7.5 minute equilibration delay.

When the doxorubicin peak is less than 0.1%, the reaction mixture is filtered through a coarse sintered glass funnel to remove the beads. A brine solution (at least 30% w/v) of 1.1 kg NaCl in 3.5 L water is prepared and cooled to 0° C. The filtered reaction mixture is then slowly added to the cooled brine solution with vigorous stirring over 45 minutes. The color of the solution must remain red, a blue solution indicates that the pH needs adjustment immediately to between 5.8–6.0 by adding acetic acid. The red precipitate is filtered through a medium sintered glass funnel, washed with water and dried under vacuum pressure over $P_2O_5$ to yield MeOSuc-βAla-Ile-Ala-Leu-Dox (SEQ ID NO:48) free of any residual doxorubicin.

MeOSuc-βAla-Ile-Ala-Leu-Dox (SEQ ID NO:48) is dissolved in 1 L MeOH and the methanol solution is then slowly added to 14L of cooled ethyl ether with vigorous stirring over 60 minutes. The red precipitate is filtered through a medium sintered glass funnel, washed with ether (1 L) and dried under vacuum pressure to yield MeOSuc-βAla-Ile-Ala-Leu-Dox (SEQ ID NO:48). The purity is determined by HPLC, as described in Example 29.

Example 31

Enzymatic Hydrolysis of MeOSuc-βAla-Ile-Ala-Leu-Dox (SEQ ID NO:48) to Yield Suc-βAla-Ile-Ala-Leu-Dox (SEQ ID NO:39)

The CLEC-CAB (*Candida Antartica* "B" Lipase) enzyme is purchased (from Altus Biologics., Boston, Mass.) in solution form, where the concentration of the enzyme is defined by the weight of dry enzyme per milliliter of solution. The crude enzyme suspension is shaken for few minutes to obtain a homogenous solution. 504 mL (328 mmol) of this homogenous solution is aliquoted into a flask. 2.5 L of deionized water is added and the slurry is stirred for 10 minutes using a magnetic stirrer. The enzyme solution is filtered using a coarse glass fritted funnel, without taking the enzyme to dryness. The enzyme is transferred back into a flask. The enzyme is suspended in water and filtered three more times.

The enzyme cake is resuspended into 550 mL of deionized water and transferred into a RB flask. To this suspension, MeOSuc-βAla-Ile-Ala-Leu-Dox (SEQ ID NO:48) (106 mmol) is added and the reaction mixture is stirred at room temperature (25° C.). The pH of the reaction mixture is maintained between 5.8 and 6.1 by a pH-stat equipped with a syringe pump charged with 1 N $NaHCO_3$ solution. Progress of the reaction is followed with periodic HPLC monitoring, as described in Example 29. The reaction is continued until the reaction seems to be complete, as determined by HPLC.

To speed up the reaction, additional CLEC enzyme is required when the reaction is complete. Additional CLEC enzyme (homogenous solution) is washed in a column format as described above. The enzyme cake is resuspended into 1.1 L of deionized water and added to the reaction mixture. The reaction mixture is stirred at room temperature with periodic HPLC monitoring and the pH is maintained between 5.8 and 6.1.

Once the reaction is complete, the CLEC enzyme is removed from the reaction mixture by filtration through a 0.2 μM filter and rinsed with 500 mL of deionized water. The filtrate is then lyophilized to yield Suc-βAla-Ile-Ala-Leu-Dox.Na (SEQ ID NO:39).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound comprising:
(1) a therapeutic agent capable of entering a target cell,
(2) an oligopeptide of the formula $(AA)_n\text{-}AA^3\text{-}AA^2\text{-}AA^1$, wherein:
   $AA^1$ is selected from the group consisting of Leucine, Phenylalanine, Isoleucine, Alanine, Glycine, Tyrosine, 2-Naphthylalanine, Serine, Proline, and β-Alanine,
   $AA^2$ represents any amino acid,
   $AA^3$ represents isoleucine,
   n is 0 or 1, and when n is 1 then $(AA)_n$ is $AA^4$ which represents any amino acid,
(3) a negatively charged stabilizing group, and
(4) optionally, a linker group not cleavable by TOP, wherein:
   the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
   wherein the stabilizing group hinders cleavage of the compound by enzymes present in whole blood, and
   wherein the compound is cleavable by an enzyme associated with the target cell, the enzyme associated with the target cell being other than TOP,
or a salt of said compound.

2. A compound comprising:
(1) a therapeutic agent capable of entering a target cell,
(2) an oligopeptide of the formula $(AA)_n\text{-}AA^3\text{-}AA^2\text{-}AA^1$, wherein:
   $AA^1$ is selected from the group consisting of Leucine, Phenylalanine, Isoleucine, Alanine, Glycine, Tyrosine, 2-Naphthylalanine, Serine, Proline, and β-Alanine,
   $AA^2$ is selected from group consisting Alanine, Leucine, Glycine, Serine, 3-Pyndylalanine, 2-Thienylalanine, Tyrosine, N-Methylalanine, Aminoisobutyric Acid, Threonine, and Phenylalanine,
   $AA^3$ represents isoleucine, and
   n is 0 or 1, and when n is 1, then $(AA)_n$ is $AA^4$ which represents any amino acid,
(3) a neutral stabilizing group or a negatively charged stabilizing group, and
(4) optionally, a linker group not cleavable by TOP,
   wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
   wherein the stabilizing group hinders cleavage of the compound by enzymes present in whole blood, and
   wherein the compound is cleavable by an enzyme associated with the target cell, the enzyme associated with the target cell being other than TOP, or a salt of said compound.

3. The compound of claim 1 or 2, wherein the compound is resistant to cleavage by TOP.

4. The compound of claim 1 wherein $AA^2$ of the oligopeptide is selected from Alanine, Leucine, Glycine, Serine, Tyrosine, 3-Pyridylalanine, 2-Thienylalanine, N-Methylalanine, Aminoisobutyric Acid, Threonine, and Phenylalanine.

5. The compound of claim 1 or 2, wherein $AA^4$ is selected from the group consisting of β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aininomethylbenzoic acid, and Aminoisobutyric acid.

6. The compound of claim 1 or 2, wherein the oligopeptide is βAla-Ile-Ala-Leu (SEQ ID NO:8).

7. The compound of claim 1 or 2, wherein the stabilizing group is a dicarboxylic or higher order carboxylic acid.

8. The compound of claim 1, wherein the stabilizing group is selected from the group consisting of succinic acid, adipic acid, glutaric acid, phthalic acid, diglycolic acid, fumaric acid, naphthalene dicarboxylic acid, 1,8-naphthyl dicarboxylic acid, aconitic acid, carboxycinnamic acid, triazole dicarboxylic acid, 4-carboxyphenyl boronic acid, butane disulfonic acid, and maleic acid.

9. The compound of claim 1 or 2, wherein the stabilizing group is one of aspartic acid linked to the oligopeptide at the β-carboxy group of the aspartic acid or glutamic acid linked to the oligopeptide at the γ-carboxy group of the glutamic acid.

10. The compound of claim 1 or 2, wherein the enzyme associated with the target cell cleaves the linkage between $AA^1$ and $AA^2$ of the oligopeptide.

11. The compound of claim 1 or 2, wherein the oligopeptide is directly linked to the therapeutic agent.

12. The compound of claim 1 or 2, wherein the oligopeptide sequence is indirectly linked to the therapeutic agent at the second attachment site of the oligopeptide via a linker group, the linker group selected from amino caproic acid, hydrazide group, an ester group, an ether group, or a suifflydryl group.

13. The compound of claim 1 or 2, wherein the therapeutic agent is selected from the group consisting of Alkylating Agents, Antiproliferative agents, Tubulin Binding agents, Vinca Alkaloids, Enedjynes, Podophyllotoxins or Podophyllotoxin derivatives, the Pteridine family of drugs, Taxanes, Anthracyclines, Dolastatins, Topoiosomerase inhibitors, and Platinum coordination-complex chemotherapeutic agents.

14. The compound of claim 1 or 2, wherein the therapeutic agent is selected from Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin $A_4$ Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine arabinoside, Colchicine, Cisplatin, Carboplatin, Bleomycin, Melphalan, Chloroquine, Cyclosporin A, a derivative of any of the foregoing and an analog of any of the foregoing.

15. The compound of claim 1 or 2, wherein the therapeutic agent has an intracellular active site.

16. The compound of claim 1 or 2, wherein the compound is selected from the group consisting of: Suc-βAla-Ile-Ala-Leu-Dnr (SEQ ID NO: 43), Suc-βAla-Ile-Ala-Leu-Dox (SEQ ID NO: 39), Suc-Ile-Ala-Leu-Dox, Suc-Ile-N(Me) Ala-Leu-Dox, and Suc-Ile-Ala-Gly-Dox.

17. The compound of claim 1 or 2, wherein the target cell is a tumor cell or inflammatory cell.

18. The compound of claim 1 or 2, wherein the enzyme associated with the target cell is present in the extracellular vicinity of the target cell for the therapeutic agent.

19. The compound of claim 2 wherein the stabilizing group is negatively charged.

20. The compound of claim 2, wherein the stabilizing group is selected from the group consisting of succinic acid, adipic acid, glutaric acid, phthalic acid, diglycolic acid, fumaric acid, naphthalene dicarboxylic acid, pyroglutamic acid, acetic acid, 1-naphthylcarboxylic acid, 2-naphthylcarboxylic acid, 1,8-naphthyl dicarboxylic acid, aconitic acid, carboxycinnamic acid, triazole dicarboxylic acid, gluconic acid, 4-carboxyphenyl boronic acid, butane disulfonic acid, and maleic acid.

21. A compound comprising:
(1) a therapeutic agent capable of entering a target cell,
(2) an oligopeptide of the formula $(AA)_n$-$AA^3$-$AA^2$-$AA^1$, wherein:
    $AA^1$ is selected from the group consisting of Leucine, Phenylalanine, Isoleucine, Alanine, Glycine, Tyrosine, 2-Naphthylalanine, Seine, Proline, and β-Alanine,
    $AA^2$ represents any amino acid,
    $AA^3$ represents isoleucine,
    n is 0 or 1, and when n is 1, then $(AA)_n$ is $AA^4$ which represents any amino acid,
(3) a stabilizing group, the stabilizing group selected from
    (a) a dicarboxylic or higher order carboxylic acid,
    (b) a non-genetically encoded amino acid having four or more carbons, or
    (c) one of aspartic acid linked to the oligopeptide at the β-carboxy group of the aspartic acid or glutamic acid linked to the oligopeptide at the γ-carboxy group of the glutamic acid, and
(4) optionally, a linker group not cleavable by a trouase, wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by an enzyme associated with the target cell, the enzyme associated with the target cell being other than a trouase or a salt of said compound.

22. The compound of claim 21 wherein the compound is resistant to cleavage by a trouase.

23. The compound of claim 21 wherein the stabilizing group is selected from the group consisting of: succinic acid, adipic acid, glutaric acid, phthalic acid, diglycolic acid, fumaric acid, naphthalene dicarboxylic acid, pyroglutamic acid, 1,8-naphthyl dicarboxylic acid, aconitic acid, carboxycinnamic acid, triazole dicarboxylic acid, and maleic acid.

24. The compound of claim 21 wherein the stabilizing group is selected from the group consisting of: Thiazolidine-4-carboxylic acid, 2-Thienylalanine, 2-Naphthylalanine, D-Leucine, D-Methionine, D-Phenylalanine, 3-Amino-3-phenyipropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

25. A pharmaceutical composition comprising
(1) a compound including
    (a) a therapeutic agent capable of entering a target cell,
    (b) an oligopeptide of the formula $(AA)_n$-$AA^3$-$AA^2$-$AA^1$, wherein:
        $AA^1$ is selected from the group consisting of Leucine, Phenylalanine, Isoleucine, Alanine, Glycine, Tyrosine, 2-Naphthylalanine, Serine, Proline, and β-Alanine,
        $AA^2$ represents any amino acid,
        $AA^3$ represents isoleucine,
        n is 0 or 1, and when n is 1, then $(AA)_n$ is $AA^4$ which represents any amino acid,
    (c) a negatively charged stabilizing group, and
    (d) optionally, a linker group not cleavable by TOP,
    wherein the oligopeptide is directly linked to the stabilizing group at a first attachment site of the oligopeptide and $AA^1$ of the oligopeptide is directly linked to the therapeutic agent or indirectly linked through the linker group to the therapeutic agent at a second attachment site of the oligopeptide,
    wherein the stabilizing group hinders cleavage of the compound by enzymes present in whole blood, and
    wherein the compound is cleavable by an enzyme associated with the target cell, the enzyme associated with the target cell being other than TOP, or a salt of said compound and
(2) a pharmaceutically acceptable carrier.

26. A pharmaceutical composition comprising
(1) a compound including
    (a) a therapeutic agent capable of entering a target cell,
    (b) an oligopeptide of the formula $(AA)_n$-$AA^3$-$AA^2$-$AA^1$, wherein:
        $AA^1$ is selected from the group consisting of Leucine, Phenylalanine, Isoleucine, Alanine, Glycine, Tyrosine, 2-Naphthylalanine, Serine, Proline, and β-Alanine,
        $AA^2$ is selected from the group consisting of Alanine, Leucine, Glycine, Serine, 3-Pyridylalanine, 2-Thienylalanine, Tyrosine, N-Methylalanine, Aminoisobutyric Acid, Threonine, and Phenylalanine,
        $AA^3$ represents isoleucine, and
        n is 0 or 1, and when n is 1, then $(AA)_n$ is $AA^4$ which represents any amino acid,
    (c) a neutral stabilizing group or a negatively charged stabilizing group, and
    (d) optionally, a linker group not cleavable by TOP,
    wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
    wherein the stabilizing group hinders cleavage of the compound by enzymes present in whole blood, and
    wherein the compound is cleavable by an enzyme associated with the target cell, the enzyme associated with the target cell being other than TOP, or a salt of said compound, and
(2) a pharmaceutically acceptable carrier.

27. The pharmaceutical composition of claim 25 or 26, wherein the compound is resistant to cleavage by TOP.

28. A method for treating a patient, the method comprising:
administering a therapeutically effective amount of a compound comprising:
(1) a therapeutic agent capable of entering a target cell,
(2) an oligopeptide of the formula $(AA)_n$-$AA^3$-$AA^2$-$AA^1$, wherein:

AA$^1$ is selected from the group consisting of Leucine, Phenylalanine, Isoleucine, Alanine, Glycine, Tyrosine, 2-Naphthylalanine, Serine, Proline, and β-Alanine, AA$^2$ represents any amino acid, AA$^3$ represents isoleucine, n is 0 or 1, and when n is 1 then (AA)$_n$ is AA$^4$ which represents any amino acid, (3) a negatively charged stabilizing group, and (4) optionally, a linker group not cleavable by TOP, or a salt of said compound wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the compound by enzymes present in whole blood, and wherein the compound is cleavable by an enzyme associated with the target cell, the enzyme associated with the target cell being other than TOP, such that the patient is treated.

29. A method for treating a patient, the method comprising:

administering a therapeutically effective amount of a compound comprising:

(1) a therapeutic agent capable of entering a target cell, (2) an oligopeptide of the formula (AA)$_n$-AA$^3$-AA$^2$-AA$^1$, wherein:

AA$^1$ is selected from the group consisting of Leucine, Phenylalanine, Isoleucine, Alanine, Glycine, Tyrosine, 2-Naphthylalanine, Serine, Proline, and β-Alanine, AA$^2$ is selected from the group consisting of Alanine, Leucine, Glycine, Serine, 3-Pyridylalanine, 2-Thienylalanine, Tyrosine, N-Methylalanine, Aminoisobutyric Acid, Threonine, and Phenylalanine, AA$^3$ represents isoleucine, and n is 0 or 1, and when n is 1, then (AA)$_n$ is AA$^4$ which represents any amino acid, (3) a neutral stabilizing group or a negatively charged stabilizing group, and (4) optionally, a linker group not cleavable by TOP, wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the compound by enzymes present in whole blood, and wherein the compound is cleavable by an enzyme associated with the target cell, the enzyme associated with the target cell being other than TOP, or a salt thereof, such that the patient is treated.

30. The method of claim 28 or 29, wherein the compound is resistant to cleavage by TOP.

31. The method of claim 28 or 29, wherein the compound is administered intravenously.

32. The method of claim 28 or 29, wherein the patient is treated for a medical condition selected from cancer, neoplastic diseases, tumors, inflammatory diseases, or infectious diseases.

33. An article of manufacture for diagnosis or assay comprising:

(1) a compound comprising:

(a) a marker, (b) an oligopeptide of the formula (AA)$_n$-AA$^3$-AA$^2$-AA$^1$, wherein:

AA$^1$ is selected from the group consisting of Leucine, Phenylalanine, Isoleucine, Alanine, Glycine, Tyrosine, 2-Naphthylalanine, Serine, Proline, and β-Alanine, AA$^2$ is selected from the group consisting of: Alanine, Leucine, Glycine, Serine, Tyrosine, 3-Pyridylalanine, 2-Thienylalanine, N-Methylalanine, Aminoisobutyric Acid, Threonine, and Phenylalanine, AA$^3$ represents isoleucine, n is 0 or 1, and when n is 1 then (AA)$_n$ is AA$^4$ which represents any amino acid, (c) a stabilizing group, and (d) optionally, a linker group not cleavable by TOP, wherein the oligopeptide is directly linked to the stabilizing group at a first attachment site of the oligopeptide and AA$^1$ of the oligopeptide is directly linked to the marker or indirectly linked through the linker group to the marker at a second attachment site of the oligopeptide, wherein the stabilizing group hinders cleavage of the compound by enzymes present in whole blood, and wherein the compound is cleavable by an enzyme associated with a target cell, the enzyme associated with the target cell being other than TOP, and further wherein the compound is resistant to cleavage by TOP, and (2) at least one reagent useful in the detection of said marker.

34. The article of manufacture according to claim 33 wherein AA$^4$ is selected from β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

35. The article of manufacture according to claim 33 wherein the oligopeptide is βAla-Ile-Ala-Leu (SEQ ID NO: 8).

36. The article of manufacture according to claim 33 wherein the stabilizing group is negatively charged or neutral.

37. The article of manufacture according to claim 33 wherein the stabilizing group is a dicarboxylic or higher order carboxylic acid.

38. The article of manufacture according to claim 33 wherein the stabilizing group is selected from the group consisting of succinic acid, adipic acid, glutaric acid, phthalic acid, diglycolic acid, fumaric acid, naphthalene dicarboxylic acid, pyroglutamic acid, acetic acid, 1-naphthylcarboxylic acid, 2-naphthylcarboxylic acid, 1,8-naphthyl dicarboxylic acid, aconitic acid, carboxycinnamic acid, triazole dicarboxylic acid, gluconic acid, 4-carboxyphenyl boronic acid, polyethylene glycolic acid, butane disulfonic acid, maleic acid, nipecotic acid, and isonipecotic acid.

39. The article of manufacture according to claim 33 wherein the stabilizing group is a non-genetically encoded amino acid.

40. The article of manufacture according to claim 33 wherein the stabilizing group is selected from the group consisting of: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

41. The article of manufacture according to claim 33 wherein the stabilizing group is one of aspartic acid linked to the oligopeptide at the β-carboxy group of the aspartic acid or glutamic acid linked to the oligopeptide at the γ-carboxy group of the glutamic acid.

* * * * *

SEQUENCE LISTING

<160> NUMBER OF SEQ ID NOS: 79

<210> SEQ ID NO 1
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE

```
<222> LOCATION: (1)..(1)
<223> OTHER INFORMATION: Beta-Alanine

<400> SEQUENCE: 1

Xaa Ile Ala Phe
1

<210> SEQ ID NO 2
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 2

Xaa Ile Ala Ile
1

<210> SEQ ID NO 3
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Tetrahydroisoquinoline-3-carboxylic acid

<400> SEQUENCE: 3

Xaa Ile Ala Leu
1

<210> SEQ ID NO 4
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-Thienylalanine

<400> SEQUENCE: 4

Xaa Ile Ala Leu
1

<210> SEQ ID NO 5
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-Naphthylalanine

<400> SEQUENCE: 5

Xaa Ile Ala Leu
1

<210> SEQ ID NO 6
<211> LENGTH: 4
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 4-(Aminomethyl)benzoic acid

<400> SEQUENCE: 6

Xaa Ile Ala Leu
1

<210> SEQ ID NO 7
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Aminoisobutyric acid

<400> SEQUENCE: 7

Xaa Ile Ala Leu
1

<210> SEQ ID NO 8
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 8

Xaa Ile Ala Leu
1

<210> SEQ ID NO 9
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-Thienylalanine
<220> FEATURE:
<221> NAME/KEY: MISC_FEATURE
<222> LOCATION: (3)..(3)
<223> OTHER INFORMATION: Aminoisobutyric acid

<400> SEQUENCE: 9

Xaa Ile Xaa Leu
1

<210> SEQ ID NO 10
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: 2-Naphthylalanine
<220> FEATURE:
<221> NAME/KEY: MISC_FEATURE
<222> LOCATION: (3)..(3)
<223> OTHER INFORMATION: Aminoisobutyric acid

<400> SEQUENCE: 10

Xaa Ile Xaa Leu
1

<210> SEQ ID NO 11
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (3)..(3)
<223> OTHER INFORMATION: Aminoisobutyric acid

<400> SEQUENCE: 11

Xaa Ile Xaa Leu
1

<210> SEQ ID NO 12
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 4-(Aminomethyl)benzoic acid
<220> FEATURE:
<221> NAME/KEY: MISC_FEATURE
<222> LOCATION: (3)..(3)
<223> OTHER INFORMATION: Aminoisobutyric acid

<400> SEQUENCE: 12

Xaa Ile Xaa Leu
1

<210> SEQ ID NO 13
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Aminoisobutyric acid
<220> FEATURE:
<221> NAME/KEY: MISC_FEATURE
<222> LOCATION: (3)..(3)
<223> OTHER INFORMATION: Aminoisobutyric acid

<400> SEQUENCE: 13

Xaa Ile Xaa Leu
1

<210> SEQ ID NO 14
<211> LENGTH: 4
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 14

Xaa Ile Gly Phe
1

<210> SEQ ID NO 15
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 15

Xaa Ile Gly Ile
1

<210> SEQ ID NO 16
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Tetrahydroisoquinoline-3-carboxylic acid

<400> SEQUENCE: 16

Xaa Ile Gly Leu
1

<210> SEQ ID NO 17
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-Thienylalanine

<400> SEQUENCE: 17

Xaa Ile Gly Leu
1

<210> SEQ ID NO 18
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 2-Naphthylalanine

<400> SEQUENCE: 18

Xaa Ile Gly Leu
1
```

```
<210> SEQ ID NO 19
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 19

Xaa Ile Gly Leu
1

<210> SEQ ID NO 20
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 4-(Aminomethyl)benzoic acid

<400> SEQUENCE: 20

Xaa Ile Gly Leu
1

<210> SEQ ID NO 21
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Aminoisobutyric acid

<400> SEQUENCE: 21

Xaa Ile Gly Leu
1

<210> SEQ ID NO 22
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 22

Xaa Ile Thr Ile
1

<210> SEQ ID NO 23
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Beta-Alanine

<400> SEQUENCE: 23

Xaa Ile Tyr Ile
1

<210> SEQ ID NO 24
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 24

Xaa Ile Ala Gly
1

<210> SEQ ID NO 25
<211> LENGTH: 3
<212> TYPE: PRT
<213> ORGANISM: Artificial sequence
<220> FEATURE:
<223> OTHER INFORMATION: Synthetic

<400> SEQUENCE: 25

Ile Ala Leu
1

<210> SEQ ID NO 26
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: N-Methylalanine

<400> SEQUENCE: 26

Ile Xaa Leu
1

<210> SEQ ID NO 27
<211> LENGTH: 3
<212> TYPE: PRT
<213> ORGANISM: Artificial sequence
<220> FEATURE:
<223> OTHER INFORMATION: Synthetic

<400> SEQUENCE: 27

Ile Ala Phe
1

<210> SEQ ID NO 28
<211> LENGTH: 3
<212> TYPE: PRT
<213> ORGANISM: Artificial sequence
<220> FEATURE:
<223> OTHER INFORMATION: Synthetic

<400> SEQUENCE: 28

Ile Ala Ile
1
```

```
<210> SEQ ID NO 29
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Aminoisobutyric acid

<400> SEQUENCE: 29

Ile Xaa Leu
1

<210> SEQ ID NO 30
<211> LENGTH: 3
<212> TYPE: PRT
<213> ORGANISM: Artificial sequence
<220> FEATURE:
<223> OTHER INFORMATION: Synthetic

<400> SEQUENCE: 30

Ile Gly Phe
1

<210> SEQ ID NO 31
<211> LENGTH: 3
<212> TYPE: PRT
<213> ORGANISM: Artificial sequence
<220> FEATURE:
<223> OTHER INFORMATION: Synthetic

<400> SEQUENCE: 31

Ile Gly Ile
1

<210> SEQ ID NO 32
<211> LENGTH: 3
<212> TYPE: PRT
<213> ORGANISM: Artificial sequence
<220> FEATURE:
<223> OTHER INFORMATION: Synthetic

<400> SEQUENCE: 32

Ile Gly Leu
1

<210> SEQ ID NO 33
<211> LENGTH: 3
<212> TYPE: PRT
<213> ORGANISM: Artificial sequence
<220> FEATURE:
<223> OTHER INFORMATION: Synthetic

<400> SEQUENCE: 33

Ile Thr Ile
1

<210> SEQ ID NO 34
<211> LENGTH: 3
<212> TYPE: PRT
<213> ORGANISM: Artificial sequence
<220> FEATURE:
<223> OTHER INFORMATION: Synthetic

<400> SEQUENCE: 34
```

Ile Ala Gly
1

<210> SEQ ID NO 35
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 35

Xaa Ile Tyr Leu
1

<210> SEQ ID NO 36
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine

<400> SEQUENCE: 36

Xaa Ile Tyr Gly
1

<210> SEQ ID NO 37
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine

<400> SEQUENCE: 37

Xaa Ile Ala Leu
1

<210> SEQ ID NO 38
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Methyl-succinyl-Beta-Alanine

<400> SEQUENCE: 38

Xaa Ile Ala Leu
1

<210> SEQ ID NO 39
<211> LENGTH: 4
<212> TYPE: PRT
<213> ORGANISM: Artificial sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 39

Xaa Ile Ala Xaa
 1

<210> SEQ ID NO 40
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 40

Xaa Ile Ala Xaa
 1

<210> SEQ ID NO 41
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine

<400> SEQUENCE: 41

Xaa Leu Ala Leu
 1

<210> SEQ ID NO 42
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 42

Xaa Leu Ala Xaa
 1

<210> SEQ ID NO 43
<211> LENGTH: 4
<212> TYPE: PRT
<213> ORGANISM: Artificial sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 43

Xaa Ile Ala Xaa
 1

<210> SEQ ID NO 44
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine

<400> SEQUENCE: 44

Xaa Ile Ala Leu
 1

<210> SEQ ID NO 45
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Allyl-succinyl-Beta-Alanine

<400> SEQUENCE: 45

Xaa Ile Ala Leu
 1

<210> SEQ ID NO 46
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Allyl-succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 46

Xaa Ile Ala Xaa
 1

<210> SEQ ID NO 47
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Methyl-hemisuccinyl-Beta-Alanine

<400> SEQUENCE: 47

Xaa Ile Ala Leu
1

<210> SEQ ID NO 48
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 48

Xaa Ile Ala Xaa
1

<210> SEQ ID NO 49
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Phenylalanine-daunorubicin

<400> SEQUENCE: 49

Xaa Ile Ala Xaa
1

<210> SEQ ID NO 50
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 50

Xaa Ile Ala Xaa
1

<210> SEQ ID NO 51
<211> LENGTH: 4
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Succinyl-Tetrahydroisoquinoline-3-carboxylic
      acid
<220> FEATURE:
<221> NAME/KEY: MISC_FEATURE
<222> LOCATION: (4)..(4)
<223> OTHER INFORMATION: Leucine-daunorubicin

<400> SEQUENCE: 51

Xaa Ile Ala Xaa
1

<210> SEQ ID NO 52
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 52

Xaa Ile Ala Xaa
1

<210> SEQ ID NO 53
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 53

Xaa Ile Ala Xaa
1

<210> SEQ ID NO 54
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (4)..(4)
<223> OTHER INFORMATION: Leucine-daunorubicin

<400> SEQUENCE: 54

Xaa Ile Ala Xaa
1

<210> SEQ ID NO 55
```

```
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 55

Xaa Ile Ala Xaa
 1

<210> SEQ ID NO 56
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 56

Xaa Ile Xaa Xaa
 1

<210> SEQ ID NO 57
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 57

Xaa Ile Xaa Xaa
 1

<210> SEQ ID NO 58
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Succinyl-Beta-Alanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 58

Xaa Ile Xaa Xaa
1

<210> SEQ ID NO 59
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-doxorubicin

<400> SEQUENCE: 59

Xaa Ile Xaa Xaa
1

<210> SEQ ID NO 60
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 60

Xaa Ile Xaa Xaa
1

<210> SEQ ID NO 61
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
```

<223> OTHER INFORMATION: Phenylalanine-daunorubicin

<400> SEQUENCE: 61

Xaa Ile Gly Xaa
1

<210> SEQ ID NO 62
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 62

Xaa Ile Gly Xaa
1

<210> SEQ ID NO 63
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Tetrahydroisoquinoline-3-carboxylic
    acid
<220> FEATURE:
<221> NAME/KEY: MISC_FEATURE
<222> LOCATION: (4)..(4)
<223> OTHER INFORMATION: Leucine-daunorubicin

<400> SEQUENCE: 63

Xaa Ile Gly Xaa
1

<210> SEQ ID NO 64
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 64

Xaa Ile Gly Xaa
1

<210> SEQ ID NO 65
<211> LENGTH: 4
<212> TYPE: PRT
<213> ORGANISM: Artificial sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 65

Xaa Ile Gly Xaa
1

<210> SEQ ID NO 66
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 66

Xaa Ile Gly Xaa
1

<210> SEQ ID NO 67
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (4)..(4)
<223> OTHER INFORMATION: Leucine-daunorubicin

<400> SEQUENCE: 67

Xaa Ile Gly Xaa
1

<210> SEQ ID NO 68
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 68

Xaa Ile Gly Xaa
1

<210> SEQ ID NO 69
<211> LENGTH: 4
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 69

Xaa Ile Thr Xaa
1

<210> SEQ ID NO 70
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 70

Xaa Ile Tyr Xaa
1

<210> SEQ ID NO 71
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 71

Xaa Ile Tyr Xaa
1

<210> SEQ ID NO 72
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Glycine-doxorubicin

<400> SEQUENCE: 72

Xaa Ile Tyr Xaa
```

```
<210> SEQ ID NO 73
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Glycine-doxorubicin

<400> SEQUENCE: 73

Xaa Ile Ala Xaa
1

<210> SEQ ID NO 74
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 74

Xaa Leu Ala Xaa
1

<210> SEQ ID NO 75
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 75

Xaa Ile Ala Xaa
1

<210> SEQ ID NO 76
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine
<220> FEATURE:
<221> NAME/KEY: MISC_FEATURE
<222> LOCATION: (4)..(4)
```

<223> OTHER INFORMATION: Leucine-OBn

<400> SEQUENCE: 76

Xaa Ile Ala Xaa
1

<210> SEQ ID NO 77
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-OBn

<400> SEQUENCE: 77

Xaa Ile Ala Xaa
1

<210> SEQ ID NO 78
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-OBn

<400> SEQUENCE: 78

Xaa Ile Ala Xaa
1

<210> SEQ ID NO 79
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 79

Xaa Leu Ala Xaa
1